US007736656B2

(12) United States Patent
Hart et al.

(10) Patent No.: US 7,736,656 B2
(45) Date of Patent: *Jun. 15, 2010

(54) IMMUNOGENIC COMPOSITIONS AND VACCINES FOR EBOLA

(75) Inventors: Mary Kate Hart, Frederick, MD (US); Gene Garrard Olinger, Jr., Frederick, MD (US); Michael Adam Bailey, Montgomery Village, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 576 days.

This patent is subject to a terminal disclaimer.

(21) Appl. No.: 11/068,179

(22) Filed: Feb. 28, 2005

(65) Prior Publication Data

US 2010/0034843 A1     Feb. 11, 2010

Related U.S. Application Data

(63) Continuation-in-part of application No. 10/696,633, filed on Oct. 29, 2003, now Pat. No. 6,984,504, which is a continuation of application No. 09/337,946, filed on Jun. 22, 1999, now abandoned, application No. 11/068,179, which is a continuation-in-part of application No. 10/384,976, filed on Mar. 10, 2003, now Pat. No. 7,267,823, which is a continuation-in-part of application No. 09/337,946, filed on Jun. 22, 1999, now abandoned.

(60) Provisional application No. 60/091,403, filed on Jun. 29, 1998.

(51) Int. Cl.
    *A61K 39/12*      (2006.01)

(52) U.S. Cl. ............................... 424/186.1; 424/204.1

(58) Field of Classification Search ........................ None
See application file for complete search history.

(56) References Cited

U.S. PATENT DOCUMENTS

| | | | |
|---|---|---|---|
| 5,792,462 A | 8/1998 | Johnston et al. | 424/199.1 |
| 5,977,316 A | 11/1999 | Chatterjee et al. | 530/387.2 |
| 6,340,463 B1 | 1/2002 | Mitchell et al. | 424/263.1 |
| 6,630,144 B1 | 10/2003 | Hart et al. | 424/159 |
| 6,713,069 B1 * | 3/2004 | Gallaher | 424/218.1 |
| 7,267,823 B2 * | 9/2007 | Hart et al. | 424/204.1 |
| 2004/0053865 A1 | 3/2004 | Hart et al. | |
| 2004/0146859 A1 | 7/2004 | Hart et al. | |

FOREIGN PATENT DOCUMENTS

| | | |
|---|---|---|
| WO | WO 96/37616 | 11/1996 |
| WO | WO 99/32147 | 7/1999 |
| WO | WO 00/00617 | 1/2000 |
| WO | WO 01/16183 | 3/2001 |

OTHER PUBLICATIONS

Geisbert et al., Nature Medicine, Dec. 2004, 10(12):S110-S121.*
Jones et al., Nature Medicine, Jul. 2005, 11(7):786-790.*
Olinger et al., Journal of Virology, Nov. 2005, 79(22):14189-14196.*
Warfield et al. Ebola Virus-Like Particle-Based Vaccine Protects Nonhuman Primates against Lethal Ebola Virus Challenge, Journal of Infectious Diseases, 2007, vol. 196, Supplement 2, pp. S430-S437.*
Volchkov et al., "The envelope glycoprotein of Ebola virus contains an immunosuppressive-like domain similar to oncogenic retroviruses", FEBS Letters, vol. 305, No. 3, pp. 181-184 (Jul. 1992).
Sanchez et al., "Biochemical Analysis of the Secreted and Virion Glycoproteins of Ebola Virus", J. Virology, Aug. 1998, vol. 72, pp. 6442-6447.
Wilson et al. "Epitopes Involved in Antibody-Mediated Protection from Ebola Virus", Science, vol. 387, Mar. 3, 2000, pp. 1664-1666.
Ichihashi and Oie, "Neutralizing Epitope on Penetration Protein of Vaccinia Virus", Virology 220, pp. 491-494 (1996).
Wolffe et al., "A myristylated membrane protein encoded by the vaccinia virus L1R open reading frame is the target of potent neutralizing monoclonal antibodies", Virology 211, pp. 53-63 (1995).
Roper et al., "Extracellular vaccinia virus envelope glycoprotein encoded by the A33R gene", J. Virology, Jun. 1996, vol. 70, No. 6, pp. 3753-3762.
Isaacs et al., "Characterization of a vaccinia virus-encoded 42-kilodalton class I membrane glycoprotein component of the extracellular virus envelope", J. Virology, Dec. 1992, vol. 66, No. 12, pp. 7217-7224.
Abstract W33-5, "DNA vaccination against poxviruses using combinations of IMV and EEV immunogens", presented Jul. 2000, American Society for Virology Meeting, pp. 113.
Abstract P23-6, "DNA immunization with the vaccinia L1R and/or A33R genes", Jul. 1998, poster at American Society for Virology meeting.
Meyer et al., "Identification of binding sites for neutralizing monoclonal antibodies on the I4-kDa fusion protein of orthodox viruses", Virology 200, Short Communications, pp. 778-783 (1994).
Czerny and Mahnel, "Structural and functional analysis of orthopoxvirus epitope with neuralizing monoclonal antibodies", J. General Virology (1990), vol. 71, pp. 2341-2352.
Hooper et al., "DNA vaccination with vaccinia virus L1R and A33R genes protects mice against a lethal poxvirus challenge", Virology 266, pp. 329-339 (2000).
Vazquez and Esteban, "Identification of functional domains in the 14-kilodalton envelope protein (A27L) of vaccinia virus", J. Virology, Nov. 1999, vol. 73, No. 11, pp. 9098-9109.
Vazquez et al., "The vaccinia virus 14-kilodalton (A27L) fusion protein forms a triple coiled-coil structure and interacts with the 21-kilodalton (A17L) virus membrane protein through a C-terminal of alpha-helix", J. Virology, Dec. 1998, vol. 72, No. 12, pp. 10126-10137.

(Continued)

*Primary Examiner*—Stacy B Chen
(74) *Attorney, Agent, or Firm*—Elizabeth Arwine

(57) ABSTRACT

Using CTL epitopes to the Ebola GP, NP, VP24, VP30, VP35 and VP40 virion proteins, a method and composition for use in inducing an immune response which is protective against infection with Ebola virus is described.

3 Claims, 11 Drawing Sheets

OTHER PUBLICATIONS

Rodriguez et al., "The vaccinia virus 14-kilodalton fusion proteins forms a stable complex with the processed protein encoded by the vaccinia virus A17L gene", J. Virology, Jun. 1993, vol. 67, No. 6, pp. 3435-3440.

Lai et al., "The purified 14-kilodalton envelope protein of vaccinia virus produced in *Escherichia coli* induces virus immunity in animals", J. Virology, Oct. 1991, vol. 65, No. 10, pp. 5631-5635.

Rodriguez and Esteban, "Mapping and nucleotide sequence of the vaccinia virus gene that encodes a 14-kilodalton fusion protein," J. Virology, Nov. 1987, vol. 61, No. 11, pp. 3550-3554.

Rodriguez et al., "Isolation and characterization of neutralizing monoclonal antibodies to vaccinia virus", J. Virology, Nov. 1985, vol. 56, No. 2, pp. 482-488.

NCBI PubMed medline, Abstract for Rodriguez et al., "Isolation and characterization of neutralizing monoclonal antibodies to vaccinia virus", J. Virology, Nov. 1985, vol. 56, No. 2, pp. 482-488.

Lin et al., "Vaccinia virus envelope H3L protein binds to cell surface heparan sulfate and is important for intracellular mature virion morphorogenesis and virus infection in vitro and in vivo", J. Virology, Apr. 2000, vol. 74, No. 7, pp. 3353-3365.

Gordon et al., "A prominent antigenic surface polypeptide involved in the biogenesis and function of the vaccinia virus envelope". Virology 181, pp. 671-686 (1991).

Ichihashi et al., "Identification of a vaccinia virus penetration protein", Virology 202, pp. 834-843 (1994).

Demkowicz et al., "Identification and characterization of vaccinia virus genes encoding proteins that are highly antigenic in animals and are immunodominant in vaccinated humans", J. Virology, Jan. 1992, vol. 66, No. 1, pp. 386-398.

Wilson et al., "Ebola virus: the search for vaccines and treatments", CMLS Cell., Mol. Life Sci., 58 (2001) pp. 1-16.

Pushko et al, "Venezuelan Equine Encephalitis virus replicon vector: immunogenicity studies with ebola NP and GP genes in guinea pigs", Vaccines 97, Molecular Approaches to the Control of Infectious Diseases, Cold Spring Harbor Laboratory Press. 1997, pp. 253-258.

Geisbert et al., "Evaluation in nonhuman primates of vaccines against Ebola virus", Perspectives, Emerging Infectious Diseases, vol. 8, No. 5, May 2002, pp. 503-507.

Pushko et al., "Recombinant RNA replicons derived from attenuated Venezuelan equine encephalitis virus protect guinea pigs and mice from Ebola hemorrhagic fever virus", Vaccine 11 (2000) pp. 1-12.

Wilson et al., "Vaccine potential of Ebola virus VP24, VP30, VP35, and VP40 proteins", Virology 286, pp. 384-390 (2001).

Wilson and Hart, "Protection from Ebola virus mediated by cytotoxic T lymphocytes specific for the viral nucleoprotein", J. Virology, Mar. 2001, vol. 75, No. 6, pp. 2660-2664.

Maruyama et al., "Recombinant human monoclonal antibodies to Ebola virus", J. Infectious Diseases, 1999, 179 (Suppl I), pp. S235-S239.

Jahrling et al., "Evaluation of immune globulin and recombinant interferon-alpha2b for treatment of experimental Ebola virus infections", J. Infectious Diseases, 1999, 170 (Suppl 1), pp. S224-S234.

Volchkov et al., "Release of viral glycoproteins during Ebola virus infection", Virology 245, pp. 110-119 (1998).

GenBank, Database printout, for Sanchez et al., Ebola virus nuceoprotein, polymerase copmlex protein (VP35), matrix protein (VP40), glycoprotein (GP), minor nucleoprotein (VP30), and membrance-associates structural protein (VP24), Oct. 14, 1997 (7 pages).

Hevey et al., "Antigenicity and vaccine potential of Marburg virus glycoprotein expressed by baculovirus recombinants", Virology 239, pp. 206-216 (1997).

Maruyama et al., "Ebola virus can be effectively neutralized by antibody produced in natural human infection", J. Virology, Jul. 1999, vol. 73, No. 7, pp. 6024-6030.

Wilson et al., "Ebola virus: the search for vaccines and treatments", CMLS, Cell. Mol. Life Sci. 58 (2001), pp. 1826-1841.

Maruyama et al., "Recombinant human monoclonal antibodies to Ebola virus", J. Infectious Diseases, 1999, 179 (Suppl I), pp. S235-S239).

Sanchez et al., "The virion glycoproteins of Ebola viruses are encoded in two reading frames and are expressed through transcriptional editing", PNAS, USA, vol. 93, pp. 3602-3607, Apr. 1996.

Jahrling et al., "Passive immunization of Ebola virus-infected cynomolgus monkeys with immunoglobulin from hyperimmune horses", Arch Virol, 1996 (Suppl) 11, pp. 135-140.

Parren et al., "Pre-and postexposure prophylaxis of ebola virus infectin in an animal model by passive tranfer of a neutraling human antibody," J. Virology, Jun. 2002, vol. 76, No. 12, pp. 6408-6412.

Wilson et al., "Epitopes involved in antobody-mediated protection from ebola virus",Science, vol. 287, pp. 1664-1666, Mar. 3, 2000.

Sanchez et al., "Detection and molecular characterization of ebola viruses causing disease in human and nonhuman primates", J. Infectious Diseases, 1999, vol. 179 (Suppl. I), pp. S164-S169.

Sanchez et al., "Biochemical analysis of the secreted and virion glycoproteins of ebola virus", J. Virology, Aug. 1998, vol. 72, No. 8, pp. 6442-6447.

Khaw et al., "Technetium-99m labeling of antibodies to cardiac myosin fab and to human fibrinogen", Radiochemistry and Radiopharmaceuticals, J. Nucl. Med., vol. 23, No. 11, pp. 1011-1019, Nov. 1982.

Farid et al., "Idiotypes, paratopes and molecular mimicry", pp. 1-5, and "An idiotype approach for a vaccine against hepatitus B surface antigen", pp. 285-300, both in Anti-Idiotypes, Receptors, and Molecular Mimicry, Ivy Springer-Verlag, 1988.

Kabat et al., Sequence of proteins of immunological interest, vol. 1, Fifth ed., pp. xiv-xix and 33 pages of sequences (1991).

Waldmann, "Manipulation of T-cell responses with monoclonal antibodies", Ann. Rev. Immunol. (1989) 7:407-444.

Kennedy et al., "Review: Protein-protein coupling reactions and the applications of protein conjugates", Clinica Chimica Acts 70 (1976) pp. 1-31.

"Continuous cultures of fused cells secreting antibody of predefined specificity", Nature, vol. 256, pp. 495-497 (1975).

Volchkov et al., "Processing of the ebola virus glycoprotein by the proprotein convertase furin", PNAS USA, vol. 95, pp. 5762-5767 (May 1998).

Stiles et al., "Production and characterization of monoclonal antibodies against NAJA NAJA ATRA cobrotoxin",Toxicon, vol. 29, No. 10, pp. 1195-1204 (1991).

Feldmann et al., "Marburg virus, a filovirus: messenger RNAs, gene order, and regulatory elements of the replication cycle", Virus Research, 24 (1992) pp. 1-19.

Peters and LeDuc, "An introduction to ebola: the virus nad the disease", J. Infectious Diseases, 1999, vol. 179 (Suppl I), pp. ix-xvi.

Kudoyarova-Zubavichene et al., "Preparation and use of hyperimmune serum for prophylaxis and therapy of ebola virus infections", J. Infectious Diseases, 1999, vol. 179 (Suppl 1), pp. S218-S223.

Moe et al., "Plaque assay for ebola virus", J. Clinical Microbiology, Apr. 1981, vol. 13, No. 4, pp. 791-793.

Waldmann, "Manipulation of T-cell responses wit hmonoclonal antibodies", Ann. Rev. Immunol., 1989, vol. 7, pp. 407-444.

Mikhailov et al., "An evaluation of the possibility of ebola fever specific prophylaxis in baboons", Voprosy Virusologii, No. 2, pp. 82-84, 1994.

Harlow and Lane, "Antibodies: A Laboratory Manual", Chapter 6, pp. 210-213 (Cold Spring Harbor Laboratory, New York) 1988.

Schuurs and Van Weemen, "Review" Enzyme-Immunoassay, Clinica Chimica Acta, 81 (1977), pp. 1-40.

PubMed Abstract from National Library of Medicine, Sanderson et al., "The vaccinia virus A27L protein is needed for the microtubule-dependent transport of intracellular mature virus particles", from Virology 1999, 264(2), at pp. 298-318.

Gilligan et al., "Assessment of protective immunity conferred by recombinant vaccinia viruses to guinea pigs challenged with ebola virus", Vaccines 97, 1997, pp. 87-92.

Xu et al., "Immunization for ebola virus infection", Nature Medicine, NO.v 4, No. 1, Jan. 1998, pp. 37-42.

Davis et al., "A viral vaccine vector that expresses foreign genes in lymph nodes and protects against mucosal challenge", J. Virology, Jun. 1996, vol. 70, No. 6, pp. 3781-3787.

Grieder et al., "Specific restrictions in the progression of Venezuelan equine encephalitis virus-induced disease resulting from single amino acid changes in the glycoproteins", Virology 206, pp. 994-1006 (1995).

Volchkov et al., "GP mRNA of ebola virus is edited by the ebola virus polymerase and by T7 and vaccinia virus polymerases", Virology 214, pp. 421-430 (1995).

Sanchez et al., "Variation in the glycoprotein and VP35 genes of Marburg virus strains", Virology 240, pp. 138-146 (1998).

Vanderzanden et al., "DNA vaccines expressing either the GP or NP genes of ebola virus protect mice from lethal challenge", Virology 246, pp. 134-144 (1998).

Sanchez et al., "The nucleoprotein gene of ebola virus: cloning, sequencing, and in vitro expression", Virology 170, pp. 81-91 (1989).

Sanchez et al., "Sequence analysis of the ebola virus genome: organization, genetic elements, and comparison with the genome of Marburg virus", Virus Research, 29, pp. 215-240 (1993).

Abstract XP-002131517, Pushko et al., "Venezuelan equine encephalitis virus replicon vector: immunogenicity studies with ebola NP and GP genes in guinea pigs", 1997.

Nicolet and Paulnock, "Promoter analysis of an interferon-inducible gene associated with macrophage activation", J. Immunology, 1994, pp. 152-162.

Hart et al., "Priming of anti-human immunoeficiency virus (HIV) CD8+ cytotoxic T cells in vivo by carrier-free HIV synthetic peptides", PNAS USA, vol. 88, pp. 9448-9452 (Nov. 1991).

Elliott et al., "Ebola protein analyses for the determination of genetic organization", Arch Virol (1993), 133:423-436.

Bukreyev et al., "The VP35 and VP40 proteins of filoviruses; Homology between Marburg and Ebola viruses", FEBS, vol. 322, No. 1, pp. 41-46 (May 1993).

Hevey et al., "Marburg virus vaccines based upon alphavirus replicons protect guinea pigs and nonhuman primates", Virology 251, pp. 28-37 (1998).

Pushko et al., "Replicon-helper systems from attenuated Venezuelan equine encephalitis virus; expression of heterologous genes in vitro and immunization against heterologous pathogens in vivo," Virology 239, pp. 389-401 (1997).

Bray et al., "A mouse model for evaluation of prophylaxis and therapy of ebola hemorrhagic fever", J. Infectious Diseases, 1998, vol. 178, pp. 651-661.

Hart, "Vaccine research efforts for filoviruses", International Journal for Parasitology, 33 (2003) 583-595.

Sullivan et al.,"Accelerated vaccination for Ebola virus haemorrhagic fever in non-human primates", Letters to Nature, Nature, vol. 424, Aug. 7, 2003, pp. 681-684.

Parker, "Scheme for Ranking Poteneial HLA-A2 Binding Peptides Based on Independent Binding of Individual Peptides Side-Chains" Journal of Immunology, 1994, vol. 152, pp. 163-175.

Sullivan et al., "Development of a preventive vaccine for Ebola virus infection in primates", Letters to Nature, Nature, 2001, 4 pages.

Bukreyev et al., "The VP35 and VP40 proteins of flaviviruses", FEBS, vol. 322, No. 1, pp. 41-46, May 1993.

Elliott et al., "Ebola protein analyses for the determination of genetic organization", Arch. Virol. (1993), 133:423-436.

Elliott et al, "Descriptive analysis of Ebola virus proteins", Virology, vol. 147, No. 1, 1985, pp. 169-176.

* cited by examiner

FIGURE 1

Organization of the Ebola Virus Genome

3' | NP | VP35 | VP40 | GP (sGP) | VP30 | VP24 | L | 5'

NP   Major Nucleocapsid Protein
VP35 Phosphoprotein
VP40 Membrane-Associated Matrix Protein
GP   Transmembrane Glycoprotein
sGP  Secreted Glycoprotein
VP30 Ribonucleoprotein Associated (Minor)
VP24 Membrane-Associated Protein (Minor)
L    RNA-Dependent RNA Polymerase

Part 2 ŠVRP Group (SC VRP-GP)

IMMUNOGENIC COMPOSITIONS AND VACCINES FOR EBOLA

BACKGROUND OF THE INVENTION

This application is a continuation-in-part of U.S. utility application Ser. No. 10/696,633, filed Oct. 29, 2003 (now U.S. Pat. No. 6,984,504, issued Jan. 10, 2006), which is a continuation application of U.S. utility application Ser. No. 09/337,946, filed Jun. 22, 1999 (now abandoned), which claims priority from U.S. provisional application 60/091,403 (filed Jun. 29, 1998). This application is also a continuation-in-part of U.S. utility application Ser. No. 10/384,976, filed Mar. 10, 2003 (now U.S. Pat. No. 7,267,823, issued Sep. 11, 2007), which is a continuation-in-part application of U.S. utility application Ser. No. 09/337,946, filed Jun. 22, 1999 (now abandoned), which claims priority from U.S. provisional application 60/091,403 (filed Jun. 29, 1998). The entire contents of these applications are incorporated herein by reference.

Ebola viruses, members of the family Filoviridae, are associated with outbreaks of highly lethal hemorrhagic fever in humans and nonhuman primates. The natural reservoir of the virus is unknown and there currently are no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection (FIG. 1). Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) *Virus Res.* 24, 1-19; Sanchez et al., (1993) *Virus Res.* 29, 215-240; reviewed in Peters et al. (1996) *In Fields Virology*, Third ed. pp. 1161-1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) *Proc. Natl. Acad. Sci. USA* 93, 3602-3607; Volchkov et al, (1995) *Virology* 214, 421-430). The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

Recent studies using rodent models to evaluate subunit vaccines for Ebola virus infection using recombinant vaccinia virus encoding Ebola virus GP (Gilligan et al., (1997) *In Vaccines 97*, pp. 87-92. Cold Spring Harbor Laboratory Press, Cold Spring Harbor, N.Y.), or naked DNA constructs expressing either GP or sGP (Xu et al. (1998) *Nature Med.* 4, 37-42) have demonstrated the protective efficacy of Ebola virus GP in guinea pigs. (All documents cited herein supra and infra are hereby incorporated in their entirety by reference thereto.) Additionally, Ebola virus NP and GP genes expressed from naked DNA vaccines (Vanderzanden et al., (1998) *Virology* 246, 134-144) have elicited protective immunity in BALB/c mice. There has been one study that showed protection in nonhuman primates with a high dose DNA prime/high dose adenovirus boost and a 6 pfu challenge. However, this study provides limited benefit for humans or non-human primates because such high dosing is unlikely to be given to humans due to high inherent risks and other factors.

VRPs are one platform currently being evaluated for the filoviruses. VRP constructs expressing six Ebola virus proteins (GP, nucleoprotein, VP24, VP30, VP35 and VP40) are efficacious in mice. VRP expressing GP induced protective antibody responses and were used to generate protective monoclonal antibodies (Wilson et al. Science 2000.). In contrast, the other proteins induce protective cytotoxic T cell responses. The involvement of cytotoxic T cells in protection presents an immunologic issue (major histocompatibility complex restriction of the presentation of epitopes) not present for pathogens cleared by antibodies.

Non-human primate studies using VRPs to protect against filovirus challenge have had different results. The successful protection of vaccinated cynomolgus macaques against Marburg Musoke virus was the first published success of any filovirus vaccine approach. In one published study, a vaccination schedule ($1\times10^7$ ffu on days 0, 28 and 56) using the VRP expressing Ebola Zaire GP induced rather modest antibody titers and the macaques did not survive challenge with 1000 pfu.

So there still exists a need for a human vaccine which is efficacious for protection from Ebola virus infection.

SUMMARY OF THE INVENTION

The present invention satisfies the need discussed above. The present invention relates to a method and composition for use in inducing an immune response which is protective against infection with Ebola virus.

The inventors have induced protection against Ebola infection in mammals using virus replicon particles (VRPs) expressing the Ebola GP, NP, VP24, VP30, VP35 or VP40 genes. These VRPs and some uses are described in U.S. utility patent application Ser. No. 09/337,946 (filed Jun. 22, 1999), the entire contents of which are hereby incorporated by reference.

One embodiment of the present invention entails a DNA fragment encoding each of the Ebola Zaire 1976 GP, NP, VP24, VP30, VP35, and VP40 virion proteins (SEQUENCE ID NOS. 1-7).

Another embodiment provides the DNA fragments of Ebola virion proteins in a recombinant vector. When the vector is an expression vector, the Ebola virion proteins GP, NP, VP24, VP30, VP35, and VP40 are produced. It is preferred that the vector is an alphavirus replicon vector, especially a replicon vector that has the ability to produce the desired protein or peptide in a manner that induces protective B and T cells in vivo in mammals. Any alphavirus vector may be effective, including but not limited to the Venezuelan Equine Encephalitis (VEE) virus, eastern equine encephalitis, western equine encephalitis, Semliki forest and Sindbis. For instance, in a preferred embodiment the VEE replicon vector comprises a VEE virus replicon and a DNA fragment encoding any of the Ebola Zaire 1976 (Maying a isolate) GP, NP, VP24, VP30, VP35, or VP40 proteins. In another preferred embodiment, the VEE replicon vector comprises a VEE virus replicon and a DNA fragment encoding any of the amino acid sequences set forth in SEQ ID NOs:24-53. The construct can be used as a nucleic acid vaccine or for the production of self replicating RNA. To that end, a self replicating RNA of this invention can comprise the VEE virus replicon and any of the Ebola Zaire 1976 (Maying a isolate) RNAs encoding the GP, NP, VP24, VP30, VP35, and VP40 proteins described above, or the amino acid sequences set forth in SEQ ID NOs:24-53. The RNA can be used as a vaccine for protection from Ebola infection. When the RNA is packaged, a VEE virus replicon particle is produced.

Another embodiment entails infectious VEE virus replicon particles produced from the VEE virus replicon RNAs described above.

Another embodiment of the invention encompasses peptides that make up cytotoxic T lymphocyte (CTL) epitopes corresponding to Ebola GP, NP, VP24, VP30, VP35, or VP40 proteins. The epitopes may include the sequences identified as SEQ ID NOS:24-53, as described below. A related aspect of this embodiment provides DNA fragments that respectively encode these Ebola peptides. A further embodiment relates to recombinant DNA constructs that express these epitope peptides.

An additional embodiment includes a pharmaceutical composition that includes one or more of these CTL epitope peptides (and preferably one or more of SEQ ID NOs:24-53), in an effective immunogenic amount in a pharmaceutically acceptable carrier and/or adjuvant.

A further embodiment entails an immunological composition for the protection of mammals including humans against Ebola virus infection, comprising at least one (but preferably at least two, and more preferably at least three, and most preferably all) of the Ebola virus GP, NP, VP24, VP30, VP35, or VP40 proteins. In a related embodiment, the composition may include one or more of the CTL epitopes set forth in SEQ ID NOs: 24-53 (described below).

In a related preferred embodiment, the immunological compositions comprise alphavirus replicon particles (such as, for instance, VEE virus replicon particles) expressing the Ebola virus GP, NP, VP24, VP30, VP35, or VP40 proteins, or any combination of different VEE virus replicons each expressing one or more different Ebola proteins selected from GP, NP, VP24, VP30, VP35 and VP40—and preferably the composition includes replicons expressing each of the six proteins, in the form of a "cocktail". The six-protein cocktail, administered in the dosage, regimens and routes described below, has shown itself to be particularly successful as a protective composition. In a preferred embodiment the composition may include one or more of SEQ ID NOs: 24-53 (described below).

In a related preferred embodiment, the immunological compositions comprise alphavirus replicon particles (such as, for instance, VEE virus replicon particles) expressing only the Ebola virus GP protein. The GP protein, administered in the dosage, regimens and routes described below, has shown itself to be particularly successful as a protective composition.

An additional embodiment includes vaccines against infection by Ebola, comprising virus replicon particles (preferably VEE virus replicon particles) expressing the Ebola virus GP, NP, VP24, VP30, VP35, or VP40 proteins, or any combination of different VEE virus replicons each expressing one or more different Ebola proteins selected from GP, NP, VP24, VP30, VP35 and VP40—and preferably the vaccine includes replicons expressing each of the six proteins, in the form of a "cocktail" vaccine. For instance, in a preferred embodiment the Ebola VRPs contain one or more of the peptides specified by SEQ ID NOs: 24-53. In a related embodiment, the vaccine may include at a minimum at least one of the Ebola proteins selected from GP, NP, VP24, VP30, VP35 and VP40. In a preferred embodiment, the vaccine may include one or more of SEQ ID NOs: 24-53.

The invention also contemplates methods for inducing in a mammal a cytotoxic T lymphocyte response to the Ebola virus GP, NP, VP24, VP30, VP35, or VP40 proteins, or to a peptide comprising at least 6 amino acids thereof. In one version of the method, a recombinant DNA construct is administered to a mammal, such as, for example, a mouse, a guinea pig, a monkey or a human, which a recombinant DNA construct expresses the amino acid sequence of at least one of the Ebola virus GP, NP, VP24, VP30, VP35, or VP40 proteins (or a peptide comprising at least 6 amino acids thereof), under such conditions that a protective CTL response is induced in that mammal. In particular, the administered peptides may include one or more of SEQ ID NOs: 24-53. In another version of the method, one of the above-described immunogenic compositions is administered to the mammal, and preferably one that comprises virus replicon particles containing one of the Ebola virus GP, NP, VP24, VP30, VP35, or VP40 proteins (or a peptide comprising at least 6 amino acids thereof), or including one of the CTL epitopes set forth in SEQ ID NOs:24-53. In another version of the method, the amino acid sequence of at least one of the Ebola virus GP, NP, VP24, VP30, VP35, or VP40 proteins (or a peptide comprising at least 6 amino acids thereof) is administered to a mammal, such as, for example, a mouse, a guinea pig, a monkey or a human, under such conditions that a protective CTL response is induced in that mammal. In particular, the administered peptides may include one or more of SEQ ID NOs: 24-53.

In a preferred method, a recombinant DNA construct is administered to a mammal, which expresses the amino acid sequence of the Ebola virus GP protein (or a peptide comprising at least 6 amino acids thereof), under such conditions that a protective CTL response is induced in that mammal. In another version of the method, the immunogenic compositions comprises virus replicon particles containing GP protein (or a peptide comprising at least 6 amino acids thereof).

In another preferred method, a recombinant DNA construct is administered to a mammal, which expresses the amino acid sequences of the six Ebola virus GP, NP, VP24, VP30, VP35 and VP40 proteins (or a peptide comprising at least 6 amino acids of each of the proteins), under such conditions that a protective CTL response is induced in that mammal. In another version of the method, the immunogenic composition comprises virus replicon particles containing the six GP, NP, VP24, VP30, VP35 and VP40 proteins (or a peptide comprising at least 6 amino acids of each of the proteins).

Another embodiment of this invention entails methods for administering a vaccine of virus replicon particles (preferably VEE virus replicon particles) expressing the Ebola virus GP protein, or VEE virus replicons each expressing one of Ebola proteins GP, NP, VP24, VP30, VP35 and VP40, to form a six-protein vaccine. It is important that the vaccines should be administered at a dosage of not greater than $1\times10^8$ focus forming units (ffu) per inoculation per protein. A higher dosage, such as of $1\times10^7$ ffu, is not useful. The vaccines may be administered via intramuscularly injection, which is preferred and considered a novel feature of our invention. However, subcutaneous injection is also effective as long as the dosage is $1\times10^8$ ffu or lower, per inoculation. Therefore, for the GP-only vaccine, the dosage is $1\times10^8$ focus forming units (ffu) or lower. For the six-peptide cocktail, the dosage is $1\times10^8$ ffu or lower, per inoculation, per peptide—with a total dosage of $6\times10^8$ ffu or lower. Dosage regimen can also be important, and the preferred inoculation schedule is: Day 0, one month, four months, and twelve months.

BRIEF DESCRIPTION OF THE DRAWINGS

These and other features, aspects, and advantages of the present invention will become better understood with reference to the following description and appended claims, and accompanying drawings where:

FIG. 1 is a schematic description of the organization of the Ebola virus genome.

Figure 2A:
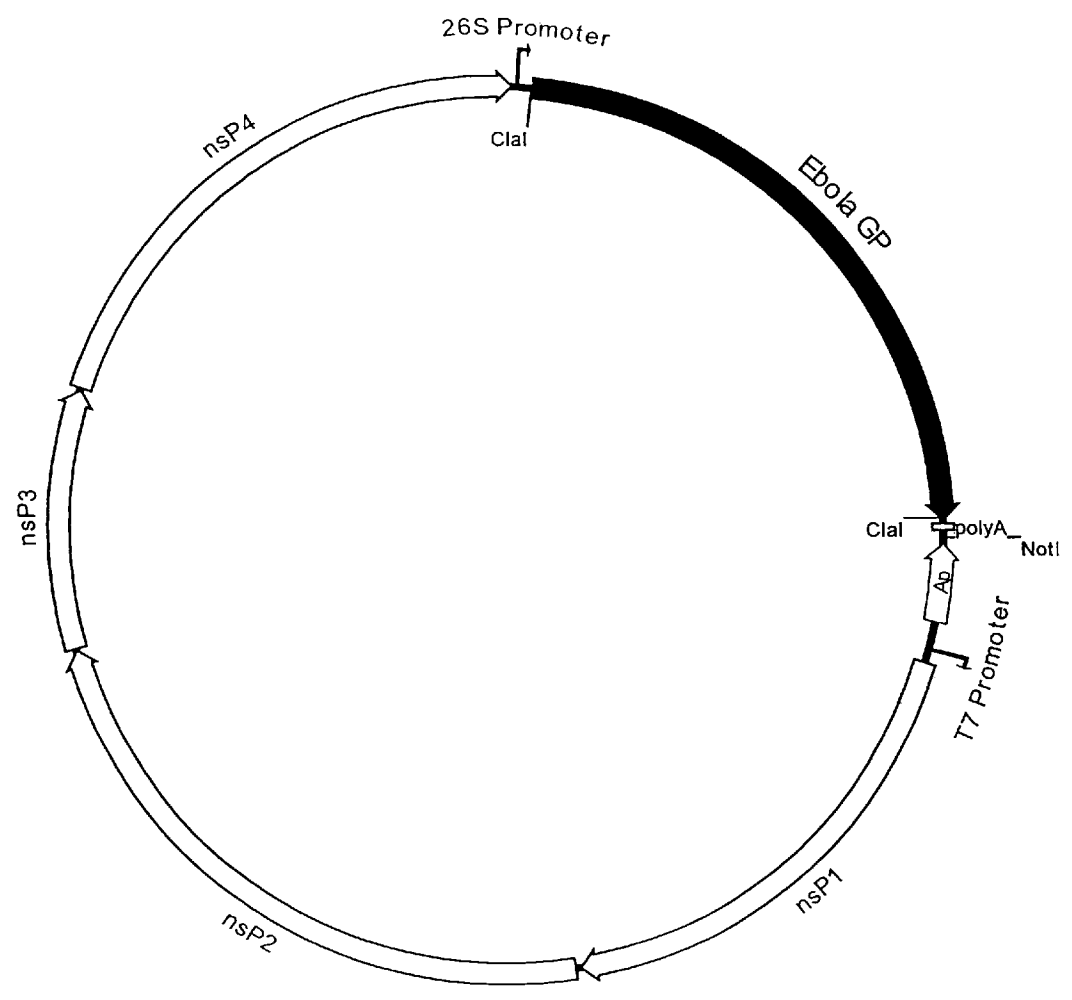
Figure 2B:
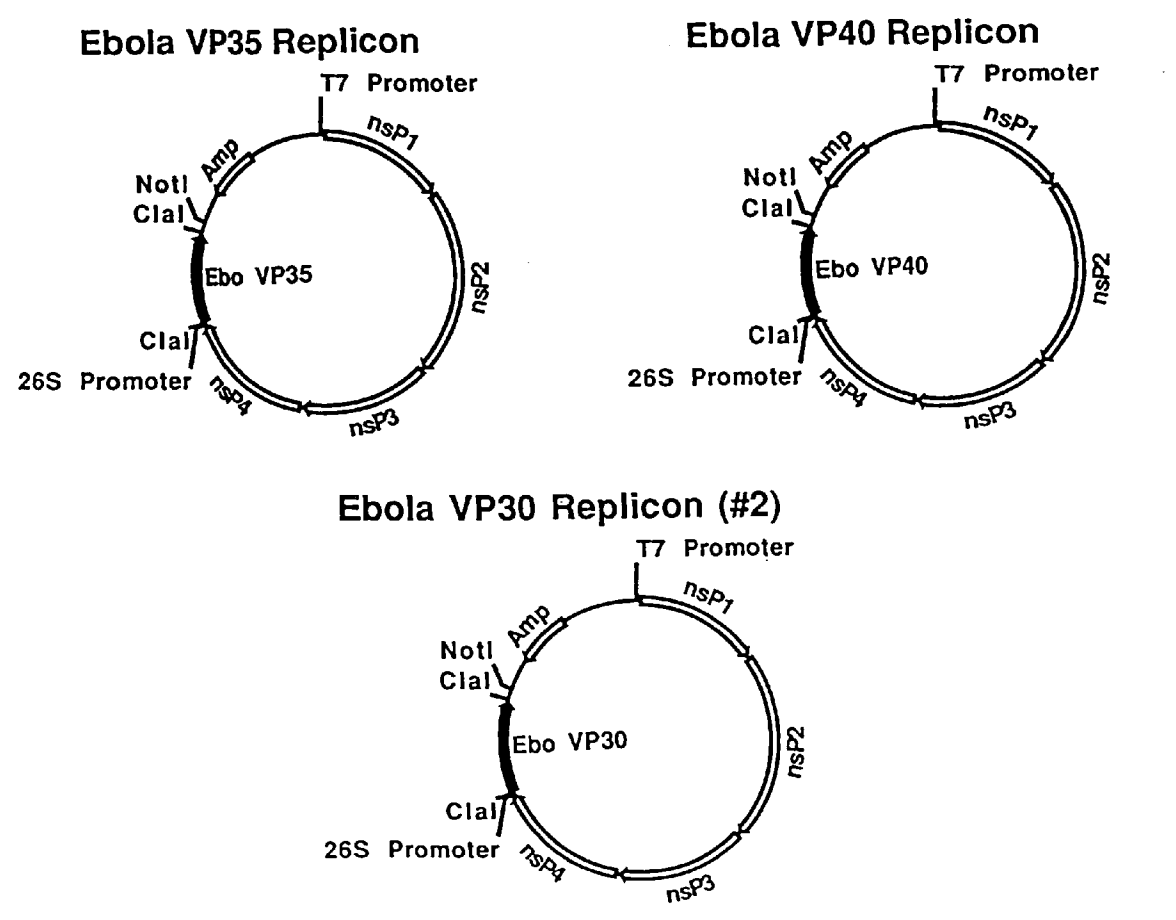

FIGS. 2A, 2B and 2C are schematic representations of the VEE replicon constructs containing Ebola genes.

FIG. 4 is an immunoprecipitation of Ebola proteins produced from replicon constructs.

DETAILED DESCRIPTION

Figure 2C:
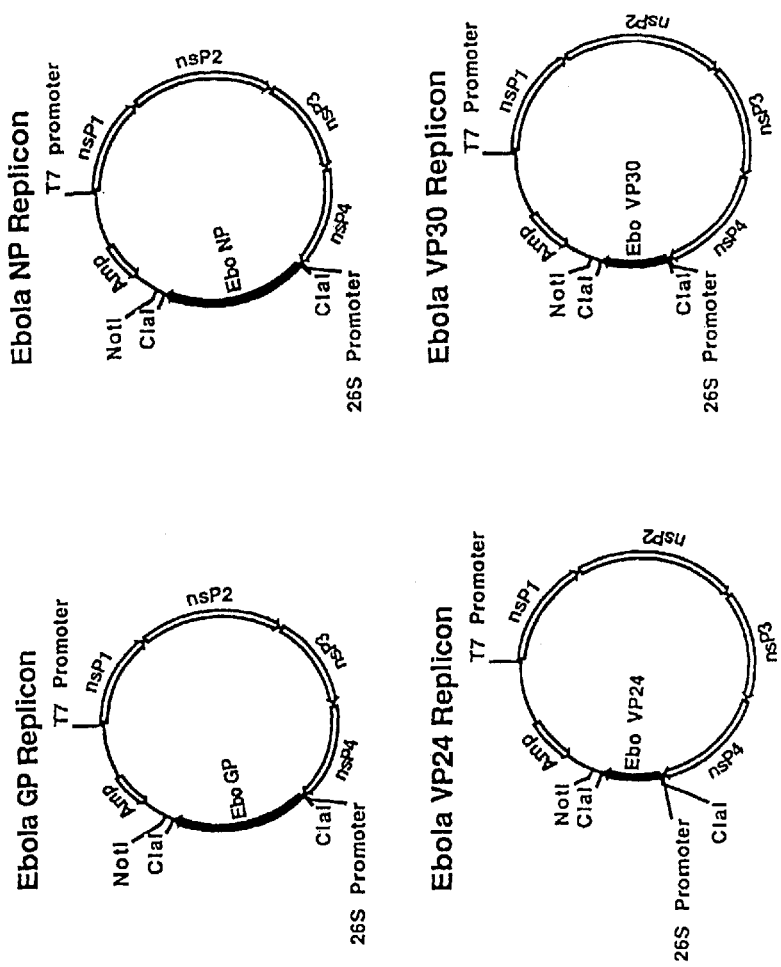

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses (e.g. Ebola Zaire 1976) cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection in humans. The virions of filoviruses contain seven proteins: a membrane-anchored glycoprotein (GP), a nucleoprotein (NP), an RNA-dependent RNA polymerase (L), and four virion structural proteins (VP24, VP30, VP35, and VP40). Little is known about the biological functions of these proteins and it is not known which antigens significantly contribute to protection and should therefore be used in an eventual vaccine candidate.

Replicon. A replicon is equivalent to a full-length virus from which all of the viral structural proteins have been deleted. A multiple cloning site can be inserted downstream of the 26S promoter into the site previously occupied by the structural protein genes. Virtually any heterologous-gene may be inserted into this cloning site. The RNA that is transcribed from the replicon is capable of replicating and expressing viral proteins in a manner that is similar to that seen with the full-length infectious virus clone. However, in lieu of the viral structural proteins, the heterologous antigen is expressed from the 26S promoter in the replicon. This system does not yield any progeny virus particles because there are no viral structural proteins available to package the RNA into particles.

Particles which appear structurally identical to virus particles can be produced by supplying structural protein RNAs in trans for packaging of the replicon RNA. This is typically done with two defective helper RNAs which encode the structural proteins. One helper consists of a full length infectious clone from which the nonstructural protein genes and the glycoprotein genes are deleted. This helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNAs are transcribed in vitro and are co-transfected with replicon RNA. Because the replicon RNA retains the sequences for packaging by the nucleocapsid protein, and because the helpers lack these sequences, only the replicon RNA is packaged by the viral structural proteins. The packaged replicon particles are released from the host cell and can then be purified and inoculated into animals. The packaged replicon particles will have a tropism similar to the parent virus. The packaged replicon particles will infect cells and initiate a single round of replication, resulting in the expression of only the virus nonstructural proteins and the product of the heterologous gene that was cloned in the place of the virus structural proteins. In the absence of RNA encoding the virus structural proteins, no progeny virus particles can be produced from the cells infected by packaged replicon particles.

Any alphavirus replicon may be effective in this invention, as long as it has the ability to produce the desired protein or peptide in a manner that induces protective B and T cells in vivo in mammals to which it is administered to (such as, for instance, eastern equine encephalitis, western equine encephalitis, Semlike forest, Sindbis and Venezualen Equine Encephalitis).

The VEE virus replicon (Vrep) is a preferred vector system. The Vrep is a genetically reorganized version of the VEE virus genome in which the structural protein genes are replaced with a gene from an immunogen of interest, such as the Ebola virus virion proteins. This replicon can be transcribed to produce a self-replicating RNA that can be packaged into infectious particles using defective helper RNAs that encode the glycoprotein and capsid proteins of the VEE virus. Since the packaged replicons do not encode the structural proteins, they are incapable of spreading to new cells and therefore undergo a single abortive round of replication in which large amounts of the inserted immunogen are made in the infected cells. The VEE virus replicon system is described in U.S. Patent to Johnston et al., U.S. Pat. No. 5,792,462 issued on Aug. 11, 1998.

Subject. Includes human, animal, e.g., horse, donkey, pig, mouse, hamster, monkey, chicken, and insect such as mosquito.

In one embodiment, the present invention relates to DNA fragments which encode any of the Ebola Zaire 1976 (Maying a isolate) GP, NP, VP24, VP30, VP35, and VP40 proteins. The GP and NP genes of Ebola Zaire were previously sequenced by Sanchez et al. (1993, supra) and have been deposited in GenBank (accession number L11365). A plasmid encoding the VEE replicon vector containing a unique ClaI site downstream from the 26S promoter was described previously (Davis, N. L. et al., (1996) *J. Virol.* 70, 3781-3787; Pushko, P. et al. (1997) *Virology* 239, 389-401). The Ebola GP and NP genes from the Ebola Zaire 1976 virus were derived from PS64— and PGEM3ZF(−)-based plasmids (Sanchez, A. et al. (1989) *Virology* 170, 81-91; Sanchez, A. et al. (1993) Virus Res. 29, 215-240). From these plasmids, the BamHI-EcoRI (2.3 kb) and BamHI-KpnI (2.4 kb) fragments containing the NP and GP genes, respectively, were subcloned into a shuttle vector that had been digested with BamHI and EcoRI (Davis et al. (1996) supra; Grieder, F. B. et al. (1995) *Virology* 206, 994-1006). For cloning of the GP gene, overhanging ends produced by KpnI (in the GP fragment) and EcoRI (in the shuttle vector) were made blunt by incubation with T4 DNA polymerase according to methods known in the art. From the shuttle vector, GP or NP genes were subcloned as ClaI-fragments into the ClaI site of the replicon clone, resulting in plasmids encoding the GP or NP genes in place of the VEE structural protein genes downstream from the VEE 26S promoter.

The VP genes of Ebola Zaire were previously sequenced by Sanchez et al. (1993, supra) and have been deposited in GenBank (accession number L11365). The VP genes of Ebola used in the present invention were cloned by reverse transcription of RNA from Ebola-infected Vero E6 cells and subsequent amplification of viral cDNAs using the polymerase chain reaction. First strand synthesis was primed with oligo dT (Life Technologies). Second strand synthesis and subsequent amplification of viral cDNAs were performed with gene-specific primers (SEQ ID NOS:8-16). The primer sequences were derived from the GenBank deposited sequences and were designed to contain a ClaI restriction site for cloning the amplified VP genes into the ClaI site of the replicon vector. The letters and numbers in bold print indicate Ebola gene sequences in the primers and the corresponding location numbers based on the GenBank deposited sequences.

VP24: (1) forward primer is 5'-GGGATCGATCTCCAGA-CACCAAGCAAGACC-3' (SEQ ID NO: 8)
(10,311-10,331)
(2) reverse primer is 5'-GGGATCGATGAGTCAG-CATATATGAGTTAGCTC-3' (SEQ ID NO:9)
(11,122-11,145)

VP30: (1) forward primer is 5'-CCCATCGATCAGATCT-GCGAACCGGTAGAG-3' SEQ ID NO:10)
(8408-8430)
(2) reverse primer is 5'-CCCATCGATGTACCCTCATCA-GACCATGAGC-3' (SEQ ID NO:11)
(9347-9368)

VP35: (1) forward primer is 5'-GGGATCGATA-GAAAAGCTGGTCTAACAAGATGA-3' (SEQ ID NO:12)
(3110-3133)
(2) reverse primer is 5'-CCCATCGATCTCACAAGTG-TATCATTAATGTAACGT-3' (SEQ ID NO:13) (4218-4244)

VP40: (1) forward primer is 5'-CCCATCGATCCTAC-CTCGGCTGAGAGAGTG-3' (SEQ ID NO: 14)
(4408-4428)
(2) reverse primer is 5'-CCCATCGATATGTTATGCAC-TATCCCTGAGAAG-3' (SEQ ID NO:15)
(5495-5518)

VP30 #2:
(1) forward primer as for VP30 above
(2) reverse primer is 5'-CCCATCGATCTGTTAGGGT-TGTATCATACC-3' (SEQ ID NO: 16)

The Ebola virus genes cloned into the VEE replicon were sequenced. Changes in the DNA sequence relative to the sequence published by Sanchez et al. (1993) are described relative to the nucleotide (nt) sequence number from GenBank (accession number L11365).

The nucleotide sequence we obtained for Ebola virus GP (SEQ ID NO:1) differed from the GenBank sequence by a transition from A to G at nt 8023. This resulted in a change in the amino acid sequence from Ile to Val at position 662 (SEQ ID NO: 17).

The nucleotide sequence we obtained for Ebola virus NP (SEQ ID NO:2) differed from the GenBank sequence at the following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The Ebola virus VP24 nucleotide sequence (SEQ ID NO:3) differed from the GenBank sequence at 6 positions, resulting in 3 nonconservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

Two different sequences for the Ebola virus VP30 gene, VP30 and VP30#2 (SEQ ID NOS: 4 and 7) are included. Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS: 20 and 23). As a result, the C-terminus of the VP30 protein differs significantly from that previously reported. In addition to these 2 changes, the VP30#2 nucleic acid in SEQ ID NO:7 contains a conservative transition from T to C at nt 9217. Because the primers originally used to clone the VP30 gene into the replicon were designed based on the GenBank sequence, the first clone that we constructed (SEQ ID NO: 4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO: 23) did not inhibit the ability of the protein to serve as a protective antigen in BALB/c mice. We have also determined that a VEE replicon construct, which contains the authentic C-terminus of VP30 (VP30#2, SEQ ID NO: 23), protects mice against a lethal Ebola challenge.

The nucleotide sequence for Ebola virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO: 21). The insertion of the T residue resulted in a change in the open reading frame of VP35 from that previously reported by Sanchez et al. (1993) following amino acid number 324. As a result, Ebola virus VP35 encodes a protein of 340 amino acids, where amino acids 325 to 340 (SEQ ID NO: 21) differ from and replace the C-terminal 27 amino acids of the previously published sequence.

Sequencing of VP30 and VP35 was also performed on RT/PCR products from RNA derived from cells that were infected with Ebola virus 1976, Ebola virus 1995 or the mouse-adapted Ebola virus. The changes noted above for the Vrep constructs were also found in these Ebola viruses. Thus, we believe that these changes are real events and not artifacts of cloning.

The Ebola virus VP40 nucleotide sequence (SEQ ID NO:6) differed from the GenBank sequence by a transversion from a C to G at nt 4451 and a transition from a G to A at nt 5081. These sequence changes did not alter the protein sequence of VP40 (SEQ ID NO: 22) from that of the published sequence.

Each of the Ebola virus genes were individually inserted into a VEE virus replicon vector. The VP24, VP30, VP35, and VP40 genes of Ebola Zaire 1976 (Maying a isolate) were cloned by reverse transcription of RNA from Ebola-infected Vero E6 cells and viral cDNAs were amplified using the polymerase chain reaction. The Ebola Zaire 1976 (Maying a isolate) GP and NP genes were obtained from plasmids already containing these genes (Sanchez, A. et al., (1989) *Virology* 170, 81-91; Sanchez, A. et al., (1993) *Virus Res.* 29, 215-240) and were subcloned into the VEE replicon vector.

After characterization of the Ebola gene products expressed from the VEE replicon constructs in cell culture, these constructs were packaged into infectious VEE virus replicon particles (VRPs) and subcutaneously injected into BALB/c and C57BL/6 mice. As controls in these experiments, mice were also immunized with a VEE replicon expressing Lassa nucleoprotein (NP) as an irrelevant control antigen, or injected with PBS buffer alone. The results of this study demonstrate that VRPs expressing the Ebola GP, NP, VP24, VP30, VP35 or VP40 genes induced protection in mice and may reasonably to expected to provide protection in humans.

DNA or polynucleotide sequences to which the invention also relates include sequences of at least about 6 nucleotides, preferably at least about 8 nucleotides, more preferably at least about 10-12 nucleotides, most preferably at least about 15-20 nucleotides corresponding, i.e., homologous to or complementary to, a region of the Ebola nucleotide sequences described above. Preferably, the sequence of the region from which the polynucleotide is derived is homologous to or complementary to a sequence which is unique to the Ebola genes. Whether or not a sequence is unique to the Ebola gene can be determined by techniques known to those of skill in the art. For example, the sequence can be compared to sequences in databanks, e.g., GenBank and compared by DNA:DNA hybridization. Regions from which typical DNA sequences may be derived include but are not limited to, for example, regions encoding specific epitopes, as well as non-transcribed and/or non-translated regions.

The derived polynucleotide is not necessarily physically derived from the nucleotide sequences shown in SEQ ID NO: 1-7, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays, for example, for the discovery of other Ebola sequences.

In another embodiment, the present invention relates to a recombinant DNA molecule that includes a vector and a DNA sequence as described above. The vector can take the form of a plasmid, a eukaryotic expression vector such as pcDNA3.1, pRcCMV2, pZeoSV2, or pCDM8, which are available from Invitrogen, or a virus vector such as baculovirus vectors, retrovirus vectors or adenovirus vectors, alphavirus vectors, and others known in the art.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of the desired coding sequences when appropriate control sequences which are compatible with the designated host are used.

Among prokaryotic hosts, *E. coli* is the most frequently used host cell for expression. General control sequences for prokaryotes include promoters and ribosome binding sites. Transfer vectors compatible with prokaryotic hosts are commonly derived from a plasmid containing genes conferring ampicillin and tetracycline resistance (for example, pBR322) or from the various pUC vectors, which also contain sequences conferring antibiotic resistance. These antibiotic resistance genes may be used to obtain successful transformants by selection on medium containing the appropriate antibiotics. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to sequences encoding an IgG molecule, an adjuvant, a carrier, or an agent for aid in purification of Ebola proteins, such as glutathione S-transferase.

In addition, the Ebola virus gene products can also be expressed in eukaryotic host cells such as yeast cells and mammalian cells. *Saccharomyces cerevisiae, Saccharomyces carlsbergensis*, and *Pichia pastoris* are the most commonly used yeast hosts. Control sequences for yeast vectors are known in the art. Mammalian cell lines available as hosts for expression of cloned genes are known in the art and include many immortalized cell lines available from the American Type Culture Collection (ATCC), such as CHO cells, Vero cells, baby hamster kidney (BHK) cells and COS cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences, poly A addition sequences, enhancer sequences which increase expression, or sequences which cause amplification of the gene. These sequences are known in the art.

The transformed or transfected host cells can be used as a source of DNA sequences described above. When the recombinant molecule takes the form of an expression system, the transformed or transfected cells can be used as a source of the protein described below.

In another embodiment, the present invention relates to Ebola virion proteins such as GP having an amino acid sequence corresponding to SEQ ID NO:17 encompassing 676 amino acids, NP, having an amino acid sequence corresponding to SEQ ID NO: 18 encompassing 739 amino acids, VP24, having an amino acid sequence corresponding to SEQ ID NO: 19 encompassing 251 amino acids, VP30, having an amino acid sequence corresponding SEQ ID NO:20 encompassing 324 amino acids, VP35, having an amino acid sequence corresponding to SEQ ID NO:21 encompassing 340 amino acids, and VP40, having an amino acid sequence corresponding to SEQ ID NO:22, encompassing 326 amino acids, and VP30#2, having an amino acid sequence corresponding to SEQ ID NO:23 encompassing 288 amino acids, or any allelic variation of these amino acid sequences. By allelic variation is meant a natural or synthetic change in one or more amino acids which occurs between different serotypes or strains of Ebola virus and does not affect the antigenic properties of the protein. There are different strains of Ebola (Zaire 1976, Zaire 1995, Reston, Sudan, and Ivory Coast). The NP and VP genes of all these different viruses have not been sequenced. It would be expected that these proteins would have homology among different strains and that vaccination against one Ebola virus strain might afford cross protection to other Ebola virus strains.

A polypeptide or amino acid sequence derived from any of the amino acid sequences in SEQ ID NO:17, 18, 19, 20, 21, 22, and 23 refers to a polypeptide having an amino acid sequence identical to that of a polypeptide encoded in the sequence, or a portion thereof wherein the portion consists of at least 2-5 amino acids, preferably at least 8-10 amino acids, and more preferably at least 11-15 amino acids, or which is immunologically identifiable with a polypeptide encoded in the sequence.

A recombinant or derived polypeptide is not necessarily translated from a designated nucleic acid sequence, or the DNA sequence found in GenBank accession number L11365. It may be generated in any manner, including for example, chemical synthesis, or expression from a recombinant expression system.

When the DNA or RNA sequences described above are in a replicon expression system, such as the VEE replicon described above, the proteins can be expressed in vivo. The DNA sequence for any of the GP, NP, VP24, VP30, VP35, and VP40 virion proteins can be cloned into the multiple cloning site of a replicon such that transcription of the RNA from the replicon yields an infectious RNA encoding the Ebola protein or proteins of interest (see FIGS. 2A, 2B and 2C). The replicon constructs include Ebola virus GP (SEQ ID NO: 1) cloned into a VEE replicon (VRepEboGP), Ebola virus NP (SEQ ID NO:2) cloned into a VEE replicon (VRepEboNP), Ebola virus VP24 (SEQ ID NO:3) cloned into a VEE replicon (VRepEboVP24), Ebola virus VP30 (SEQ ID NO:4) or VP30#2 (SEQ ID NO:7) cloned into a VEE replicon (VRepEboVP30 or VRepEboVP30(#2)), Ebola virus VP35 (SEQ ID NO:5) cloned into a VEE replicon (VRepEboVP35), and Ebola virus VP40 (SEQ ID NO:6) cloned into a VEE replicon (VRepEboVP40). The replicon DNA or RNA can be used as a vaccine for inducing protection against infection with Ebola.

Figure 3:
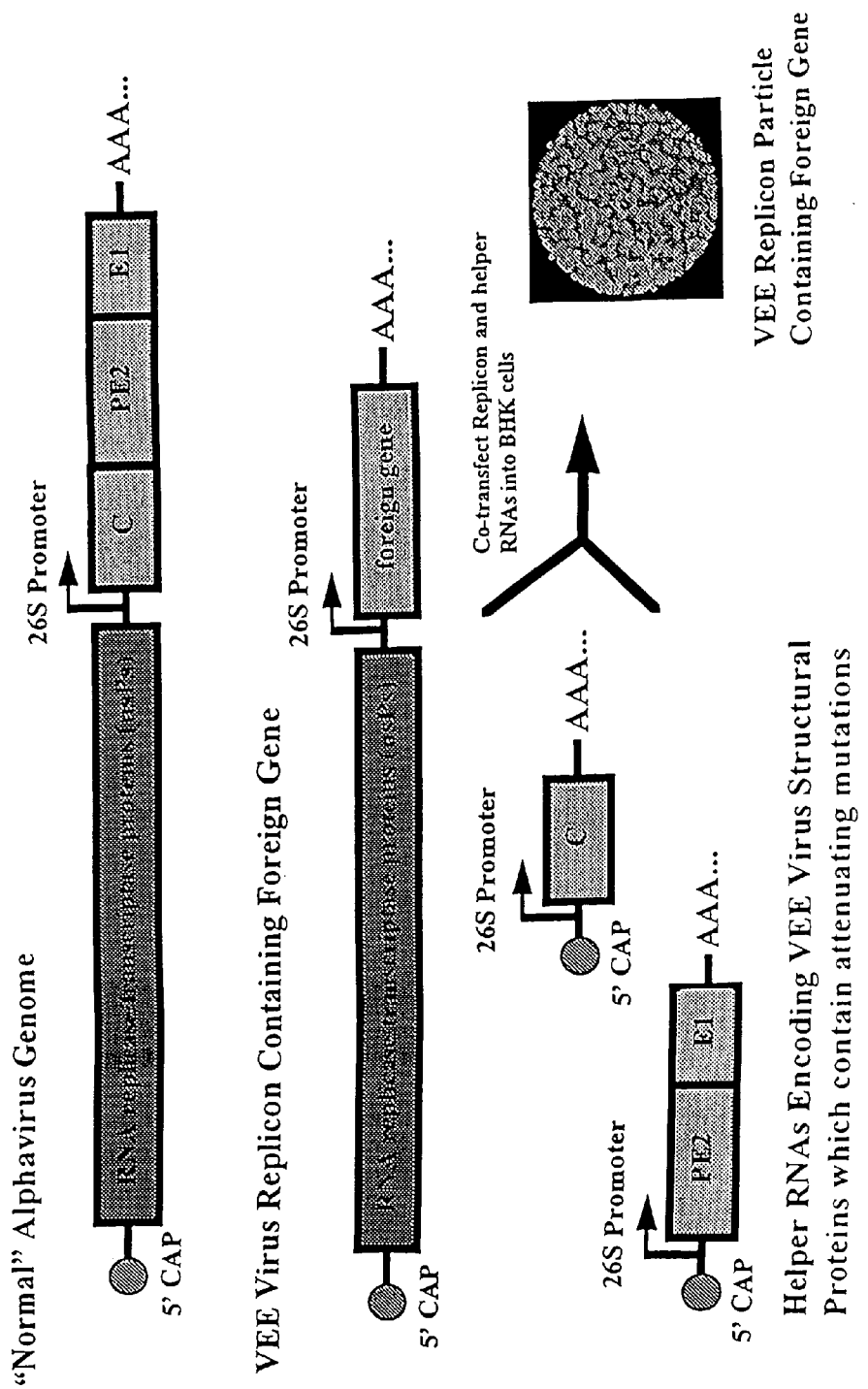
FIG. 3 shows the generation of VEE viral-like particles containing Ebola genes.

Use of helper RNAs containing sequences necessary for packaging of the viral replicon transcripts will result in the production of virus-like particles containing replicon RNAs (FIG. 3). These packaged replicons will infect host cells and initiate a single round of replication resulting in the expression of the Ebola proteins in the infected cells. The packaged replicon constructs (i.e. VEE virus replicon particles, VRP) include those that express Ebola virus GP (EboGPVRP), Ebola virus NP (EboNPVRP), Ebola virus VP24 (EboVP24VRP), Ebola virus VP30 (EboVP30VRP or EboVP30VRP(#2)), Ebola virus VP35 (EboVP35VRP), and Ebola virus VP40 (EboVP40VRP).

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology*. Frederick M. Ausubel et al. (eds.), John Wiley and Sons, Inc. The RNA molecules can be used, for example, as a direct RNA vaccine, or to transfect cells along with RNA from helper plasmids, one of which expresses VEE glycoproteins and the other VEE capsid proteins, as described above, in order to obtain replicon particles.

In a further embodiment, the present invention relates to a method of producing the recombinant or fusion protein which includes culturing the above-described host cells under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with Ebola or as a diagnostic tool for detection of Ebola infection.

In another embodiment, the present invention relates to antibodies specific for the above-described recombinant proteins (or polypeptides). For instance, an antibody can be raised against a peptide having the amino acid sequence of any of SEQ ID NO:17-25, or against a portion thereof of at least 10 amino acids, preferably, 11-15 amino acids. Persons with ordinary skill in the art using standard methodology can raise monoclonal and polyclonal antibodies to the protein (or polypeptide) of the present invention, or a unique portion thereof.

Materials and Methods for producing antibodies are well known in the art (see for example Goding, *In Monoclonal Antibodies: Principles and Practice*, Chapter 4, 1986).

In another embodiment, the present invention relates to an Ebola vaccine comprising VRPs that express one or more of the Ebola proteins described above. The vaccine is administered to a subject wherein the replicon is able to initiate one round of replication producing the Ebola proteins to which a protective immune response is initiated in said subject.

One particularly effective vaccine comprises virus replicon particles expressing the GP Ebola peptide. Preferably the GP Ebola peptide has the sequence specified in SEQ ID NO:29, or a peptide fragment comprising at least 9 consecutive amino acids. For instance, the peptide fragment may has the sequence of YFGPAAEGI (SEQ ID NO:42).

Another particularly effective vaccine comprises virus replicon particles expressing the Ebola peptides GP, NP, VP24, VP30, VP35, and VP40, in an effective immunogenic amount, in a pharmaceutically acceptable and/or adjuvant. Thus, this vaccine contains all six of the Ebola peptides. The virus replicon particles are preferably produced from a replicon vector selected from the group consisting of Venezuelan Equine Encephalitis (VEE) virus, eastern equine encephalitis, western equine encephalitis, Semliki forest and Sindbis. Preferably, the GP peptide has the sequence specified in SEQ ID NO:29, or a peptide fragment comprising at least 9 consecutive amino acids; the NP peptide has the sequence specified in SEQ ID NO:24, SEQ ID NO:26, SEQ ID NO:27 or SEQ ID NO:28, or a peptide fragment comprising at least 9 consecutive amino acids; the VP24 peptide has the sequence specified in SEQ ID NO:25, SEQ ID NO:30, or SEQ ID NO:31, or a peptide fragment comprising at least 9 consecutive amino acids; the VP30 peptide has the sequence specified in SEQ ID NO:32 or SEQ:ID NO:33, or a peptide fragment comprising at least 9 consecutive amino acids; the VP35 peptide has the sequence specified in SEQ ID NO:34, SEQ ID NO:35 or SEQ ID NO:36, or a peptide fragment comprising at least 9 consecutive amino acids; and the VP40 peptide has the sequence specified in SEQ ID NO:37, SEQ ID NO:38, SEQ ID NO:39, SEQ ID NO:40, or SEQ ID NO:41, or a peptide fragment comprising at least 9 consecutive amino acids. The GP peptide fragment may the sequence of YFG-PAAEGI (SEQ ID NO:42); the VP24 peptide fragment may have the sequence of KFINKLDAL, (SEQ ID NO:43), NYN-GLLSSI (SEQ ID NO:44), or PGPAKFSLL (SEQ ID NO:45); the VP30 peptide fragment may have the sequence of LSLLCETHLR (SEQ ID NO:46) or MFITAFLNI (SEQ ID NO:47); and the VP40 peptide fragment may have the sequence of EFVLPPVQL (SEQ ID NO:48), FLVPPV (SEQ ID NO:49), QYFTFDLTALK (SEQ ID NO:50), TSPEKIQAI (SEQ ID NO:51), RIGNQAFL (SEQ ID NO:52) or QAFLQEFV (SEQ ID NO:53).

The method of administering the vaccine is also a novel aspect of our invention. For the GP-alone vaccine, a mammal, including a human, may be injected subcutaneously or preferably intramuscularly with a composition comprising virus replicon particles expressing the GP Ebola peptide, in a dosage not greater than $1 \times 10^8$ focus forming units. For the six-protein vaccine, a mammal, including a human, may be injected subcutaneously or preferably intramuscularly with a composition comprising virus replicon particles expressing the GP Ebola peptide, in a dosage not greater than $1 \times 10^8$ focus forming units per inoculation per peptide—with a total dosage of $6 \times 10^8$ focus forming units. Injections are preferably repeated as needed or desired for maximum immuno-protection, such as at one month, four months, and twelve months.

It is likely that the protection afforded by these genes is due to both the humoral (antibodies (Abs)) and cellular (cytotoxic T cells (CTLs)) arms of the immune system. Protective immunity induced to a specific protein may comprise humoral immunity, cellular immunity, or both. The only Ebola virus protein known to be on the outside of the virion is the GP. The presence of GP on the virion surface makes it a likely target for GP-specific Abs that may bind either extracellular virions or infected cells expressing GP on their surfaces. Serum transfer studies in this invention demonstrate that Abs that recognize GP protect mice against lethal Ebola virus challenge.

In contrast, transfer of Abs specific for NP, VP24, VP30, VP35, or VP40 did not protect mice against lethal Ebola challenge. This data, together with the fact that these are internal virion proteins that are not readily accessible to Abs on either extracellular virions or the surface of infected cells, suggest that the protection induced in mice by these proteins is mediated by CTLs.

CTLs can bind to and lyse virally infected cells. This process begins when the proteins produced by cells are routinely digested into peptides. Some of these peptides are bound by the class I or class II molecules of the major histocompatability complex (MHC), which are then transported to the cell surface. During virus infections, viral proteins produced within infected cells also undergo this process. CTLs that have receptors that bind to both a specific peptide and the MHC molecule holding the peptide lyse the peptide-bearing cell, thereby limiting virus replication. Thus, CTLs are characterized as being specific for a particular peptide and restricted to a class I or class II MHC molecule.

CTLs may be induced against any of the Ebola virus proteins, as all of the viral proteins are produced and digested within the infected cell. Thus, protection to Ebola virus involves CTLs against GP, NP, VP24, VP30, VP35, and/or VP40. It is especially noteworthy that the VP proteins varied in their protective efficacy when tested in genetically inbred mice that differ at the MHC locus. This, together with the inability to demonstrate a role for Abs in protection induced by the VP proteins and the data in Table A below, demonstrates a role for CTLs. Thus, in this invention a vaccine may include several Ebola virus proteins (e.g., at least two), or several CTL epitopes (e.g., at least two), capable of inducing broad protection to different Ebola viruses in outbred populations (e.g. people). To that end, the inventors have identified 18 sequences recognized by CTLs, as determined initially by measuring gamma interferon production by intracellular cytokine staining and gamma interferon secretion by the ELISpot assay. The ability to lyse cells was measured in chromium release assays and protection was evaluated by adoptive transfer of cells into Ebola-naïve mice. Where sequence information is available, the conservation of these CTL epitopes in other Ebola viruses is noted in Table A. Conserved sequences should be capable of inducing protective CTLs to each of the viruses in which the sequence is present.

The identified CTL epitopes are:

Ebola virus NP SEQ ID NO:24, SEQ ID NO:26, SEQ ID NO:27, and SEQ ID NO:28;

Ebola virus GP SEQ ID NO:29 (encompassing YFG-PAAEGI, SEQ ID NO:42);

Ebola virus VP24 SEQ ID NO:460 (encompassing KFIN-KLDAL, SEQ ID NO:43), SEQ ID NO:30 (encompassing NYNGLLSSI, SEQ ID NO:44), and SEQ ID NO:31 (encompassing PGPAKFSLL, SEQ ID NO:45);

Ebola virus VP30 SEQ ID NO:32 (encompassing LSLLCETHLR, SEQ ID NO:46), and SEQ ID NO:33 (encompassing MFITAFLNI, SEQ ID NO:47);

Ebola virus VP35 SEQ ID NO:34, SEQ ID NO:35, and SEQ ID NO:36; and

Ebola virus VP40 SEQ ID NO:37 (encompassing EFVLP-PVQL, SEQ ID NO:48), SEQ ID NO:38 (encompassing FLVPPV, SEQ ID NO:49 and QYFTFDLTALK, SEQ ID NO:50), SEQ ID NO:39 (encompassing TSPEKIQAI, SEQ ID NO:51); SEQ ID NO:40 (encompassing RIGNQAFL, SEQ ID NO:52), and SEQ ID NO:41 (encompassing QAFLQEFV, SEQ ID NO:53).

See Table A below.

Testing to identify the role of CTLs in protection was performed by obtaining CTLs from mice, expanding them in vitro, and transferring the cells into an unvaccinated mouse of the same genetic background. Several hours later, the recipient mice were challenged with 10-1000 pfu of mouse-adapted Ebola virus. They were observed for signs of illness for 28 days. Control animals received no cells or cells that were not specific for Ebola virus. Testing of the cells in vitro indicated that they were CD8+, a marker indicating class I-restriction. The inventors were able to demonstrate that CTLs to these sequences protected at least 80% of recipient mice from challenge. In all of our examples, the ability to lyse peptide-pulsed target cells has predicted protection in mice receiving those cells.

TABLE A

Ebola Virus Epitopes Recognized by Murine CD8+ T cells

| Protein[a] | Epitope[b] | % INF-γ ICC[c] | INF-γ ELISpot[d] | $^{51}$Cr[e] | Protective[f] | Restriction[g] | Conserved Strains[h] |
|---|---|---|---|---|---|---|---|
| GP | WIP<u>YFGPAAEGIY</u>TE (SEQ ID 29) | 0.40/0.08 | Y | Neg | IP | H-2$^b$ | R,G |
| NP | VYQVNNLEEIC (SEQ ID 24) | 1.06/0.11 | Y | 55.6 | Yes | H-2$^b$ | G |
|  | GQFLFASL (SEQ ID 26) | 0.88/0.11 | Y | 45 | Yes | H-2$^b$ | S,G |
|  | DAVLYYHMM (SEQ ID 27) | 0.99/0.11 | Y | 40.6 | Yes | H-2$^b$ | G |
|  | SFKAALSSL (SEQ ID 28) | 0.63/0.04 | Y | 38.8 | Yes | H-2$^d$ |  |
| VP24 | NIL<u>KFINKLDALH</u>VV (SEQ ID 461) | 0.52/0.09 | Y | 45.9 | Yes | H-2$^d$ | G |
|  | NYNGLL<u>SSIEGTQN</u> (SEQ ID 30) | 0.38/0.09 | Y | 50.6 | Yes | H-2$^d$ | R,G |
|  | RMK<u>PGPAKFSLL</u>HESTLKAFTQGSS (SEQ ID 31) | 3.34/0.09 | Y | 43.2 | Yes* | H-2$^d$ | R,G |
| VP30 | FSKS<u>QLSLLCETHL</u>R (SEQ ID 32) | 0.45/0.15 | N | 47.3 | Yes* | H-2$^b$ |  |
|  | DLQS<u>LIMFITAFLNI</u> (SEQ ID 33) | 0.7/0.15 | N | ND | Yes* | H-2$^b$ |  |
| VP35 | RNIMYDHL (SEQ ID 34) | 1.53/0.22 | Y | 87.4 | Yes | H-2$^b$ |  |
|  | MVAKYDLL (SEQ ID 35) | 1.63/0.22 | N | 78.9 | Yes | H-2$^b$ | R |
|  | CDIENNPGL (SEQ ID 36) | 1.99/0.15 | N | 80.4 | Yes | H-2$^b$ |  |
| VP40 | AFL<u>QEFVLPPVQL</u>PQ (SEQ ID 37) | 0.45/0.22 | ND | ND | IP | H-2$^d$ |  |
|  | FVLPPVQLPQYFTFDLTALK (SEQ ID 38) | 0.41/0.22 | ND | 38 | Yes* | H-2$^d$ |  |
|  | KSGKKGNSADL<u>TSPEKIQAI</u>MTSLQDFKIV (SEQ ID 39) | 0.6/0.22 | N | 36.4 | IP | H-2$^d$ |  |
|  | PLRLL<u>RIGNQAFLQE</u> (SEQ ID 40) | 0.7/0.05 | N | 52.8 | Yes | H-2$^b$ |  |
|  | <u>RIGNQAFLQEFVLPP</u> (SEQ ID 41) | 0.38/0.05 | N | 46.7 | IP | H-2$^b$ |  |

[a]Proteins are from Ebola Zaire '76 virus: GP, glycoprotein, NP, nucleoprotein, or the virion proteins VP24, VP30, VP35 or VP40.
[b]Epitope, indicates peptide sequence(s) tested in the T cell assays. Underlined regions are presumed minimum epitopes based on binding motifs, algorithm predictions and/or demonstrated effects based on synthesis of shorter peptides.
[c]ICC data is % of CD8 that are INF-γ positive and CD8 positive/background
[d]IFN-γ ELISpot assays indicated (Y, yes; N, no) presence of secreted interferon-γ.
[e]$^{51}$Cr data is specific lysis at the 25:1 E:T ratio.
[f]Protection observed in 100% of naïve mice receiving CTLs specific for the designated epitopes, except where marked with *, in which cases protection of 80-90% was observed. IP, in progress (data within 2 weeks).
[g]Restriction indicates the major histocompatability type for which lysis was observed. H-2$^b$ mice are C57Bl/6 and H-2$^d$ are Balb/c.
[h]Conserved strains: underlined sequences representing epitopes are identical in Sudan, Gabon and Reston Ebola viruses as indicated by S, G or R, respectively.
ND, not determined In another vaccine embodiment, the invention relates to a vaccine against Ebola infection including at least one of these CTL epitope sequences, and preferably at least one CTL epitope having the amino acid sequence of SEQ ID NOs:24-53. Preferably, the vaccine includes at least two of the CTL epitope sequences, more preferably at least three, more preferably at least four, more preferably at least five, and more preferably all of the sequences. As shown in the examples below, protection is increased as the number of CTL epitopes in the immunogenic composition or vaccine is increased, and also as the number of epitopes from different Ebola proteins is increased.

In another vaccine embodiment, the vaccine includes a CTL epitope sequence from at least two different proteins selected from the group consisting of GP, NP, VP24, VP30, VP35 and VP40. More preferably, the vaccine includes a CTL epitope sequence from at least three different proteins from that group, more preferably at least four, more preferably at least five, and most preferably includes at least one CTL epitope sequence from each of the six proteins. The CTL epitopes may have the amino acid sequences as set forth in SEQ ID NOs:24-53. It is noted that administering the GP peptide alone may prevent the induction of protective antibodies, which may be undesirable.

In another vaccine embodiment, the vaccine may include at a minimum at least one of the Ebola proteins selected from GP, NP, VP24, VP30, VP35 and VP40, but preferably contains at least two, more preferably at least three, more preferably at least four, more preferably at least five, and most preferably all of them. In another preferred embodiment, the vaccine may include one or more of SEQ ID NOs: 24-53.

When considering which type of vaccine may be most effective for an individual, it is noted that the same protective response could be induced by the peptide or the full protein produced from the VRPs. Production of the peptide intracellularly is generally preferred because it is usually (but not always) more effective than providing it extracellularly. Thus, vaccines containing VRPs may be preferred because the VRPs infect cells and therefore achieve intracellular production.

Such vaccines might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective CTL responses.

In yet another embodiment, the present invention relates to a method for providing immunity against Ebola virus, said method comprising administering one or more VRPs expressing any combination of the GP, NP, VP24, VP30 or VP30#2, VP35 and VP40 Ebola proteins to a subject such that a protective immune reaction is generated. In another related embodiment, the method may entail administering one or more VRPs expressing any combination of the peptides designated SEQ ID NOs:24-53, or simply one or more of the peptides designated SEQ ID NOs:24-53.

Vaccine formulations of the present invention may comprise an immunogenic amount of a VRP, such as for example EboVP24VRP described above, or, for a multivalent vaccine, a combination of replicons, in a pharmaceutically acceptable carrier. An "immunogenic amount" is an amount of the VRP(s) sufficient to evoke an immune response in the subject to which the vaccine is administered. An amount of about $1 \times 10^8$ focus forming units or less, per dose, is suitable. The dosage may vary a bit depending upon the age and species of the subject being treated. For instance, in two species of monkeys the dosage of about $1 \times 10^8$ focus forming units was quite successful. The subject may be inoculated 2-4 times. Exemplary pharmaceutically acceptable carriers include, but are not limited to, sterile pyrogen-free water and sterile pyrogen-free physiological saline solution.

Administration of the VRPs disclosed herein may be carried out by any suitable means, including parenteral injection (such as intraperitoneal, subcutaneous, or intramuscular injection), in ovo injection of birds, orally, or by topical application of the virus (typically carried in a pharmaceutical formulation) to an airway surface. Topical application of the virus to an airway surface can be carried out by intranasal administration (e.g., by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation. As noted above, one preferred way is subcutaneous injection, and most preferred is intramuscular injection.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more DNA constructs or replicating RNA described above can be use in any combination effective to elicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

As noted above, the preferred vaccine schedule, especially for the GP-only vaccine and the six-protein vaccine, is Day 0, one month, four months, and twelve months. However, generally speaking, the vaccines described herein may also be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Other examples of suitable immunization schedules include: (i) 0, 1 months and 6 months, (ii) 0, 7 days and 1 month, (iii) 0 and 1 month, (iv) 0 and 6 months, (v) 0, 1 and 2 months, or other schedules sufficient to elicit the desired immune responses expected to confer protective immunity, or reduce disease symptoms, or reduce severity of disease.

In a further embodiment, the present invention relates to a method of detecting the presence of antibodies against Ebola virus in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the Ebola proteins described above or any combination thereof, and contacting it with the serum of a person or animal suspected of having Ebola. The presence of a resulting complex formed between the Ebola protein(s) and serum antibodies specific therefor can be detected by any of the known methods common in the art, such as fluorescent antibody spectroscopy or colorimetry. This method of detection can be used, for example, for the diagnosis of Ebola infection and for determining the degree to which an individual has developed virus-specific antibodies after administration of a vaccine.

In yet another embodiment, the present invention relates to a method for detecting the presence of Ebola virion proteins in a sample. Antibodies against GP, NP, and the VP proteins could be used for diagnostic assays. Using standard methodology well known in the art, a diagnostics assay can be constructed by coating on a surface (i.e. a solid support, for example, a microtitration plate or a membrane (e.g. nitrocellulose membrane)), antibodies specific for any of the Ebola proteins described above, and contacting it with serum or a tissue sample of a person suspected of having Ebola infection. The presence of a resulting complex formed between the protein or proteins in the serum and antibodies specific therefor can be detected by any of the known methods common in the art, such as fluorescent antibody spectroscopy or colorimetry. This method of detection can be used, for example, for the diagnosis of Ebola virus infection.

In another embodiment, the present invention relates to a diagnostic kit which contains any combination of the Ebola proteins described above and ancillary reagents that are well known in the art and that are suitable for use in detecting the presence of antibodies to Ebola in serum or a tissue sample. Tissue samples contemplated can be from monkeys, humans, or other mammals.

In yet another embodiment, the present invention relates to DNA or nucleotide sequences for use in detecting the presence of Ebola virus using the reverse transcription-polymerase chain reaction (RT-PCR). The DNA sequence of the present invention can be used to design primers which specifically bind to the viral RNA for the purpose of detecting the presence of Ebola virus or for measuring the amount of Ebola virus in a sample. The primers can be any length ranging from 7 to 400 nucleotides, preferably at least 10 to 15 nucleotides, or more preferably 18 to 40 nucleotides. Reagents and controls necessary for PCR reactions are well known in the art. The amplified products can then be analyzed for the presence of viral sequences, for example by gel fractionation, with or without hybridization, by radiochemistry, and immunochemistry techniques.

In yet another embodiment, the present invention relates to a diagnostic kit which contains PCR primers specific for Ebola virus and ancillary reagents for use in detecting the presence or absence of Ebola in a sample using PCR. Samples contemplated can be obtained from human, animal, e.g., horse, donkey, pig, mouse, hamster, monkey, or other mammals, birds, and insects, such as mosquitoes.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following MATERIALS AND METHODS were used in the examples that follow.

Cells Lines and Viruses

BHK (ATCC CCL 10), Vero 76 (ATCC CRL 1587), and Vero E6 (ATCC CRL 1586) cell lines were maintained in minimal essential medium with Earle's salts, 5-10% fetal bovine serum, and 500 g/mL gentamicin sulfate. For CTL assays, EL4 (ATCC TIB39), L5178Y (ATCC CRL 1723) and P815 (ATCC TIB64) were maintained in Dulbecco's minimal essential medium supplemented with 5-10% fetal bovine serum and antibiotics.

A stock of the Zaire strain of Ebola virus originally isolated from a patient in the 1976 outbreak (Maying a) and passaged intracerebrally 3 times in suckling mice and 2 times in Vero cells was adapted to adult mice through serial passage in progressively older suckling mice (Bray et al., (1998) J. Infect. Dis. 178, 651-661). A plaque-purified ninth-mouse-passage isolate which was uniformly lethal for adult mice ("mouse-adapted virus") was propagated in Vero E6 cells, aliquotted, and used in all mouse challenge experiments and neutralization assays.

A stock of the Zaire strain of Ebola 1976 virus was passaged spleen to spleen in strain 13 guinea pigs four times. This guinea pig-adapted strain was used to challenge guinea pigs.

Construction and Packaging of Recombinant VEE Virus Replicons (VRPs)

Replicon RNAs were packaged into VRPs as described (Pushko et al., 1997, supra). Briefly, capped replicon RNAs were produced in vitro by T7 run-off transcription of NotI-digested plasmid templates using the RiboMAX T7 RNA polymerase kit (Promega). BHK cells were co-transfected with the replicon RNAs and the 2 helper RNAs expressing the structural proteins of the VEE virus. The cell culture supernatants were harvested approximately 30 hours after transfection and the replicon particles were concentrated and purified by centrifugation through a 20% sucrose cushion. The pellets containing the packaged replicon particles were suspended in PBS and the titers were determined by infecting Vero cells with serial dilutions of the replicon particles and enumerating the infected cells by indirect immunofluorescence with antibodies specific for the Ebola proteins.

Immunoprecipitation of Ebola Virus Proteins Expressed from VEE Virus Replicons

BHK cells were transfected with either the Ebola virus GP, NP, VP24, VP30, VP35, or VP40 replicon RNAs. At 24 h post-transfection, the culture medium was replaced with minimal medium lacking cysteine and methionine, and proteins were labeled for 1 h with $^{35}$S-labeled methionine and cysteine. Cell lysates or supernatants (supe) were collected and immunoprecipitated with polyclonal rabbit anti-Ebola virus serum bound to protein A beads. $^{35}$S-labeled Ebola virus structural proteins from virions grown in Vero E6 cells were also immunoprecipitated as a control for each of the virion proteins. Immunoprecipitated proteins were resolved by electrophoresis on an 11% SDS-polyacrylamide gel and were visualized by autoradiography.

Vaccination of Mice with VEE Virus Replicons

Groups of 10 BALB/c or C57BL/6 mice per experiment were subcutaneously injected at the base of the neck with $2\times10^6$ focus-forming units of VRPs encoding the Ebola virus genes. As controls, mice were also injected with either a control VRP encoding the Lassa nucleoprotein (NP) or with PBS. For booster inoculations, animals received identical injections at 1 month intervals. Data are recorded as the combined results of 2 or 3 separate experiments.

Ebola Infection of Mice

One month after the final booster inoculation, mice were transferred to a BSL-4 containment area and challenged by intraperitoneal (ip) inoculation of 10 plaque-forming units (pfu) of mouse-adapted Ebola virus (approximately 300 times the dose lethal for 50% of adult mice). The mice were observed daily, and morbidity and mortality were recorded. Animals surviving at day 21 post-infection were injected again with the same dose of virus and observed for another 21 days.

In some experiments, 4 or 5 mice from vaccinated and control groups were anesthetized and exsanguinated on day 4 (BALB/c mice) or day 5 (C57BL/6 mice) following the initial viral challenge. The viral titers in individual sera were determined by plaque assay.

Passive Transfer of Immune Sera to Naive Mice.

Donor sera were obtained 28 days after the third inoculation with $2\times10^6$ focus-forming units of VRPs encoding the indicated Ebola virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted Ebola virus.

Vaccination and Challenge of Guinea Pigs.

EboGPVRP or EboNPVRP ($1\times10^7$ focus-forming units in 0.5 ml PBS) were administered subcutaneously to inbred strain 2 or strain 13 guinea pigs (300-400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge. Guinea pigs were challenged on day 56 (strain 2) or day 160 (strain 13) by subcutaneous administration of 1000 $LD_{50}$ ($1\times10^4$ PFU) of guinea pig-adapted Ebola virus. Animals were observed daily for 60 days, and morbidity (determined as changes in behavior, appearance, and weight) and survival were recorded. Blood samples were taken on the days indicated after challenge and viremia levels were determined by plaque assay.

Virus Titration and Neutralization Assay.

Viral stocks were serially diluted in growth medium, adsorbed onto confluent Vero E6 cells in 6- or 12-well dishes, incubated for 1 hour at 37° C., and covered with an agarose overlay (Moe, J. et al. (1981) J. Clin. Microbiol. 13:791-793). A second overlay containing 5% neutral red solution in PBS or agarose was added 6 days later, and plaques were counted the following day. Pooled pre-challenge serum samples from some of the immunized groups were tested for the presence of Ebola-neutralizing antibodies by plaque reduction neutralization assay. Aliquots of Ebola virus in growth medium were mixed with serial dilutions of test serum, or with normal serum, or medium only, incubated at 37° C. for 1 h, and used to infect Vero E6 cells. Plaques were counted 1 week later.

Cytotoxic T Cell Assays.

BALB/c and C57BL/6 mice were inoculated with VRPs encoding Ebola virus NP or VP24 or the control Lassa NP protein. Mice were euthanized at various times after the last inoculation and their spleens removed. The spleens were gently ruptured to generate single cell suspensions. Spleen cells ($1\times10^6$/ml) were cultured in vitro for 2 days in the presence of 10-25 □M of peptides synthesized from Ebola virus NP or VP24 amino acid sequences, and then for an additional 5 days in the presence of peptide and 10% supernatant from concanavalin A-stimulated syngeneic spleen cells. Synthetic peptides were made from Ebola virus amino acid sequences predicted by a computer algorithm (HLA Peptide Binding Predictions, Parker, K. C., et al. (1994) *J. Immunol.* 152:163) to have a likelihood of meeting the MHC class I binding requirements of the BALB/c (H-$2^d$) and C57BL/6 (H-$2^b$) haplotypes. Only 2 of 8 peptides predicted by the algorithm and tested to date have been identified as containing CTL epitopes. After in vitro restimulation, the spleen cells were tested in a standard $^{51}$chromium-release assay well known in the art (see, for example, Hart et al. (1991) *Proc. Natl. Acad. Sci. USA* 88: 9449-9452). Percent specific lysis of peptide-coated, MHC-matched or mismatched target cells was calculated as:

$$\frac{\text{Experimental } cpm - \text{Spontaneous } cpm}{\text{Maximum } cpm - \text{Spontaneous } cpm} \times 100$$

Spontaneous cpm are the number of counts released from target cells incubated in medium. Maximum cpm are obtained by lysing target cells with 1% Triton X-100. Experimental cpm are the counts from wells in which target cells are incubated with varying numbers of effector (CTL) cells. Target cells tested were L5178Y lymphoma or P815 mastocytoma cells (MHC matched to the H$2^d$ BALB/c mice and EL4 lymphoma cells (MHC matched to the H$2^b$ C57BL/6 mice). The effector:target (E:T) ratios tested were 25:1, 12:1, 6:1 and 3:1.

Example 1

Survival Of Mice Inoculated With VRPs Encoding Ebola Proteins. Mice were inoculated two or three times at 1 month intervals with 2×10$^6$ focus-forming units of VRPs encoding individual Ebola virus genes, or Lassa virus NP as a control, or with phosphate buffered saline (PBS). Mice were challenged with 10 pfu of mouse-adapted Ebola virus one month after the final immunization. The mice were observed daily, and morbidity and mortality data are shown in Table 1A for BALB/c mice and Table 1B for C57BL/6 mice. The viral titers in individual sera of some mice on day 4 (BALB/c mice) or day 5 (C57BL/6 mice) following the initial viral challenge were determined by plaque assay.

Table 1. Survival of Mice Inoculated with VRPs Encoding Ebola Proteins

TABLE 1

Survival of Mice Inoculated With VRPs Encoding Ebola Proteins

| VRP | # Injections | S/T$^1$ (%) | MDD$^2$ | V/T$^3$ | Viremia$^4$ |
|---|---|---|---|---|---|
| A. BALB/c Mice | | | | | |
| EboNP | 3 | 30/30 (100%) | | 5/5 | 5.2 |
| | 2 | 19/20 (95%) | 7 | 5/5 | 4.6 |
| EboGP | 3 | 15/29 (52%) | 8 | 1/5 | 6.6 |
| | 2 | 14/20 (70%) | 7 | 3/5 | 3.1 |
| EboVP24 | 3 | 27/30 (90%) | 8 | 5/5 | 5.2 |
| | 2 | 19/20 (95%) | 6 | 4/4 | 4.8 |
| EboVP30 | 3 | 17/20 (85%) | 7 | 5/5 | 6.2 |
| | 2 | 11/20 (55%) | 7 | 5/5 | 6.5 |
| EboVP35 | 3 | 5/19 (26%) | 7 | 5/5 | 6.9 |
| | 2 | 4/20 (20%) | 7 | 5/5 | 6.5 |
| EboVP40 | 3 | 14/20 (70%) | 8 | 5/5 | 4.6 |
| | 2 | 17/20 (85%) | 7 | 5/5 | 5.6 |

TABLE 1-continued

Survival of Mice Inoculated With VRPs Encoding Ebola Proteins

| VRP | # Injections | S/T$^1$ (%) | MDD$^2$ | V/T$^3$ | Viremia$^4$ |
|---|---|---|---|---|---|
| LassaNP | 3 | 0/29 (0%) | 7 | 5/5 | 8.0 |
| | 2 | 0/20 (0%) | 7 | 5/5 | 8.4 |
| none (PBS) | 3 | 1/30 (3%) | 6 | 5/5 | 8.3 |
| | 2 | 0/20 (0%) | 6 | 5/5 | 8.7 |
| B. C57BL/6 Mice | | | | | |
| EboNP | 3 | 15/20 (75%) | 8 | 5/5 | 4.1 |
| | 2 | 8/10 (80%) | 9 | ND$^5$ | ND |
| EboGP | 3 | 19/20 (95%) | 10 | 0/5 | — |
| | 2 | 10/10 (100%) | — | ND | ND |
| EboVP24 | 3 | 0/20 (0%) | 7 | 5/5 | 8.6 |
| EboVP30 | 3 | 2/20 (10%) | 8 | 5/5 | 7.7 |
| EboVP35 | 3 | 14/20 (70%) | 8 | 5/5 | 4.5 |
| EboVP40 | 3 | 1/20 (5%) | 7 | 4/4 | 7.8 |
| LassaNP | 3 | 1/20 (5%) | 7 | 4/4 | 8.6 |
| | 2 | 0/10 (0%) | 7 | ND | ND |
| none (PBS) | 3 | 3/20 (15%) | 7 | 5/5 | 8.6 |
| | 2 | 0/10 (0%) | 7 | ND | ND |

$^1$S/T, Survivors/total challenged.
$^2$MDD, Mean day to death
$^3$V/T, Number of mice with viremia/total number tested.
$^4$Geometric mean of Log$_{10}$ viremia titers in PFU/mL. Standard errors for all groups were 1.5 or less, except for the group of BALB/c mice given 2 inoculations of EboGP, which was 2.2.
$^5$ND, not determined.

Example 2

VP24-Immunized BALB/C Mice Survive a High-Dose Challenge with Ebola Virus

BALB/c mice were inoculated two times with 2×10$^6$ focus-forming units of EboVP24VRP. Mice were challenged with either 1×10$^3$ pfu or 1×10$^5$ pfu of mouse-adapted Ebola virus 1 month after the second inoculation. Morbidity and mortality data for these mice are shown in Table 2.

TABLE 2

VP24-Immunized BALB/c Mice Survive A High-Dose Challenge With Ebola virus

| Replicon | Challenge Dose | Survivors/Total |
|---|---|---|
| EboVP24 | 1 × 10$^3$ pfu (3 × 10$^4$ LD$_{50}$) | 5/5 |
| EboVP24 | 1 × 10$^5$ pfu (3 × 10$^6$ LD$_{50}$) | 5/5 |
| None | 1 × 10$^3$ pfu (3 × 10$^4$ LD$_{50}$) | 0/4 |
| None | 1 × 10$^5$ pfu (3 × 10$^6$ LD$_{50}$) | 0/3 |

Example 3

Passive Transfer of Immune Sera can Protect Naive Mice from a Lethal Challenge of Ebola Virus Donor sera were obtained 28 days after the third inoculation with 2×10$^6$ focus-forming units of VRPs encoding the indicated Ebola virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted Ebola virus.

TABLE 3

Passive Transfer of Immune Sera Can Protect Unvaccinated Mice from a Lethal Challenge of Ebola Virus

| Specificity of Donor Sera | Survivors/ Total | Mean Day of Death |
|---|---|---|
| A. BALB/c Mice | | |
| Ebola GP | 15/20 | 8 |
| Ebola NP | 1/20 | 7 |
| Ebola VP24 | 0/20 | 6 |
| Ebola VP30 | 0/20 | 7 |
| Ebola VP35 | ND[1] | ND |
| Ebola VP40 | 0/20 | 6 |
| Lassa NP | 0/20 | 7 |
| Normal mouse sera | 0/20 | 6 |
| B. C57BL/6 Mice | | |
| Ebola GP | 17/20 | 7 |
| Ebola NP | 0/20 | 7 |
| Ebola VP24 | ND | ND |
| Ebola VP30 | ND | ND |
| Ebola VP35 | 0/20 | 7 |
| Ebola VP40 | ND | ND |
| Lassa NP | 0/20 | 7 |
| Normal mouse sera | 0/20 | 7 |

[1]ND, not determined

Example 4

Immunogenicity and Efficacy of VRepEboGP and VRepEboNP in Guinea Pigs

EboGPVRP or EboNPVRP ($1 \times 10^7$ IU in 0.5 ml PBS) were administered subcutaneously to inbred strain 2 or strain 13 guinea pigs (300-400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge.

Sera from vaccinated animals were assayed for antibodies to Ebola by plaque-reduction neutralization, and ELISA. Vaccination with VRepEboGP or NP induced high titers of antibodies to the Ebola proteins (Table 4) in both guinea pig strains. Neutralizing antibody responses were only detected in animals vaccinated with the GP construct (Table 4).

Guinea pigs were challenged on day 56 (strain 2) or day 160 (strain 13) by subcutaneous administration of 1000 $LD_{50}$ ($10^4$ PFU) of guinea pig-adapted Ebola virus. Animals were observed daily for 60 days, and morbidity (determined as changes in behavior, appearance, and weight) and survival were recorded. Blood samples were taken on the days indicated after challenge and viremia levels were determined by plaque assay. Strain 13 guinea pigs vaccinated with the GP construct, alone or in combination with NP, survived lethal Ebola challenge (Table 4). Likewise, vaccination of strain 2 inbred guinea pigs with the GP construct protected ⅗ animals against death from lethal Ebola challenge, and significantly prolonged the mean day of death (MDD) in one of the two animals that died (Table 4). Vaccination with NP alone did not protect either guinea pig strain.

TABLE 4

Immunogenicity and efficacy of VRepEboGP and VRepEboNP in guinea pigs

| VRP | ELISA[a] | PRNT$_{50}$ | Survivors/ total(MDD[b]) | Viremia[c] d7 | d14 |
|---|---|---|---|---|---|
| A. Strain 2 guinea pigs | | | | | |
| GP | 4.1 | 30 | 3/5 (13 + 2.8) | 2.3 | 1.8 |
| NP | 3.9 | <10 | 0/5 (9.2 + 1.1) | 3.0 | — |
| Mock | <1.5 | <10 | 0/5 (8.8 + 0.5) | 3.9 | — |
| B. Strain 13 guinea pigs | | | | | |
| GP | 4.0 | 140 | 5/5 | <2.0 | <2.0 |
| GP/NP | 3.8 | 70 | 5/5 | <2.0 | <2.0 |
| NP | 2.8 | <10 | 1/5 (8.3 + 2.2) | 4.6 | — |
| Lassa NP | <1.5 | <10 | 2/5 (8.3 + 0.6) | 4.8 | — |

[a]Data are expressed as geometric mean titers, $\log_{10}$.
[b]MDD, mean day to death
[c]Geometric mean of $\log_{10}$ viremia titers in PFU/mL. Standard errors for all groups were 0.9 or less.

Example 5

Induction of Murine CTL Responses to Ebola Virus NP and Ebola Virus VP24 Proteins BALB/c and C57BL/6 mice were inoculated with VRPs encoding Ebola virus NP or VP24. Mice were euthanized at various times after the last inoculation and their spleens removed. Spleen cells ($1 \times 10^6$/ml) were cultured in vitro for 2 days in the presence of 10 to $\square$M of peptides, and then for an additional 5 days in the presence of peptide and 10% supernatant from concanavalin A-stimulated syngeneic spleen cells. After in vitro restimulation, the spleen cells were tested in a standard $^{51}$chromium-release assay. Percent specific lysis of peptide-coated, MHC-matched or mismatched target cells was calculated as:

$$\frac{\text{Experimental } cpm - \text{Spontaneous } cpm}{\text{Maximum } cpm - \text{Spontaneous } cpm} \times 100$$

In the experiments shown, spontaneous release did not exceed 15%.

TABLE 5

Induction of murine CTL responses to Ebola virus NP and Ebola virus VP24 proteins.

| Mice, VRP[1] | Peptide[2] | Cell[3] | % Specific Lysis E:T ratio 25 |
|---|---|---|---|
| BALB/c, VP24 | None | P815 | 55 |
| BALB/c, VP24 | SEQ ID NO:25 | P815 | 93 |
| C57BL/6, EboNP | None | EL4 | 2 |
| C57BL/6, EboNP[4] | SEQ ID NO:24 | EL4 | 70 |
| C57BL/6, EboNP | Lassa NP | EL4 | 2 |
| C57BL/6, LassaNP | None | L5178Y | 1 |
| C57BL/6, LassaNP | SEQ ID NO:24 | L5178Y | 0 |
| C57BL/6, LassaNP | None | EL4 | 2 |
| C57BL/6, LassaNP | SEQ ID NO:24 | EL4 | 6 |

[1]Indicates the mouse strain used and the VRP used as the in vivo immunogen. In vitro restimulation was performed using SEQ ID NO:24 peptide for BALB/c mice and SEQ ID NO:23 for all C57BL/6 mice shown.
[2]Indicates the peptide used to coat the target cells for the chromium release assay.
[3]Target cells are MHC-matched to the effector cells, except for the L5178Y cells that are C57BL/6 mismatched.
[4]High levels of specific lysis (>40%) were also observed using E:T ratios of 12, 6, 3, or 1:1.

Example 6

Induction of Murine T Cell Responses that Protect Against Ebola Challenge

Mice and injections. BALB/c and C57Bl/6 mice were injected sc with $2\times10^6$ IU of VEE virus replicons encoding either the individual Ebola genes or Lassa NP (3 injections 1 month apart). The genes used to make replicons are from the human Zaire76 virus. One month after the final immunization, mice were transferred to BSL-4 containment and challenged by ip inoculation of 10 or 1000 pfu (300 or 30000 $LD_{50}$) of mouse-adapted Ebola Zaire. This virus has amino acid changes in NP at nt 683 (S to G), VP35 at nt 3163 (A to V), VP24 at nt 10493 (T to I), and in L at nt 14380 (F to L) and nt 16174 (I to V). There are three other nt changes, including an insertion in the intergenic region at nt 10343. GenBank accession number AF499101.

T cell assays. Single cell suspensions were prepared from spleens by passage through cell 70 μM strainers. Spleen cells were depleted of erythrocytes by treatment with buffered ammonium chloride solution and enumerated by trypan blue exclusion on a hemacytometer. For in vitro restimulations, 1-5 μg peptide(s) and human recombinant IL-2 (10 U/ml, National Cancer Institute) were added to a cell density of $1\times10^6$/ml and the cultures incubated 4-7 days. For intracellular IFN-γ staining, splenocytes were cultured at 37° C. for 5 hr with 1-5 μg of peptide(s) or PMA (25 ng/ml) and ionomycin (1.25 ug/ml) in 100 μl complete medium containing 10 μg/ml brefeldin A (BFA). After culture, the cells were blocked with mAbs to FcRIII/II receptor and stained with αCD44 FITC and anti-CD8 Cychrome (Pharmingen, San Diego, Calif.) in PBS/BFA. The cells were then fixed in 1% formaldehyde (Ted Pella, Redding, Calif.), permeabilized with PBS containing 0.5% saponin, and stained with αIFN-γ PE (Pharmingen, San Diego, Calif.). The data were acquired using a FACSCalibur flow cytometer and analyzed with CELLQuest software (Becton-Dickinson. Cytotoxicity assays were performed using target cells (EL4, L5178Y) labeled with $^{51}Cr$ ($Na_2CrO_4$; New England Nuclear, Boston, Mass.) and pulsed with peptide for 1.5 hours. Unpulsed target cells were used as negative controls. Various numbers of effector cells were incubated with 2500 target cells for 4 hours. Percentage specific release was calculated as: % specific release=(experimental−spontaneous)/(maximum−spontaneous)×100. Spontaneous release values were obtained by incubation of target cells in medium alone and were routinely <10% of maximum release. Maximum release values were obtained by the addition of 100 μl 1% TritonX-100.

Adoptive transfer experiments. After in vitro restimulation, cells are Ficoll purified, washed three times with 0.3M methyl-α-D-mannopyranoside and twice with complete media. Cells are counted and adjusted to $25.0\times10^6$ cells/ml in endotoxin-free PBS. A total volume of 0.2 mls is given to each mouse by i.p. injection 4 hr before challenge with 1000 PFU of mouse-adapted Ebola virus. Animals are observed and sickness or death is noted on daily charts.

As shown in Table A, this data identifies the protective mechanism induced by VRP vaccination, showing the role of T cells. It indicates the ability to predict protection from in vitro assays, specifically the intracellular cytokine and chromium release assays. Thus, a positive ICC result is reasonably predictive of conferred protection, even if the protection is listed as incomplete; the rest of the data strongly indicate protection. Notably, where the CTL sequences are conserved between Zaire and the other Ebola viruses, cross-protection may reasonably be inferred. (The protection in Table A refers to adoptive transfer of CTLs to unvaccinated mice before challenge, not the vaccination with a certain protein.)

Example 7

Determination of Interference in Protection by Multiple Replicons

The purpose of this experiment was to determine if multiple VEE replicons that do not provide complete protection (VP24, 30, 40 in BL/6 mice) will interfere with a protective replicon Ebola NP that has defined CTL epitopes. Co-administration did not interfere with the induction of protection.

| Vaccine | Survival |
|---|---|
| VRep EBOV NP, VP24, VP30, VP40 | 10/10 |
| VRep EBOV NP | 6/6 |
| PBS | 0/7 |

The CTLs to NP are CD8(+), and recognize epitopes SEQ ID NO:24, 26 and 27. Evaluation of the ability to lyse peptide-pulsed target cells was assessed using spleen cells from mice vaccinated with the EBOC VRepNP alone, or all four replicons (NP, VP24, VP30 and VP40). Although responses were somewhat lower in the mice receiving four replicons, the threshold of immunity was maintained.

| Vaccine | Effector/target ratio | % Lysis of target cells coated with peptide (background on untreated target cells is subtracted) | | |
|---|---|---|---|---|
| | | NP-1 | NP-8 | NP-17 |
| NP | 100:1 | 55 | 31 | 64 |
| | 50:1 | 61 | 23 | 45 |
| | 25:1 | 67 | 15 | 31 |
| | 12:1 | 51 | 13 | 21 |
| Mix | 100:1 | 41 | 40 | 45 |
| | 50:1 | 37 | 32 | 28 |
| | 25:1 | 26 | 33 | 19 |
| | 12:1 | 19 | 18 | 12 |

Example 8

Improved Efficacy Induced by a Cocktail Formulation of Suboptimal EBOV Vrep

In studies where we examined the protective efficacy of replicons individually, we observed that some replicons (such as VP30, VP24 and VP40) protected fewer than 100% of the mice. When protection was less than 50%, we suggested that the protein was not particularly protective for that mouse strain. However, in some cases, we did observe that 20-30% of the mice survived, suggesting that we might be able to optimize our vaccine strategy to provide protection with those proteins. As we are evaluating a cocktail formulation, we approached this issue by injecting mice with combinations of the three VP replicons than had poor efficacy in C57Bl/6 mice.

C57BL/6 mice were injected SC at the base of the neck with $2.0\times10^6$ packaged VEE virus replicon particles for each Ebola VP protein, then rested for 27 days and then boosted twice at days 28 and 56. On day 84, mice were injected intraperitoneally with approximately 3×10⁴ LD50 (1000 PFU) of mouse-adapted Ebola virus.

| Strain | Vaccine | Survival |
|---|---|---|
| C57BL/6 | VRep VP35 | 30/30 |
| C57BL/6 | VReps VP35, VP30, VP24, VP40 | 30/30 |
| C57BL/6 | Medium | 0/23 |
| C57BL/6 | VReps VP30, VP24, VP40 | 28/30 |

The data indicate that combining the three VP replicons provided significantly better protection than when we administered them singly. Of note, the VP24 replicon has never protected a single C57BL/6 mouse when administered alone and is not likely contributing to protection. However, importantly, its inclusion in the formulation also does not interfere with induction of protective responses to the other VPs.

These data shows that a cocktail formulation may be a preferred vaccine because it induces a broader array of T cells (i.e. CTLs to multiple proteins) and that, together, these may meet the threshold needed for protection. We expect the same phenomenon will apply to non-human primate studies. This also provides support for the inclusion of multiple Ebola peptides/proteins in a cocktail formulation. As an example, if a human infected with Ebola needs 1 million effectors, but vaccination induces only 400,000 to each protein, it may be additive to have 1.2 million spread across 3 proteins. Otherwise, waiting one day for that person's cells to divide to 800,000 and a second day to cross 1 million—but that would likely be too late for survival.

Figure 4:
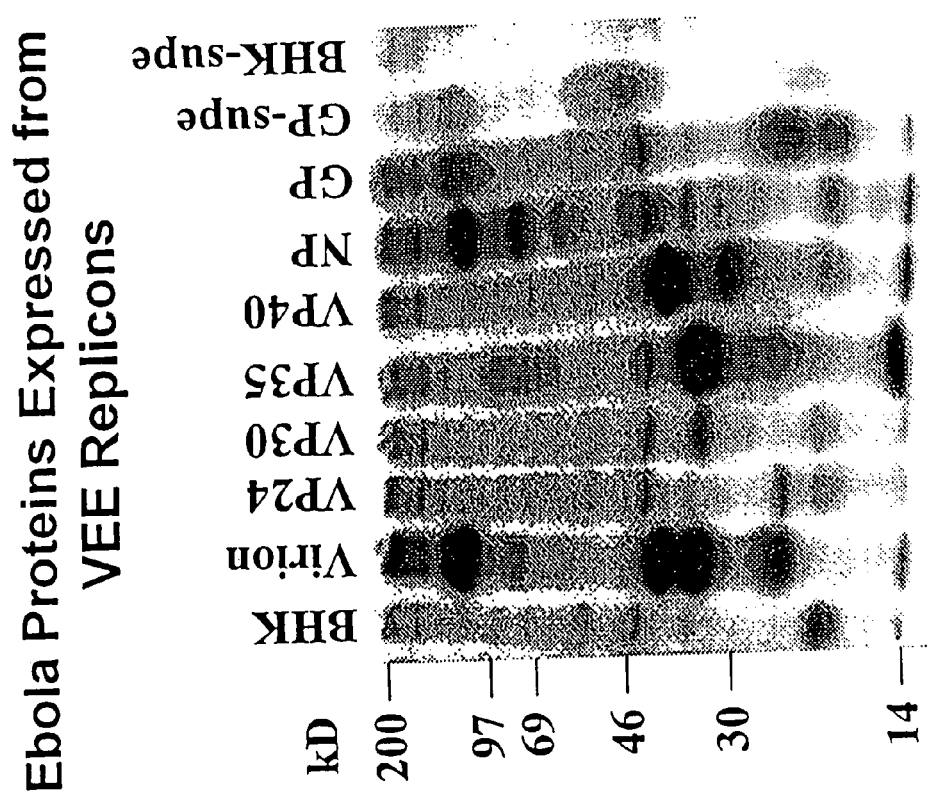

Ebola Zaire 1976 (Maying a) virus causes acute hemorrhagic fever characterized by high mortality. There are no current vaccines or effective therapeutic measures to protect individuals who are exposed to this virus. In addition, it is not known which genes are essential for evoking protective immunity and should therefore be included in a vaccine designed for human use. In this study, the GP, NP, VP24, VP30, VP35, and VP40 virion protein genes of the Ebola Zaire 1976 (Maying a) virus were cloned and inserted into a Venezuelan equine encephalitis (VEE) virus replicon vector (VRep) as shown in FIGS. 2A and 2B. These VReps were packaged as VEE replicon particles (VRPs) using the VEE virus structural proteins provided as helper RNAs, as shown in FIG. 3. This enables expression of the Ebola virus proteins in host cells. The Ebola virus proteins produced from these constructs were characterized in vitro and were shown to react with polyclonal rabbit anti-Ebola virus antibodies bound to Protein A beads following SDS gel electrophoresis of immunoprecipitated proteins (FIG. 4).

The Ebola virus genes were sequenced from the VEE replicon clones and are listed here as SEQ ID NO:1 (GP), 2 (NP), 3 (VP24), 4 (VP30), 5 (VP35), 6 (VP40), and 7 (VP30#2) as described below. The corresponding amino acid sequences of the Ebola proteins expressed from these replicons are listed as SEQ ID NO: 17, 18, 19, 20, 21, 22, and 23, respectively. Changes in the DNA sequence relative to the sequence published by Sanchez et al. (1993) are described relative to the nucleotide (nt) sequence number from GenBank (accession number L11365).

The sequence we obtained for Ebola virus GP (SEQ ID NO: 1) differed from the GenBank sequence by a transition from A to G at nt 8023. This resulted in a change in the amino acid sequence from Ile to Val at position 662 (SEQ ID NO: 17).

The DNA sequence we obtained for Ebola virus NP (SEQ ID NO:2) differed from the GenBank sequence at the following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The Ebola virus VP24 (SEQ ID NO:3) gene differed from the GenBank sequence at 6 positions, resulting in 3 nonconservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

We have included 2 different sequences for the Ebola virus VP30 gene (SEQ ID NOS:4 and SEQ ID NO:7). Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS: 20 and SEQ ID NO:23). As a result, the C-terminus of the VP30 protein differs significantly from that previously reported. In addition to these 2 changes, the VP30#2 gene in SEQ ID NO:23 contains a conservative transition from T to C at nt 9217. Because the primers originally used to clone the VP30 gene into the replicon were designed based on the GenBank sequence, the first clone that we constructed (SEQ ID NO:4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO:23) did not inhibit the ability of the protein to serve as a protective antigen in BALB/c mice. We have also determined that a VEE replicon construct (SEQ ID NO:7), which contains the authentic C-terminus of VP30 (VP30#2, SEQ ID NO:23), is able to protect mice against a lethal Ebola challenge.

The DNA sequence for Ebola virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO:21). The insertion of the T residue resulted in a change in the open reading frame of VP35 from that previously reported by Sanchez et al. (1993) following amino acid number 324. As a result, Ebola virus VP35 encodes for a protein of 340 amino acids, where amino acids 325 to 340 (SEQ ID NO:21) differ from and replace the C-terminal 27 amino acids of the previously published sequence.

Sequencing of VP30 and VP35 was also performed on RT/PCR products from RNA derived from cells that were infected with Ebola virus 1976, Ebola virus 1995 or the mouse-adapted Ebola virus. The changes noted above for the VRep constructs were also found in these Ebola viruses. Thus, we believe that these changes are real events and not artifacts of cloning.

The Ebola virus VP40 differed from the GenBank sequence by a transversion from a C to G at nt 4451 and a transition from a G to A at nt 5081. These sequence changes did not alter the protein sequence of VP40 (SEQ ID NO:22) from that of the published sequence.

To evaluate the protective efficacy of individual Ebola virus proteins and to determine whether the major histocompatibility (MHC) genes influence the immune response to Ebola virus antigens, two MHC-incompatible strains of mice were vaccinated with VRPs expressing an Ebola protein. As controls for these experiments, some mice were injected with VRPs expressing the nucleoprotein of Lassa virus or were injected with phosphate-buffered saline (PBS). Following Ebola virus challenge, the mice were monitored for morbidity and mortality, and the results are shown in Table 1.

The GP, NP, VP24, VP30, and VP40 proteins of Ebola virus generated either full or partial protection in BALB/c mice, and may therefore be useful components of a vaccine for humans or other mammals. Vaccination with VRPs encoding the NP protein afforded the best protection. In this case, 100% of the mice were protected after three inoculations and 95% of the mice were protected after two inoculations. The VRP encoding VP24 also protected 90% to 95% of BALB/c mice against Ebola virus challenge. In separate experiments (Table 2), two or three inoculations with VRPs encoding the VP24 protein protected BALB/c mice from a high dose ($1 \times 10^5$ plaque-forming units ($3 \times 10^6$ LD50)) of mouse-adapted Ebola virus.

Example 1 shows that vaccination with VRPs encoding GP protected 52-70% of BALB/c mice. The lack of protection was not due to a failure to respond to the VRP encoding GP, as all mice had detectable Ebola virus-specific serum antibodies after vaccination. Improved results were later seen, which are thought to be dose-dependent. Further, as shown in Examples 6-8, combining suboptimal formulations gives dramatically better protection.

Also in Example 1, some protective efficacy was further observed in BALB/c mice vaccinated two or three times with VRPs expressing the VP30 protein (55% and 85%, respectively), or the VP40 protein (70% and 80%, respectively). The VP35 protein was not efficacious in the BALB/c mouse model, as only 20% and 26% of the mice were protected after either two or three doses, respectively. Again, improved results were later seen, which are thought to be dose-dependent; and we found that combining suboptimal formulations gives dramatically better protection (e.g., combination of VP24, VP30 and VP40).

Geometric mean titers of viremia were markedly reduced in BALB/c mice vaccinated with VRPs encoding Ebola virus proteins after challenge with Ebola virus, indicating an ability of the induced immune responses to reduce virus replication (Table 1A). In this study, immune responses to the GP protein were able to clear the virus to undetectable levels within 4 days after challenge in some mice.

When the same replicons were examined for their ability to protect C57BL/6 mice from a lethal challenge of Ebola virus, only the GP, NP, and VP35 proteins were efficacious (Table 1B). The best protection, 95% to 100%, was observed in C57BL/6 mice inoculated with VRPs encoding the GP protein. Vaccination with VRPs expressing NP protected 75% to 80% of the mice from lethal disease. In contrast to what was observed in the BALB/c mice, the VP35 protein was the only VP protein able to significantly protect the C57BL/6 mice. In this case, 3 inoculations with VRPs encoding VP35 protected 70% of the mice from Ebola virus challenge. The reason behind the differences in protection in the two mouse strains is believed to be due to the ability of the immunogens to sufficiently stimulate the cellular immune system. As with the BALB/c mice, the effects of the induced immune responses were also observed in reduced viremias and, occasionally, in a prolonged time to death of C57BL/6 mice.

Example 4 shows that VRPs expressing Ebola virus GP or NP were also evaluated for protective efficacy in a guinea pig model. Sera from vaccinated animals were assayed for antibodies to Ebola by western blotting, IFA, plaque-reduction neutralization, and ELISA. Vaccination with either VRP (GP or NP) induced high titers of antibodies to the Ebola proteins (Table 4) in both guinea pig strains. We later found that VP40 induced high titers (4 logs) in mice. Neutralizing antibody responses were only detected in animals vaccinated with the VRP expressing GP (Table 4).

As shown in Example 4, vaccination of strain 2 inbred guinea pigs with the GP construct protected 3/5 animals against death from lethal Ebola challenge, and significantly prolonged the mean day of death in one of the two animals that died (Table 4). All of the strain 13 guinea pigs vaccinated with the GP construct, alone or in combination with NP, survived lethal Ebola challenge (Table 4). Vaccination with NP alone did not protect either guinea pig strain from challenge with the guinea pig-adapted Ebola virus. Of note, guinea pigs are also inbred, and the failure of NP to protect may indicate that they could not respond with appropriate T cells, but could make protective antibodies to GP. This is further support for our preferred embodiments including multiple peptides and proteins, and even all six of the Ebola proteins.

As shown in Example 3, to identify the immune mechanisms that mediate protection against Ebola virus and to determine whether antibodies are sufficient to protect against lethal disease, passive transfer studies were performed. One mL of immune sera, obtained from mice previously vaccinated with one of the Ebola virus VRPs, was passively administered to unvaccinated mice 24 hours before challenge with a lethal dose of mouse-adapted Ebola virus. Antibodies to GP, but not to NP or the VP proteins, protected mice from an Ebola virus challenge (Table 3). Antibodies to GP protected 75% of the BALB/c mice and 85% of the C57BL/6 mice from death. When the donor sera were examined for their ability to neutralize Ebola virus in a plaque-reduction neutralization assay, a 1:20 to 1:40 dilution of the GP-specific antisera reduced the number of viral plaque-forming units by at least 50% (data not shown). In contrast, antisera to the NP and VP proteins did not neutralize Ebola virus at a 1:20 or 1:40 dilution. These results are consistent with the finding that GP is the only viral protein found on the surface of Ebola virus, and is likely to induce virus-neutralizing antibodies.

As shown in Examples 5 and 6, cince the NP and VP proteins of Ebola virus are internal virion proteins to which antibodies are not sufficient for protection, it is likely that cytotoxic T lymphocytes (CTLs) are also important for protection against Ebola virus. The inventors investigated cellular immune responses to individual Ebola virus proteins expressed from VRPs identified CTL responses to the VP24 and NP proteins (Table 5). One CTL epitope that we identified for the Ebola virus NP is recognized by C57BL/6 (H-$2^b$) mice, and has an amino acid sequence of, or contained within, the following 11 amino acids: VYQVNNLEEIC (SEQ ID NO:24). Vaccination with EboNPVRP and in vitro restimulation of spleen cells with this peptide consistently induces strong CTL responses in C57BL/6 (H-$2^b$) mice. In vivo vaccination to Ebola virus NP is required to detect the CTL activity, as evidenced by the failure of cells from C57BL/6 mice vaccinated with Lassa NP to develop lytic activity to peptide (SEQ ID NO:24) after in vitro restimulation with it. Specific lysis has been observed using very low effector: target ratios (<2:1). This CTL epitope is H-2$^b$ restricted in that it is not recognized by BALB/c (H-2$^d$) cells treated the same way (data not shown), and H-2$^b$ effector cells will not lyse MHC-mismatched target cells coated with this peptide.

A CTL epitope in the VP24 protein was also identified. It is recognized by BALB/c (H-2$^d$) mice, and has an amino acid sequence of, or contained within, the following 23 amino acids: LKFINKLDALLVVNYNGLLSSIF (SEQ ID NO:25). In the data shown in Table 5, high (>90%) specific lysis of P815 target cells coated with this peptide was observed. The background lysis of cells that were not peptide-coated was also high (>50%), which is probably due to the activity of natural killer cells. We are planning to repeat this experiment using the L5178Y target cells, which are not susceptible to natural killer cells. This shows that CTLs mediated protection, which is further demonstrated by the evidence in Examples 6, 7 and 8.

Example 9

Testing in Rhesus Monkeys

Purpose: Examine the cellular and humoral immune responses to the VRP-GP vaccine and determine the efficacy in monkeys (rhesus).

For this example and the example immediately below, the aim of this study was to examine the humoral and cellular immune responses generated by VEE replicon (VRP) expressing Ebola GP in two species of primates. In the data presented, we evaluated the efficacy of the VRP-GP vaccine in rhesus macaque, and later evaluated the same vaccine strategy in cynomolgus macaques.

In brief summary, three rhesus macaques were vaccinated with Ebola GP-VRPs and a control macaque received VRP expressing anthrax protective antigen. B and T cell responses were evaluated during the vaccination and post-challenge phases of the study. Following a 1000 pfu challenge with virulent Ebola Zaire virus, the two rhesus macaques with the highest antibody titers to Ebola virus survived whereas the control animal and the macaque with the lowest antibody titer died approximately 9 days later.

Procedure:

Three filovirus-naive and alphavirus-naïve rhesus macaques were vaccinated subcutaneously (SOP AC-09-50) with 1×10$^8$ focus forming units (FFU) of VEE virus replicons expressing Ebola GP on day 0, and boosted on days 28 and 139 (see table below). The vaccine was packaged VEE virus replicons expressing Ebola GP that was produced and purified at Alphavax under an existing CRDA. One control animal was vaccinated with 1×10$^8$ FFU VRP that expressed anthrax PA. Animals were bled prior to vaccination and cells were frozen for use in cellular assays such as chromium release assays. Animals received vaccine boosts on days 28 and 139. For sera and cellular assays the animals were bled seven days after vaccination and 28 days after the last booster vaccination. T cell responses were evaluated by ELISPOT analysis for IFN-γ expression to pooled overlapping peptide sequences or individual peptides that represent the Ebola GP. All vaccinated animals developed titers specific to Ebola (≧1:300) before they were challenged. Macaques were challenged with an intramusclular injection of Ebola Zaire virus on day 173 with 1,092 PFU of virus.

| Group | Species of Monkey | Vaccination | # of Monkeys | Challenge Dose (pfu) |
|---|---|---|---|---|
| B | Rhesus | VRP-GP | 3 | 1000 |
| E | Rhesus | VRP-GP | 1 | 1000 |

Results:

Humoral Immunity

Figure 5:
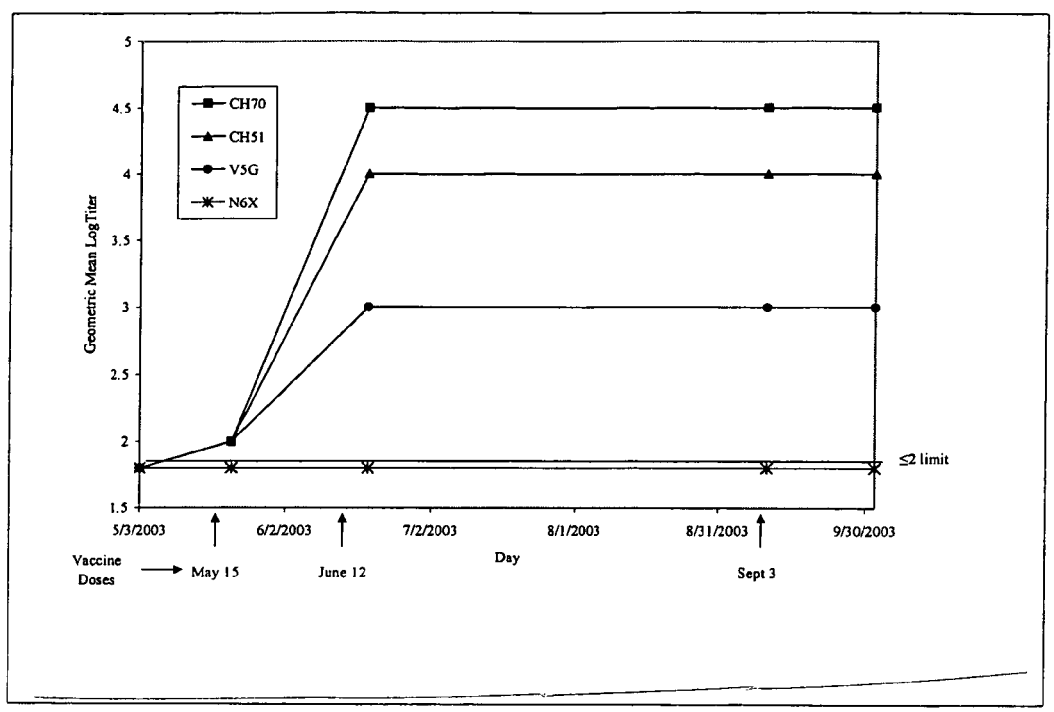
As shown in FIG. 5, serum titers are the geometric mean titer calculated from the sera of Macaca mulatta (rhesus macaque) vaccinated with Venezuelan Eastern Equine replicon expressing Ebola GP prior to challenge and are measured using an ELISA irradiated, sucrose purified Ebola Zaire various as antigen. Control primate had undetectable antibodies at the 1:100 dilution.
Figure 6:
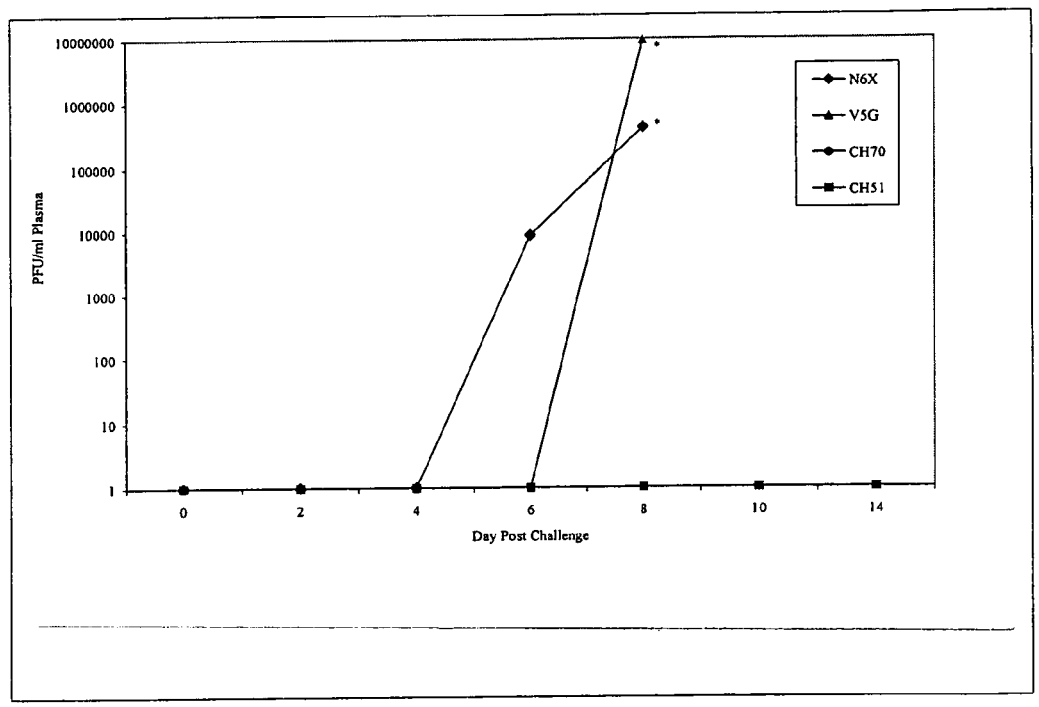
FIG. 6 shows Ebola Viraemia titers in plasma collected at various time points. Values are calculated from plaque counts at various dilutions of plasma used in the assay. Limit of detection was around 30 PFU.

After the final boost, Ebola specific titers varied in each of the three VRP-GP vaccinated primates while no detectable titer was detected in the control primate. CH70, CH51, and V5G had geometric mean titers of 4.5, 3.75, and 3.5 respectively (see FIG. 5). Preliminary data suggest that on day 14 the titers in the surviving animals had increased from those prior to challenge. On day 21, titers have increased to greater than 5.

Cellular Immunity

Cellular immunity was evaluated using ELISpot assays that detect Ebola protein specific lymphocytes that secrete IFN-γ. For ELISpot assays, peripheral blood mononuclear cells (PBMCs) are incubated for 12-24 hours with pools of overlapping peptides that were 15 amino acids in length and overlapped the previous sequence by 10 amino acids. Lymphocytes collected in pre-screening and seven days after the first vaccination and second booster were negative while the positive controls (SEB or PMA and ionomycin) worked properly. In the previous assays, overlapping pools were used and no positives were found, in subsequent assays we ran every GP overlapping peptide individually. On day 56 after the first booster vaccination, we performed a larger bleed to accommodate this analysis. Primate CH51 had a very strong response to #320.V5G, and CH70 had a response to peptide #279 of which only the CH70 response appeared to be significantly higher than background. All four animals appeared to have a response to #150. Leftover cells were restimulated with specific peptides the following day. After an eight day restimulation, individual positive peptides were tested in the ICC assay, with no expansion or positive cell populations noted. The remaining cells were used as effectors in a 51Cr release assay, with frozen pre-vaccination cells as targets, and no specific cell killing was noted. Primates then received a third boost (Sep. 3, 2003) and ELISpot assays were performed seven days later and only CH70 had a detectable response to protein #182. However, again all animals had responses to peptide #166. On Oct. 2, 2003 the animals were analyzed again with all known peptides that were positive at previous time points and no IFN-γ producing cells were detected. The inability to consistently detect cellular responses by ELISpot has been previously observed and may be due to the frequency of GP specific lymphocytes are below the limit of sensitivity of our assay.

Since robust cellular responses should be present in convalescent animals, primates were bled twenty one days after challenge and used the ELISpot assay to detect cellular responses to peptides within Ebola GP as well as NP, VP24, VP30 and VP40. While there appears to be multiple responses to GP, there are responses to other Ebola proteins. For example, both animals had responses to VP24 (CH70 VP24 #18 TIESPLWALRVILAA (SEQ ID NO: 90); CH51 VP24 #47 TQGSSTRMQSLILEF (SEQ ID NO: 61)). CH70 had responses to VP40 (GQPIIPVLLPKYIGL (SEQ ID NO: 92) CH51 had responses to VP35 (#24 and 25 NGLKPVYDMAKTISSLNRVC (SEQ ID NO: 460)). Both animals have responses to multiple pools within the GP peptides and both may have responses to NP. Responses in the VP proteins have been repeated using lymphocytes that have been in culture with IL-2. Since we have inconsistent findings between assays, the current findings must be repeated to confirm that we have specific responses. We may also analyze frozen lymphocytes from earlier time points to look at the kinetics of the responses (days 2, 4, 6, 8, 10, 14).

Post Challenge Observations

Animals were challenged on Oct. 7, 2003, with 1,092 PFU of Ebola Zaire virus. On day six, two animals, V5G and N6X had elevated temperatures and CH51 had a small area (about the size of a quarter) of petechia on the chest area. On day 8, N6X and V5G had elevated temperatures, moderate petechia, and were dehydrated. CH51 did not have elevated temperature at this time point and was eating and drinking. VSG died on day 16 followed by N6X sometime that evening. CH70 and CH50 have survived past the 28 day period set forth in our study. No viremia has been detected in CH70 or CH51. Viremia was detected on day 6 in the control animal and on day 8 in the vaccinated symptomatic animal V5G (See FIG. 2). Tissue viremias (liver and spleens) and liver enzyme function analysis will be completed over the next few weeks. It is interesting to note that while CH51 had some symptoms associated with infection, no viremia has been detected. Furthermore, CH51 has lost weight since the challenge despite having a vigorous appetite.

Conclusions:

VRP-GP can protect rhesus macaques from a 1000 PFU Ebola challenge. To date this is the first successful Ebola VRP vaccination in primates that provided protection and the first that did so with only GP in the vaccine.

The humoral (antibody) response to the vaccine appears to predict protection. In the animal with the highest antibody titer (CH70 ~4.0) no illness was observed, while in the animal with intermediate levels of antibody titer (CH51 3.5) illness was observed but the symptoms resolved. In contrast, the animal with the lowest titer (V5G 3.0) protection was not achieved. Although the cellular responses identified were not consistent, only CH70 had high levels of cellular responses detected, while CH51 had only one response that was significantly higher than background early after the first boost. V5G had no cellular response that was significantly higher than background.

Both cellular and increased antibody responses were detected after challenge. These data suggest that responses to other Ebola proteins can be induced and based on our mouse studies, some of these responses can provide protection. This observation provides further evidence for the use of a cocktail vaccine approach that exposes the vaccine recipient to multiple Ebola proteins would be optimal.

Example 10

Testing in Cynomolgus Macaques

Purpose: Examine the cellular and humoral immune responses to the VRP-GP vaccine and determine the efficacy in monkeys (cynomolgus).

Macaques were vaccinated as above except the regimen was changed to include a fourth shot after several months rest to boost antibody titers.

Figure 7:
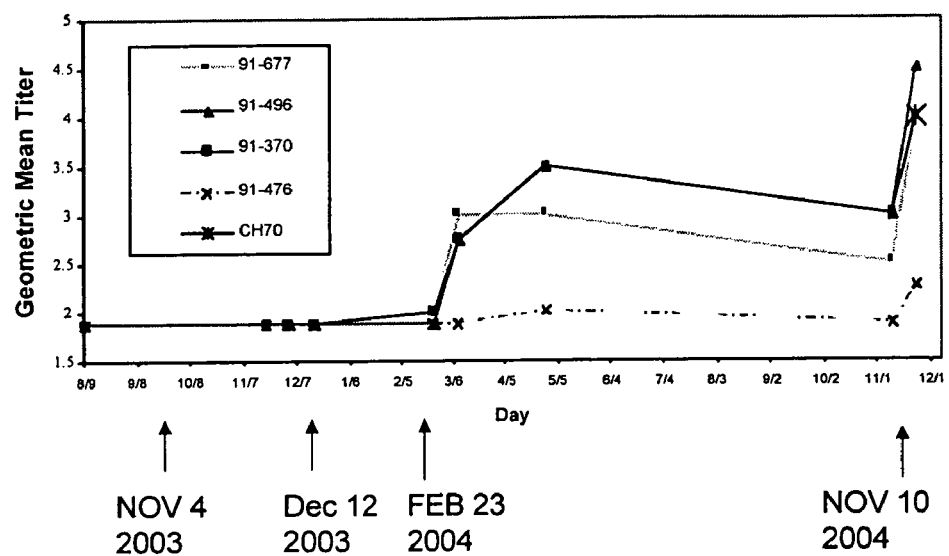
FIG. 7 shows the geometric mean titer in macaques.

Macaques were challenged with 1000 pfu of Ebola Zaire. The control animal was euthanized on day 7 after exhibiting moderate to severe petechia, elevated temperature, dehydration, barely detected respiratory responses and after being observed lying in the cage staring at the ceiling. The vaccinated macaques had no signs of illness for 11 days, at which time 91-370, who had only weak T cell responses before challenge and a lower antibody titer, stopped eating and had a fever. This animal died two days later. The other two animals had no signs of illness after challenge. (See FIG. 7.)

Figure 8:
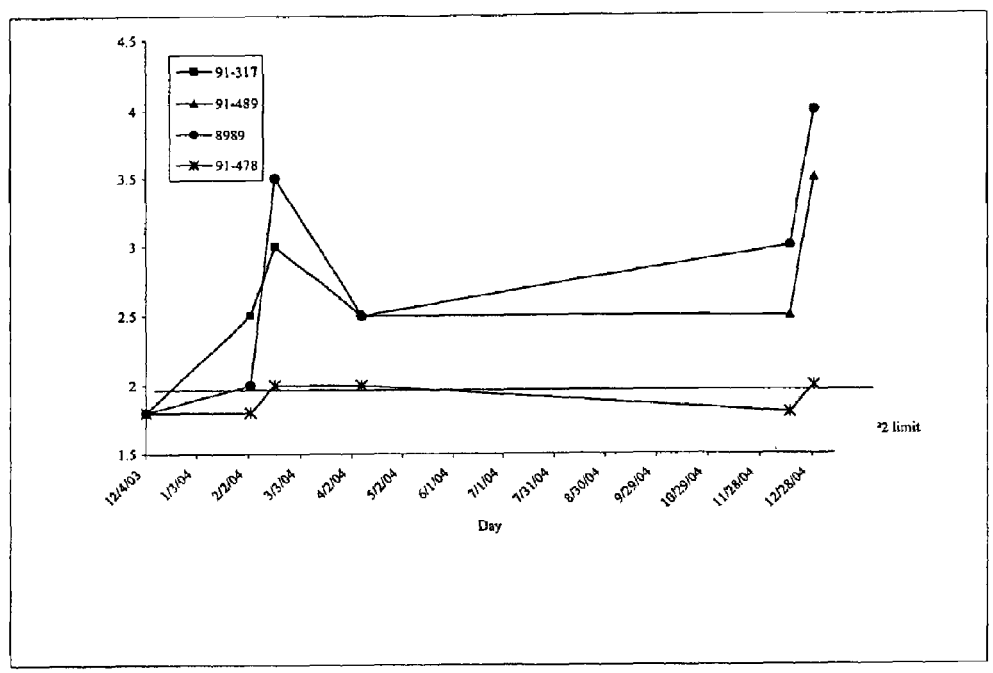
FIG. 8 shows Ebola-specific antibody titers by ELISA. Macaques received VRP expressing GP, NP, VP24, VP30, VP35 and VP40 by the IM route.
Figure 9:
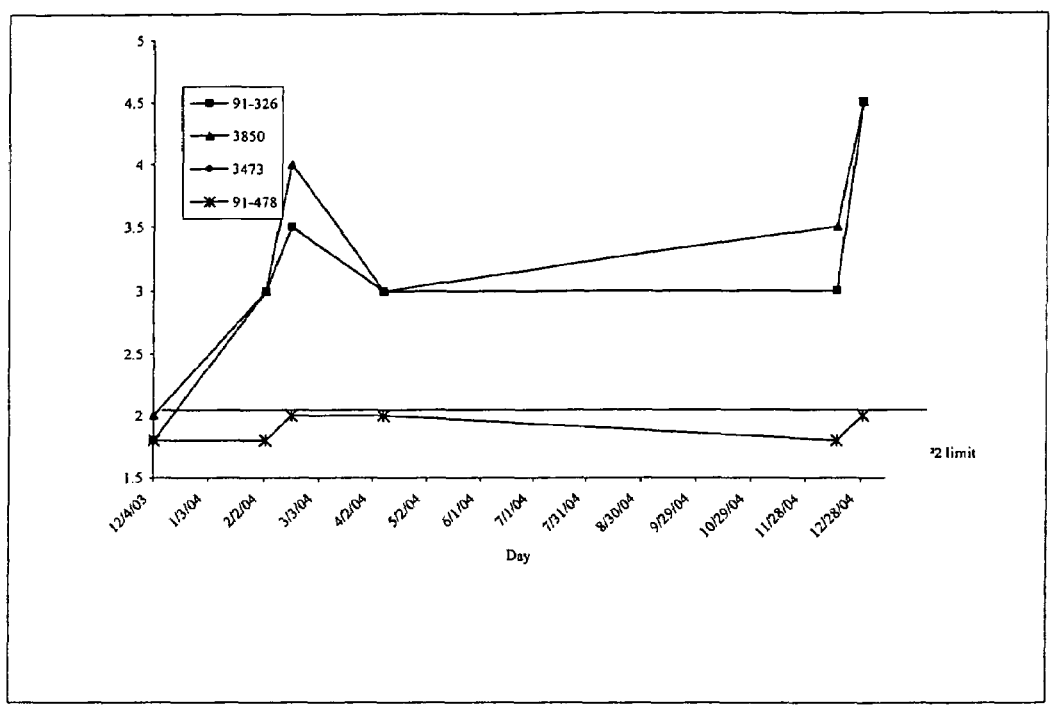
FIG. 9 shows the results of a fourth study which evaluates the mix of VRP administered SC on days 0, 27, 112 and 371.

In a third study, VRP-GP or a mix of VRP expressing GP, NP, VP24, VP30, VP35 and VP40 were administered IM on days 0 (Jan. 6, 2004), 28 (Feb. 3, 2004), 112 (Apr. 28, 2004) and 344 (Dec. 16, 2004). These animals had B cell responses (see FIG. 8) with Ebola-specific Ab titers of approximately 3.5 to 4.5 logs before challenge. Challenge occurred 14 Jan. 2005. The control died on day 9 and some animals had fevers persisting for a few days, but all treated animals survived challenge (as of day 24).

Example 11

Non-Human Primate Ebola Specific T Cell Studies

Purpose: Non-human primates were vaccinated, bled and their T cell responses to the immunogens were assessed using matrixed peptide pools. If they were positive for a pool of peptides, all of the individual sequences in that pool are listed. If the response was narrowed down to a single peptide, that sequence is listed. Also listed after each sequence is what assay was used to find the responses, the date of the assay, the strain of virus used to derive the peptides. Responses are CD8 restricted unless otherwise noted.

Methods

NHP IFN-γ ELISpot

Sterile 96-well Millipore IP plates were coated with 5 ug/ml primary antibody (Mabtech, Cincinnati, Ohio, clone GZ4) diluted in PBS overnight at 4° C. The plates were then washed three times with PBS, and blocked with complete medium (RPMI containing 10% FBS, 2% L-Glutamine, 2% HEPES buffer, 1% Penicillin/Streptomycin) for two hours at 37° C. An input of $1\times10^5$ cells per well were added along with 2 ug/ml of peptide(s), or PMA (25 ng/ml) and ionomycin (1.25 ug/ml) in a total of 100 ul of complete medium. Plates were incubated at 37° C., 6% CO2 for 18-24 hours. After washing the plates eight times with PBS+0.05% Tween-20, goat-anti monkey IFN-□ detecting antibody (Mabtech, clone 7-B6-1) was added to each will at a concentration of 1 ug/ml in PBS+0.05% BSA and incubated 37° C., 5% CO2 for 2 hrs. Plates were then washed six times with PBS, and AEC conjugate (Vector Labs, Burlingame, Calif.) was added and incubated at RT for 1 hr. Plates were washed six times with PBS, and developed with AEC substrate (Vector Labs) for 4 min. Development was stopped by flushing with tap water. Plates were allowed to dry completely, and spots were visualized using the Autoimmune Diagnostika GmbH ELIspot reader (Strasberg, Germany).

NHP Intracellular TFN-α Staining

In a sterile 96-well round bottom plate, PBMC isolated from whole blood were cultured at 37° C. for 4 hrs in the presence of 0.2-2 μg of peptide(s) or PMA (50 ng/ml) and ionomycin (250 ng/ml) in 100 μl complete medium (RPMI, 10% FBS, 2% L-Glutamine, 2% HEPES, 1% P/S). This complete medium also contained 10 μg/ml brefeldin A (BFA, Epicentre Technologies, Madison, Wis.), and 1 ug/ml of CD29, and CD49 co-stimulatory antibodies After culture, the cells stained with anti-CD4 PerCP5.5 or anti-CD8 PECy5 in staining wash buffer ((SWB), PBS, 2% FBS, 0.01% Sodium Azide, (Sigma, St. Louis, Mo.), with BFA (10 ug/ml)). The cells were then fixed in 1% formaldehyde (Ted Pella, Redding, Calif.), permeabilized with SWB containing 0.5% saponin (Sigma, St. Louis, Mo.), and stained with anti-TNFαFITC, and anti-CD69 PE (Pharmingen, San Diego, Calif.). The data were acquired using a FACSCalibur flow cytometer and analyzed with CELLQuest software (Becton-Dickinson Immunocytometry systems, San Jose, Calif.).

NHP Intracellular IFN-γ Staining

PBMC isolated from whole blood were cultured at 37° C. for 4 hours in the presence of 0.2-2 µg of peptide(s) or PMA (50 ng/ml) and ionomycin (250 ng/ml) in 100 µl complete medium (RPMI, 10% FBS, 2% L-Glutamine, 2% HEPES, 1% P/S) containing 10 µg/ml brefeldin A (BFA, Epicentre Technologies, Madison, Wis.), and 1 ug/ml of CD29, and CD49 co-stimulatory antibodies After culture, the cells stained with anti-CD4 PerCP5.5 or anti-CD8 PECy5 in staining Wash Buffer (SWB, PBS, 2% FBS, 0.01% Sodium Azide, Sigma, St. Louis, Mo.), with BFA (10 ug/ml). The cells were then fixed in 1% formaldehyde (Ted Pella, Redding, Calif.), permeabilized with SWB containing 0.5% saponin (Sigma, St. Louis, Mo.), and stained with anti-TNF-a FITC, and anti-CD69 PE (Pharmingen, San Diego, Calif.). The data were acquired using a FACSCalibur flow cytometer and analyzed with CELLQuest software (Becton-Dickinson Immunocytometry systems, San Jose, Calif.).

The following are the T-cell epitopes with positive responses.

CH51 (rhesus macaque, GP VRP)

GP #320 WIPYFGPAAEGIYTE (pre challenge ELISpot, d28 p 1$^{st}$ boost, Z'95) (SEQ ID NO:54)

GP #159 NQLRSVGLNLEGNGV (p challenge ELISpot, ICC Nov. 18, 2003, Z'76, CD4) (SEQ ID NO:55)

GP #172 PDGIRGFPRCRYVHK (p challenge ELISpot, ICC Nov. 18, 2003, Z'76, CD4) (SEQ ID NO:56)

GP #193 EYLFEVDNLTYVQLE (p challenge ELISpot, ICC Nov. 18, 2003, Z'76, CD4) (SEQ ID NO:57)

GP #206 NLTRKIRSEELSFTV (p challenge ELISpot, ICC Nov. 18, 2003, Z'76, CD4) (SEQ ID NO:58)

NP #130 HSFEEMYRHILRSQG (p challenge ELISpot, ICC Nov. 4, 2003, Z'95) (SEQ ID NO:59)

NP #166 NTQSEHSFEEMYRHI (p challenge ELISpot, ICC Nov. 4, 2003, Z'76) (SEQ ID NO:60)

vP24 #47 TQGSSTRMQSLILEF (p challenge ELISpot, ICC Nov. 4, 2003) (SEQ ID NO:61)

vP35 #25 VYDMAKTISSLNRVC (p challenge ELISpot, ICC Nov. 4, 2003) (SEQ ID NO:62)

CH70 (rhesus macaque, GP VRP)

GP #182 FAEGVVAFLILPQAK (pre challenge ELISpot Sep. 11, 2003, Z'76) (SEQ ID NO:63)

GP pool 5 (p challenge ELISpot, Nov. 4, 2003, Z'76)
    #199 YTSGKRSNTTGKLIW (SEQ ID NO:64)
    #200 RSNTTGKLIWKVNPE (SEQ ID NO:65)
    #201 GKLIWKVNPEIDTTI (SEQ ID NO:66)
- #202 KVNPEIDTTIGEWAF (SEQ ID NO:67)
- #203 IDTTIGEWAFWETKK (SEQ ID NO:68)
- #204 GEWAFWETKKNLTRK (SEQ ID NO:69)
- #205 WETKKNLTRKIRSEE (SEQ ID NO:70)
- #206 NLTRKIRSEELSFTV (SEQ ID NO:71)
- #207 IRSEELSFTVVSNGA (SEQ ID NO:72)
- #208 LSFTVVSNGAKNISG (SEQ ID NO:73)
- #209 VSNGAKNISGQSPAR (SEQ ID NO:74)
- #210 KNISGQSPARTSSDP (SEQ ID NO:75)
- #211 QSPARTSSDPGTNTT (SEQ ID NO:76)

GP pool 10 (post challenge ELISpot, Nov. 4, 2003, Z'76)
- #264 NRKAIDFLLQRWGGT (SEQ ID NO:77)
- #265 DFLLQRWGGTCHILG (SEQ ID NO:78)
- #266 RWGGTCHILGPDCCI (SEQ ID NO:79)
- #267 CHILGPDCCIEPHDW (SEQ ID NO:80)
- #268 PDCCIEPHDWTKNIT (SEQ ID NO:81)
- #269 EPHDWTKNITDKIDQ (SEQ ID NO:82)
- #270 TKNITDKIDQIIHDF (SEQ ID NO:83)
- #271 DKIDQIIHDFVDKTL (SEQ ID NO:84)
- #272 IIHDFVDKTLPDQGD (SEQ ID NO:85)
- #273 VDKTLPDQGDNDNWW (SEQ ID NO:86)
- #274 PDQGDNDNWWTGWRQ (SEQ ID NO:87)
- #275 NDNWWTGWRQWIPAG (SEQ ID NO:88)
- #276 TGWRQWIPAGIGVTG (SEQ ID NO:89)

vP24 #18 TIESPLWALRVILAA (post challenge ELISpot, Nov. 4, 2003) (SEQ ID NO:90)

vP40 #156 GQPIIPVLLPKYIGL (post challenge ELISpot, Nov. 4, 2003) (SEQ ID NO:91)

91370 (cynomolgus macaque, GP VRP)

GP #202 KVNPEIDTTIGEWAF (ELISpot Mar. 9, 2004, Z'95) (SEQ ID NO:92)

GP #203 IDTTIGEWAF WETKK (ELISpot Mar. 9, 2004, Z'95) (SEQ ID NO:93)

GP #313 AAGPLKAENTNTSKG (ELISpot Mar. 9, 2004, Z'76) (SEQ ID NO:94)

GP #314 KAENTNTSKGTDLLD (ELISpot Mar. 9, 2004, Z'76) (SEQ ID NO:95)

GP pool 11 (ICC Nov. 24, 2004)
- #277 WIPAGIGVTGVIIAV (Z'76) (SEQ ID NO:96)
- #278 IGVTGVIIAVIALFC (Z'76) (SEQ ID NO:97)
- #279 VIIAVIALFCICKFV (Z'76) (SEQ ID NO:98)
- #280 IIAVIALFCICKFVF (Z'76) (SEQ ID NO:99)
- #301 NLTRKIRSEELSFSA (Z'95) (SEQ ID NO:100)
- #302 IRSEELSFSAVSNRA (Z'95) (SEQ ID NO:101)
- #303 LSFSAVSNRAKNISG (Z'95) (SEQ ID NO: 102)
- #304 VSNRAKNISGQSPAR (Z'95) (SEQ ID NO: 103)
- #305 QGREAAVSHLTTLGT (Z'95) (SEQ ID NO: 104)
- #306 AVSHLTTLGTISTSP (Z'95) (SEQ ID NO:105)
- #307 TTLGTISTSPQPPTT (Z'95) (SEQ ID NO: 106)
- #308 ISTSPQPPTTKPGPD (Z'95) (SEQ ID NO:107)
- #309 QPPTTKPGPDNSTHN (Z'95) (SEQ ID NO:108)

GP pool 12 (ICC Nov. 24, 2004, Z'95)
- #310 TDNDSTASDTPPATT (SEQ ID NO:109)
- #311 TASDTPPATTAAGPL (SEQ ID NO: 110)
- #312 PPATTAAGPLKAENT (SEQ ID NO:111)
- #313 AAGPLKAENTNTSKG (SEQ ID NO: 112)
- #314 KAENTNTSKGTDLLD (SEQ ID NO: 113)
- #315 NTSKGTDLLDPATTT (SEQ ID NO:114)
- #316 TDLLDPATTTSPQNH (SEQ ID NO:115)
- #317 IAGVAGLITGGRRAR (SEQ ID NO:116)
- #318 GLITGGRRARREAIV (SEQ ID NO:117)
- #319 GRRARREAIVNAQPK (SEQ ID NO:118)
- #320 WIPYFGPAAEGIYTE (SEQ ID NO:119)
- #321 GPAAEGIYTEGLMHN (SEQ ID NO:120)
- #322 GIYTEGLMHNQDGLF (SEQ ID NO:121)

GP pool 20 (ICC Nov. 24, 2004)
- #153 FSIPLGVIHNSTLQV (Z'76) (SEQ ID NO: 122)
- #166 VVNYEAGEWAENCYN (Z'76) (SEQ ID NO:123)

179 LYDRLASTVIYRGTT (Z'76) (SEQ ID NO:124)
192 GTNETEYLFEVDNLT (Z'76) (SEQ ID NO: 125)
205 WETKKNLTRKIRSEE (Z'76) (SEQ ID NO:126)
218 QGREAAVSHLTTLAT (Z'76) (SEQ ID NO:127)
231 PSATTAAGPPKAENT (Z'76) (SEQ ID NO:128)
244 IAGVAGLITGGRRTR (Z'76) (SEQ ID NO:129)
257 QDGLICGLRQLANET (Z'76) (SEQ ID NO:130)
270 TKNITDKIDQIIHDF (Z'76) (SEQ ID NO: 131)
303 LSFSAVSNRAKNISG (Z'95) (SEQ ID NO: 132)
316 TDLLDPATTTSPQNH (Z'95) (SEQ ID NO:133)

GP pool 21 (ICC Nov. 24, 2004)
154 GVIHNSTLQVSDVDK (Z'76) (SEQ ID NO:134)
167 AGEWAENCYNLEIKK (Z'76) (SEQ ID NO:135)
180 ASTVIYRGTTFAEGV (Z'76) (SEQ ID NO:136)
193 EYLFEVDNLTYVQLE (Z'76) (SEQ ID NO:137)
205 WETKKNLTRKIRSEE (Z'76) (SEQ ID NO: 138)
219 AVSHLTTLATISTSP (Z'76) (SEQ ID NO:139)
232 AAGPPKAENTNTSKS (Z'76) (SEQ ID NO: 140)
245 GLITGGRRTRREAIV (Z'76) (SEQ ID NO:141)
258 CGLRQLANETTQALQ (Z'76) (SEQ ID NO: 142)
271 DKIDQIIHDFVDKTL (Z'76) (SEQ ID NO:143)
304 VSNRAKNISGQSPAR (Z'95) (SEQ ID NO:144)
317 IAGVAGLITGGRRAR (Z'95) (SEQ ID NO:145)

91496 (cynomolgus macaque, GP VRP)

GP #279 VIIAVIALFCICKFV (ELISpot Mar. 9, 2004, Z'76) (SEQ ID NO:146)

GP pool 12 (ICC Nov. 24, 2004)

(see sequences above)

GP pool 20 (ICC Nov. 24, 2004)

(see sequences above)

91677 (cynomolgus macaque, GP VRP)

GP pool 4 (ICC Nov. 24, 2004, Z'76)
186 SHPLREPVNATEDPS (SEQ ID NO:147)
187 EPVNATEDPSSGYYS (SEQ ID NO:148)
188 TEDPSSGYYSTTIRY (SEQ ID NO:149)
189 SGYYSTTIRYQATGF (SEQ ID NO:150)
190 TTIRYQATGFGTNET (SEQ ID NO:151)
191 QATGFGTNETEYLFE (SEQ ID NO:152)
192 GTNETEYLFEVDNLT (SEQ ID NO:153)
193 EYLFEVDNLTYVQLE (SEQ ID NO:154)
194 VDNLTYVQLESRFTP (SEQ ID NO:155)
195 YVQLESRFTPQFLLQ (SEQ ID NO:156)
196 SRFTPQFLLQLNETI (SEQ ID NO:157)
197 QFLLQLNETIYTSGK (SEQ ID NO:158)
198 LNETIYTSGKRSNTT (SEQ ID NO:159)

GP pool 9 (ICC Nov. 24, 2004, Z'76)
251 QDEGAAIGLAWIPYF (SEQ ID NO:160)
252 AIGLAWIPYFGPAAE (SEQ ID NO:161)
253 WIPYFGPAAEGIYTE (SEQ ID NO:162)
254 GPAAEGIYTEGLMHN (SEQ ID NO: 163)
255 GIYTEGLMHNQDGLI (SEQ ID NO:164)
256 GLMHNQDGLICGLRQ (SEQ ID NO:165)
257 QDGLICGLRQLANET (SEQ ID NO:166)
258 CGLRQLANETTQALQ (SEQ ID NO:167)
259 LANETTQALQLFLRA (SEQ ID NO:168)
260 TQALQLFLRATTELR (SEQ ID NO:169)
261 LFLRATTELRTFSIL (SEQ ID NO:170)
262 TTELRTFSILNRKAI (SEQ ID NO:171)
263 TFSILNRKAIDFLLQ (SEQ ID NO:172)

41132 (cynomolgus macaque, Adeno VRP)

GP pool 1 (ICC Nov. 24, 2004, Z'76)
147 MGVTGILQLPRDRFK (SEQ ID NO:173)
148 ILQLPRDRFKRTSFF (SEQ ID NO:174)
149 RDRFKRTSFFLWVII (SEQ ID NO:175)
150 RTSFFLWVIILFQRT (SEQ ID NO: 176)
151 LWVIILFQRTFSIPL (SEQ ID NO:177)
152 LFQRTFSIPLGVIHN (SEQ ID NO:178)
153 FSIPLGVIHNSTLQV (SEQ ID NO: 179)
154 GVIHNSTLQVSDVDK (SEQ ID NO:180)
155 STLQVSDVDKLVCRD (SEQ ID NO:181)
156 SDVDKLVCRDKLSST (SEQ ID NO:182)
157 LVCRDKLSSTNQLRS (SEQ ID NO:183)
158 KLSSTNQLRSVGLNL (SEQ ID NO:184)
159 LVCRDKLSSTNQLRS (SEQ ID NO:185)

GP pool 11 (ICC Nov. 24, 2004)

(see sequences above)

GP pool 15 (ICC Nov. 24, 2004)
148 ILQLPRDRFKRTSFF (Z'76) (SEQ ID NO: 186)
161 EGNGVATDVPSATKR (Z'76) (SEQ ID NO: 187)
174 RYVHKVSGTGPCAGD (Z'76) (SEQ ID NO:188)
187 EPVNATEDPSSGYYS (Z'76) (SEQ ID NO:189)
200 RSNTTGKLIWKVNPE (Z'76) (SEQ ID NO:190)
213 GTNTTTEDHKIMASE (Z'76) (SEQ ID NO:191)
226 LDISEATQVEQHHRR (Z'76) (SEQ ID NO:192)
239 NNNTHHQDTGEESAS (Z'76) (SEQ ID NO:193)
252 AIGLAWIPYFGPAAE (Z'76) (SEQ ID NO:194)
265 DFLLQRWGGTCHILG (Z'76) (SEQ ID NO:195)
278 IGVTGVIIAVIALFC (Z'76) (SEQ ID NO: 196)
311 TASDTPPATTAAGPL (Z'95) (SEQ ID NO: 197)

GP pool 16 (ICC Nov. 24, 2004)
149 RDRFKRTSFFLWVII (Z'76) (SEQ ID NO:198)
162 ATDVPSATKRWGFRS (Z'76) (SEQ ID NO:199)
175 VSGTGPCAGDFAFHK (Z'76) (SEQ ID NO:200)
188 TEDPSSGYYSTTIRY (Z'76) (SEQ ID NO:201)
201 GKLIWKVNPEIDTTI (Z'76) (SEQ ID NO:202)
214 TEDHKIMASENSSAM (Z'76) (SEQ ID NO:203)
227 ATQVEQHHRRTDNDS (Z'76) (SEQ ID NO:204)
240 HQDTGEESASSGKLG (Z'76) (SEQ ID NO:205)
253 WIPYFGPAAEGIYTE (Z'76) (SEQ ID NO:206)
266 RWGGTCHILGPDCCI (Z'76) (SEQ ID NO:207)
279 VIIAVIALFCICKFV (Z'76) (SEQ ID NO:208)
312 PPATTAAGPLKAENT (Z'95) (SEQ ID NO:209)

GP pool 17 (ICC Nov. 24, 2004)
150 RTSFFLWVIILFQRT (Z'76) (SEQ ID NO:210)
163 SATKRWGFRSGVPPK (Z'76) (SEQ ID NO:211)
176 PCAGDFAFHKEGAFF (Z'76) (SEQ ID NO:212)
189 SGYYSTTIRYQATGF (Z'76) (SEQ ID NO:213)
202 KVNPEIDTTIGEWAF (Z'76) (SEQ ID NO:214)
215 IMASENSSAMVQVHS (Z'76) (SEQ ID NO:215)
228 QHHRRTDNDSTASDT (Z'76) (SEQ ID NO:216)
241 EESASSGKLGLITNT (Z'76) (SEQ ID NO:217)
254 GPAAEGIYTEGLMHN (Z'76) (SEQ ID NO:218)
267 CHILGPDCCIEPHDW (Z'76) (SEQ ID NO:219)
280 IIAVIALFCICKFVF (Z'76) (SEQ ID NO:220)
313 AAGPLKAENTNTSKG (Z'95) (SEQ ID NO:221)

41148 (cynomolgus macaque, Adeno VRP)

GP pool 9 (ICC Nov. 24, 2004)

(see sequences above)

3850 (cynomolgus macaque, Cocktail VRPs)

GP pool 11 (ICC May 18, 2004, CD4)

(see sequences above)

GP pool 1 (ICC May 18, 2004)

(see sequences above)

0

GP pool 11 (ICC May 18, 2004)

(see sequences above)

GP pool 17 (ICC May 27, 2004)

(see sequences above)

NP Pool 21
  NP#8 VRQRVIPVYQVNNLE (SEQ ID NO:222)
  NP#21 GHGFRFEVKKRDGVK (SEQ ID NO:223)
  NP#34 KACLEKVQRQIQVHA (SEQ ID NO:224)
  NP#47 VISNSVAQARFSGLL (SEQ ID NO:225)
  NP#60 FARLLNLSGVNNLEH (SEQ ID NO:226)
  NP#73 RELDHLGLDDQEKKI (SEQ ID NO:227)
  NP#86 DIPFPGPINDDDNPG (SEQ ID NO:228)
  NP#99 DDEDTKPVPNRSTKG (SEQ ID NO:229)
  NP#112 STSPRMLTPINEEAD (SEQ ID NO:230)
  NP#125 PQDEQQDQDHTQEAR (SEQ ID NO:231)
  NP#138 YTYPDSLEEEYPPWL (SEQ ID NO:232)
  NP#285 LVVGEKACLEKVQRQ (SEQ ID NO:233)
  NP#298 TQEARNQDSDNTQPE (SEQ ID NO:234)

VP30 pool 5
  VP30 #536 TIEDSKLRALLTLCA (SEQ ID NO:235)
  VP30 #537 KLRALLTLCAVMTRK (SEQ ID NO:236)
  VP30 #538 LTLCAVMTRKFSKSQ (SEQ ID NO:237)
  VP30 #539 VMTRKFSKSQLSLLC (SEQ ID NO:238)
  VP30 #540 FSKSQLSLLCETHLR (SEQ ID NO:239)
VP30 #541 LSLLCETHLRREGLG (SEQ ID NO:240)
VP30 #542 ETHLRREGLGQDQAE (SEQ ID NO:241)
VP30 #543 REGLGQDQAEPVLEV (SEQ ID NO:242)

VP35 #372 GTAFHQLVQVICKLG (SEQ ID NO:243)

vP40 pool 2 (ICC May 18, 2004, CD4)
108 SVNGDTPSNPLRPIA (SEQ ID NO:244)
109 TPSNPLRPIADDTID (SEQ ID NO:245)
110 LRPIADDTIDHASHT (SEQ ID NO:246)
111 DDTIDHASHTPGSVS (SEQ ID NO:247)
112 HASHTPGSVSSAFIL (SEQ ID NO:248)
113 PGSVSSAFILEAMVN (SEQ ID NO:249)
114 SAFILEAMVNVISGP (SEQ ID NO:250)
115 EAMVNVISGPKVLMK (SEQ ID NO:251)

vP40 pool 6 (ICC May 18, 2004, CD4)
140 GALRPGISFHPKLRP (SEQ ID NO:252)
141 GISFHPKLRPILLPN (SEQ ID NO:253)
142 PKLRPILLPNKSGKK (SEQ ID NO:254)
143 ILLPNKSGKKGNSAD (SEQ ID NO:255)
144 KSGKKGNSADLTSPE (SEQ ID NO:256)
145 GNSADLTSPEKIQAI (SEQ ID NO:257)
146 LTSPEKIQAIMTSLQ (SEQ ID NO:258)
147 KIQAIMTSLQDFKIV (SEQ ID NO:259)

vP40 pool 9 (ICC May 18, 2004, CD4)
100 MRRVILPTAPPEYME (SEQ ID NO:260)
108 SVNGDTPSNPLRPIA (SEQ ID NO:261)
116 VISGPKVLMKQIPIW (SEQ ID NO:262)
124 TITHFGKATNPLVRV (SEQ ID NO:263)
132 FVLPPVQLPQYFTFD (SEQ ID NO:264)
140 GALRPGISFHPKLRP (SEQ ID NO:265)
148 MTSLQDFKIVPIDPT (SEQ ID NO:266)
156 GQPIIPVLLPKYIGL (SEQ ID NO:267)

vP40 pool 12 (ICC May 18, 2004, CD4)
103 AIYPVRSNSTIARGG (SEQ ID NO:268)
111 DDTIDHASHTPGSVS (SEQ ID NO:269)
119 LPLGVADQKTYSFDS (SEQ ID NO:270)
127 NRLGPGIPDHPLRLL (SEQ ID NO:271)
135 LTALKLITQPLPAAT (SEQ ID NO:272)
143 ILLPNKSGKKGNSAD (SEQ ID NO:273)
151 KNIMGIEVPETLVHK (SEQ ID NO:274)
159 DPVAPGDLTMVITQD (SEQ ID NO:275)

91326 (cynomolgus macaque, Cocktail VRPs)

GP pool 11 (ICC May 20, 2004)

(see sequences above)

GP pool 15 (ICC May 20, 2004)

(see sequences above)

GP pool 15 (ICC May 20, 2004, CD4)

(see sequences above)

GP pool 16 (ICC May 20, 2004, CD4)

(see sequences above)

GP pool 17 (ICC May 20, 2004, CD4)

(see sequences above)

GP pool 18 (ICC May 20, 2004, CD4)
151 LWVIILFQRTFSIPL (Z'76) (SEQ ID NO:276)
164 WGFRSGVPPKVVNYE (Z'76) (SEQ ID NO:277)
177 FAFHKEGAFFLYDRL (Z'76) (SEQ ID NO:278)
190 TTIRYQATGFGTNET (Z'76) (SEQ ID NO:279)
203 IDTTIGEWAFWETKK (Z'76) (SEQ ID NO:280)
216 NSSAMVQVHSQGREA (Z'76) (SEQ ID NO:281)
229 TDNDSTASDTPSATT (Z'76) (SEQ ID NO:282)
242 SGKLGLITNTIAGVA (Z'76) (SEQ ID NO:283)
255 GIYTEGLMHNQDGLI (Z'76) (SEQ ID NO:284)
268 PDCClEPHDWTKNIT (Z'76) (SEQ ID NO:285)
301 NLTRKIRSEELSFSA (Z'95) (SEQ ID NO:286)
314 KAENTNTSKGTDLLD (Z'95) (SEQ ID NO:287)

GP pool 19 (ICC May 20, 2004, CD4)
152 LFQRTFSIPLGVIHN (Z'76) (SEQ ID NO:288)
165 GVPPKVVNYEAGEWA (Z'76) (SEQ ID NO:289)
178 EGAFFLYDRLASTVI (Z'76) (SEQ ID NO:290)
191 QATGFGTNETEYLFE (Z'76) (SEQ ID NO:291)
204 GEWAFWETKKNLTRK (Z'76) (SEQ ID NO:292)
217 VQVHSQGREAAVSHL (Z'76) (SEQ ID NO:293)
230 TASDTPSATTAAGPP (Z'76) (SEQ ID NO:294)
243 LITNTIAGVAGLITG (Z'76) (SEQ ID NO:295)
256 GLMHNQDGLICGLRQ (Z'76) (SEQ ID NO:296)
269 EPHDWTKNITDKIDQ (Z'76) (SEQ ID NO:297)
302 IRSEELSFSAVSNRA (Z'95) (SEQ ID NO:298)
315 NTSKGTDLLDPATTT (Z'95) (SEQ ID NO:299)

GP pool 20 (ICC May 20, 2004, CD4)

(see sequences above)

vP24 pool 3 (ICC May 20, 2004, CD4)
405 MTRNLFPHLFQNPNS (SEQ ID NO:300)
406 FPHLFQNPNSTIESP (SEQ ID NO:301)
407 QNPNSTIESPLWALR (SEQ ID NO:302)
408 TIESPLWALRVILLA (SEQ ID NO:303)
409 LWALRVILLAGIQDQ (SEQ ID NO:304)
410 VILLAGIQDQLIDQS (SEQ ID NO:305)
411 GIQDQLIDQSLIEPL (SEQ ID NO:306)

vP24 pool 4 (ICC May 20, 2004, CD4)
  #412 LIDQSLIEPLAGALG (SEQ ID NO:307)
  #413 LIEPLAGALGLISDW (SEQ ID NO:308)
  #414 AGALGLISDWLLTTN (SEQ ID NO:309)
  #415 LISDWLLTTNTNHFN (SEQ ID NO:310)
  #416 LLTTNTNHFNMRTQR (SEQ ID NO:311)
  #417 TNHFNMRTQRVKEQL (SEQ ID NO:312)
  #418 MRTQRVKEQLSLKML (SEQ ID NO:313)

vP24 pool 5
  vP24 #419 VKEQLSLKMLSLIRS (SEQ ID NO:314)
  vP24 #420 SLKMLSLIRSNILKF (SEQ ID NO:315)
  vP24 #421 SLIRSNILKFINKLD (SEQ ID NO:316)
  vP24 #422 NILKFINKLDALHVV (SEQ ID NO:317)
  vP24 #423 INKLDALHVVNYNGL (SEQ ID NO:318)
  vP24 #424 ALHVVNYNGLLSSIE (SEQ ID NO:319)
vP24 #425 NYNGLLSSIEIGTQN (SEQ ID NO:320)

vP24 pool 12 (ICC May 20, 2004, CD4)
395 VVLSDLCNFLVSQTI (SEQ ID NO:321)
402 LLHRLKTNDFAPAWS (SEQ ID NO:322)
409 LWALRVILLAGIQDQ (SEQ ID NO:323)
416 LLTTNTNHFNMRTQR (SEQ ID NO:324)
423 INKLDALHVVNYNGL (SEQ ID NO:325)
430 GFLVELQEPDKSAMN (SEQ ID NO:326)
437 TQGSSTRMQSLILEF (SEQ ID NO:327)

vP24 pool 13 (ICC May 20, 2004, CD4)
396 LCNFLVSQTIQGWKV (SEQ ID NO:328)
403 KTNDFAPAWSMTRNL (SEQ ID NO:329)
410 VILLAGIQDQLIDQS (SEQ ID NO:330)
417 TNHFNMRTQRVKEQL (SEQ ID NO:331)
424 ALHVVNYNGLLSSEI (SEQ ID NO:332)
431 LQEPDKSAMNRMKPG (SEQ ID NO:333)
438 TRMQSLILEFNSSLA (SEQ ID NO:334)

vP30 pool 12
vP30 #507 HSRDGHDHHHVRARSS (SEQ ID NO:335)
vP30 #515 KKRVEPLTVPPAPKD (SEQ ID NO:336)
vP30 #523 TDRELLLLIARKTCG (SEQ ID NO:337)
vP30 #531QEEGPKITLLTLIKT (SEQ ID NO:338)
vP30 #539 VMTRKFSKSQLSLLC (SEQ ID NO:339)
vP30 #547 SDKGGSFEAALWQQW (SEQ ID NO:340)
vP30 #555 VVVSGLRTLVPQSDN (SEQ ID NO:341)

vP30 pool 13 (ICC May 20, 2004, CD4)
508 HDHHVRARSSRENY (SEQ ID NO:342)
516 PLTVPPAPKDICPTL (SEQ ID NO:343)
524 LLLIARKTCGSVEQQ (SEQ ID NO:344)
532 KITLLTLIKTAEHWA (SEQ ID NO:345)
540 FSKSQLSLLCETHLR (SEQ ID NO:346)
548 SFEAALWQQWDRQSL (SEQ ID NO:347)

556 LRTLVPQSDNEEAST (SEQ ID NO:348)

vP35 #372 (see sequence above)

vP40 pool 10 (ICC May 20, 2004, CD4)
441 LPTAPPEYMEAIYPV (SEQ ID NO:349)
449 TPSNPLRPIADDTID (SEQ ID NO:350)
457 KVLMKQIPIWLPLGV (SEQ ID NO:351)
465 GKATNPLVRVNRLGP (SEQ ID NO:352)
473 VQLPQYFTFDLTALK (SEQ ID NO:353)
481 GISFHPKLRPILLPN (SEQ ID NO:354)
489 DFKIVPIDPTKNIMG (SEQ ID NO:355)
497 PVLLPKYIGLDPVAP (SEQ ID NO:356)

vP40 pool 14 (ICC May 20, 2004, CD4)
445 IARGGNSNTGFLTPE (SEQ ID NO:357)
453 PGSVSSAFILEAMVN (SEQ ID NO:358)
461 YSFDSTTAAIMLASY (SEQ ID NO:359)
469 PLRLLRIGNQAFLQE (SEQ ID NO:360)
477 LPAATWTDDTPTGSN (SEQ ID NO:361)
485 GNSADLTSPEKIQAI (SEQ ID NO:362)
493 TLVHKLTGKKVTSKN (SEQ ID NO:363)
501 VITQDCDTCHSPASL (SEQ ID NO:364)

3473 (cynomolgus macaque, Cocktail VRPs)

GP pool 1 (ICC May 21, 2004)

(see sequences above)

GP pool 11 (ICC May 21, 2004)

(see sequences above)

GP pool 15 (ICC May 21, 2004)

(see sequences above)

GP pool 1 (ICC May 21, 2004, CD4)

(see sequences above)

GP pool 11 (ICC May 21, 2004, CD4)

(see sequences above)

GP pool 14 (ICC May 21, 2004, CD4)
147 MGVTGILQLPRDRFK (Z'76) (SEQ ID NO:365)
160 VGLNLEGNGVATDVP (Z'76) (SEQ ID NO:366)
173 GFPRCRYVHKVSGTG (Z'76) (SEQ ID NO:367)
186 SHPLREPVNATEDPS (Z'76) (SEQ ID NO:368)
199 YTSGKRSNTTGKLIW (Z'76) (SEQ ID NO:369)
212 TSSDPGTNTTTEDHK (Z'76) (SEQ ID NO:370)
225 TPVYKLDISEATQVE (Z'76) (SEQ ID NO:371)
238 SETAGNNNTHHQDTG (Z'76) (SEQ ID NO:372)
251 QDEGAAIGLAWIPYF (Z'76) (SEQ ID NO:373)
264 NRKAIDFLLQRWGGT (Z'76) (SEQ ID NO:374)
277 WIPAGIGVTGVIIAV (Z'76) (SEQ ID NO:375)
310 TDNDSTASDTPPATT (Z'95) (SEQ ID NO:376)
323 GLMHNQDGLFCGLRQ (Z'95) (SEQ ID NO:377)

GP pool 15 (ICC May 21, 2004, CD4)

(see sequences above)

vP24 pool 6 (ICC May 21, 2004)

vP24 pool 13 (ICC May 21, 2004)

(see sequences above)

vP30 pool 4 (ICC May 21, 2004)
528 PKDSRLANPTADDFQ (SEQ ID NO:378)
529 LANPTADDFQQEEGP (SEQ ID NO:379)
530 ADDFQQEEGPKITLL (SEQ ID NO:380)
531 QEEGPKITLLTLIKT (SEQ ID NO:381)
532 KITLLTLIKTAEHWA (SEQ ID NO:382)
533 TLIKTAEHWARQDIR (SEQ ID NO:383)
534 AEHWARQDIRTIEDS (SEQ ID NO:384)
535 RQDIRTIEDSKLRAL (SEQ ID NO:385)

vP30 pool 12
(see sequences above)

vP35 pool 2 (ICC May 21, 2004)
333 SDIFCDIENNPGLCY (SEQ ID NO:386)
334 DIENNPGLCYASQMQ (SEQ ID NO:387)
335 PGLCYASQMQQTKPN (SEQ ID NO:388)
336 ASQMQQTKPNPKTRN (SEQ ID NO:389)
337 QTKPNPKTRNSQTQT (SEQ ID NO:390)
338 PKTRNSQTQTDPICN (SEQ ID NO:391)
339 SQTQTDPICNHSFEE (SEQ ID NO:392)
340 DPICNHSFEEVVQTL (SEQ ID NO:393)

vP35 pool 3
    VP35 #341 HSFEEVVQTLASLAT (SEQ ID NO:394)
    VP35 #342 VVQTLASLATVVQQQ (SEQ ID NO:395)
    VP35 #343 ASLATVVQQQTIASE (SEQ ID NO:396)
    VP35 #344 VVQQQTIASESLEQR (SEQ ID NO:397)
    VP35 #345 TIASESLEQRITSLE (SEQ ID NO:398)
    VP35 #346 SLEQRITSLENGLKP (SEQ ID NO:399)
    VP35 #347 ITSLENGLKPVYDMA (SEQ ID NO:400)
    VP35 #348 NGLKPVYDMAKTISS (SEQ ID NO:401)

vP35 pool 6 (ICC May 21, 2004)
    #365 NNLNSTTSLTEENFG (SEQ ID NO:402)
    #366 TTSLTEENFGKPDIS (SEQ ID NO:403)
    #367 EENFGKPDISAKDLR (SEQ ID NO:404)
    #368 KPDISAKDLRNIMYD (SEQ ID NO:405)
    #369 AKDLRNIMYDHLPGF (SEQ ID NO:406)
    #370 NIMYDHLPGFGTAFH (SEQ ID NO:407)
    #371 HLPGFGTAFHQLVQV (SEQ ID NO:408)
    #372 GTAFHQLVQVICKLG (SEQ ID NO:409)

vP35 pool 12 (ICC May 21, 2004)
    #327 TAATTQNDRMPGPEL (SEQ ID NO:410)
    #335 PGLCYASQMQQTKPN (SEQ ID NO:411)
    #343 ASLATVVQQQTIASE (SEQ ID NO:412)
    #351 LNRVCAEMVAKYDLL (SEQ ID NO:413)
    #359 PGPSLYEESAIRGKI (SEQ ID NO:414)
    #367 EENFGKPDISAKDLR (SEQ ID NO:415)
    #375 KDSNSLDIIHAEFQA (SEQ ID NO:416)
    #383 APPVIHIRSRGDIPR (SEQ ID NO:417)

60143 (cynomolgus macaque, Cocktail VRPs)

GP pool 23 (ICC Jun. 4, 2004)
    #156 SDVDKLVCRDKLSST (Z'76) (SEQ ID NO:418)
    #169 LEIKKPDGSECLPAA (Z'76) (SEQ ID NO:419)
    #182 FAEGVVAFLILPQAK (Z'76) (SEQ ID NO:420)
    #195 YVQLESRFTPQFLLQ (Z'76) (SEQ ID NO:421)
    #208 LSFTVVSNGAKNISG (Z'76) (SEQ ID NO:422)
    #221 ISTSPQSLTTKPGPD (Z'76) (SEQ ID NO:423)
    #234 NTSKSTDFLDPATTT (Z'76) (SEQ ID NO:424)
    #247 REAIVNAQPKCNPNL (Z'76) (SEQ ID NO:425)
    #260 TQALQLFLRATTELR (Z'76) (SEQ ID NO:426)
    #273 VDKTLPDQGDNDNWW (Z'76) (SEQ ID NO:427)
    #306 AVSHLTTLGTISTSP (Z'95) (SEQ ID NO:428)
    #319 GRRARREAIVNAQPK (Z'95) (SEQ ID NO:429)

vP35 pool 16 (ICC Jun. 4, 2004)
    #331 EQLMTGRIPVSDIFC (SEQ ID NO:430)
    #339 SQTQTDPICNHSFEE (SEQ ID NO:431)
    #347 ITSLENGLKPVYDMA (SEQ ID NO:432)
    #355 RATATAAATEAYWAE (SEQ ID NO:433)
    #363 TVPQSVREAFNNLNS (SEQ ID NO:434)
    #371 HLPGFGTAFHQLVQV (SEQ ID NO:435)
    #379 DSPQCALIQITKRVP (SEQ ID NO:436)
    #387 LRPVPPSPKIDRGWV (SEQ ID NO:437)

vP40 pool 16 (ICC Jun. 4, 2004)
    #447 FLTPESVNGDTPSNP (SEQ ID NO:438)
    #455 EAMVNVISGPKVLMK (SEQ ID NO:439)
    #463 MLASYTITHFGKATN (SEQ ID NO:440)
    #471 AFLQEFVLPPVQLPQ (SEQ ID NO:441)
    #479 PTGSNGALRPGISFH (SEQ ID NO:442)
    #487 KIQAIMTSLQDFKIV (SEQ ID NO:443)
    #495 VTSKNGQPIIPVLLP (SEQ ID NO:444)
    #503 DTCHSPASLPAVIEK (SEQ ID NO:445)

99217 (cynomolgus macaque, Cocktail VRPs)

GP pool 23 (ICC Jun. 4, 2004)

(see sequences above)

NP pool 24 (ICC Jun. 4, 2004)
    #11 EICQLIIQAFEAGVD (SEQ ID NO:446)
    #24 RLEELLPAVSSGKNI (SEQ ID NO:447)
    #37 EQGLIQYPTAWQSVG (SEQ ID NO:448)
    #50 IVKTVLDHILQKTER (SEQ ID NO:449)
    #63 GLFPQLSAIALGVAT (SEQ ID NO:450)
    #76 LMNFHQKKNEISFQQ (SEQ ID NO:451)
    #89 HQDDDPTDSQDTTIP (SEQ ID NO:452)
    #102 GQQKNSQKGQHIEGR (SEQ ID NO:453)
    #115 PLDDADDETSSLPPL (SEQ ID NO:454)
    #128 NQDSDNTQSEHSFEE (SEQ ID NO:455)
    #141 TEKEAMNEENRFVTL (SEQ ID NO:456)
    #288 AKVKNEVNSFLAALS (SEQ ID NO:457)

vP35 pool 9 (ICC Jun. 4, 2004)
    #389 DRGWVCVFQLQDGKT (SEQ ID NO:458)
    #390 CVFQLQDGKTLGLKI (SEQ ID NO:459)

The following are DNA and amino acid sequences referred to in the text above.

```
<210> 1
<211> 2298
<212> DNA
<213> Ebola zaire

<400> 1
atcgataagc tcggaattcg agctcgcccg gggatcctct agagtcgaca acaacacaat
60 gggcgttaca ggaatattgc agttacctcg tgatcgattc aagaggacat cattctttct
120 ttgggtaatt atccttttcc aaagaacatt ttccatccca cttggagtca tccacaatag
180 cacattacag gttagtgatg tcgacaaact agtttgtcgt gacaaactgt catccacaaa
240 tcaattgaga tcagttggac tgaatctcga agggaatgga gtggcaactg acgtgccatc
300 tgcaactaaa agatgggggct tcaggtccgg tgtcccacca aggtggtca attatgaagc
360
```

-continued

```
tggtgaatgg gctgaaaact gctacaatct tgaaatcaaa aaacctgacg ggagtgagtg
420 tctaccagca gcgccagacg ggattcgggg cttccccgg tgccggtatg tgcacaaagt
480 atcaggaacg ggaccgtgtg ccggagactt tgccttccat aaagagggtg ctttcttcct
540 gtatgatcga cttgcttcca cagttatcta ccgaggaacg actttcgctg aaggtgtcgt
600 tgcatttctg atactgcccc aagctaagaa ggacttcttc agctcacacc ccttgagaga
660 gccggtcaat gcaacggagg acccgtctag tggctactat tctaccacaa ttagatatca
720 ggctaccggt tttggaacca atgagacaga gtacttgttc gaggttgaca atttgaccta
780 cgtccaactt gaatcaagat tcaccacca gtttctgctc cagctgaatg agacaatata
840 tacaagtggg aaaaggagca ataccacggg aaaactaatt tggaaggtca accccgaaat
900 tgatacaaca atcggggagt gggccttctg ggaaactaaa aaaaacctca ctagaaaaat
960 tcgcagtgaa gagttgtctt tcacagttgt atcaaacgga gccaaaaaca tcagtggtca
1020 gagtccggcg cgaacttctt ccgacccagg gaccaacaca acaactgaag accacaaaat
1080 catggcttca gaaaattcct ctgcaatggt tcaagtgcac agtcaaggaa gggaagctgc
1140 agtgtcgcat ctaacaaccc ttgccacaat ctccacgagt ccccaatccc tcacaaccaa
1200 accaggtccg gacaacagca cccataatac acccgtgtat aaacttgaca tctctgaggc
1260 aactcaagtt gaacaagatc accgcagaac agacaacgac agcacagcct ccgacactcc
1320 ctctgccacg accgcagccg accccaaa agcagagaac accaacacga gcaagagcac
1380 tgacttcctg gaccccgcca ccacaacaag tccccaaaac cacagcgaga ccgctggcaa
1440 caacaacact catcaccaag ataccggaga agagagtgcc agcagcggga agctaggctt
1500 aattaccaat actattgctg gagtcgcagg actgatcaca ggcgggagaa gaactcgaag
1560 agaagcaatt gtcaatgctc aacccaaatg caaccctaat ttacattact ggactactca
1620 ggatgaaggt gctgcaatcg gactggcctg gataccatat ttcgggccag cagccgaggg
1680 aatttacata gagggggctaa tgcacaatca agatggttta atctgtgggt tgagacagct
1740 ggccaacgag acgactcaag ctcttcaact gttcctgaga gccacaactg agctacgcac
1800 cttttcaatc ctcaaccgta aggcaattga tttcttgctg cagcgatggg gcggcacatg
1860 ccacattctg ggaccggact gctgtatcga accacatgat tggaccaaga acataacaga
1920 caaaattgat cagattattc atgattttgt tgataaaacc cttccggacc aggggggacaa
```

-continued

```
                                                                    1980
tgacaattgg tggacaggat ggagacaatg gataccggca ggtattggag ttacaggcgt
                                                                    2040 tgtaattgca gttatcgctt tattctgtat atgcaaattt gtcttttagt ttttcttcag
                                                                    2100 attgcttcat ggaaaagctc agcctcaaat caatgaaacc aggatttaat tatatggatt
                                                                    2160 acttgaatct aagattactt gacaaatgat aatataatac actggagctt taaacatagc
                                                                    2220 caatgtgatt ctaactcctt taaactcaca gttaatcata acaaggtttt gagtcgacct
                                                                    2280 gcagccaagc ttatcgat
                   2298

<210> 2
<211> 2428
<212> DNA
<213> Ebola zaire

<400> 2
atcgataagc ttggctgcag gtcgactcta aggatccga gtatggattc tcgtcctcag
                                                                    60 aaaatctgga tggcgccgag tctcactgaa tctgacatgg attaccacaa gatcttgaca
                                                                    120 gcaggtctgt ccgttcaaca ggggattgtt cggcaaagag tcatcccagt gtatcaagta
                                                                    180 aacaatcttg aagaaatttg ccaacttatc atacaggcct ttgaagcagg tgttgatttt
                                                                    240 caagagagtg cggacagttt ccttctgatg ctttgtcttc atcatgcgta ccagggagat
                                                                    300 tacaaacttt tcttggaaag tggcgcagtc aagtatttgg aagggcacgg gttccgtttt
                                                                    360 gaagtcaaga agcgtgatgg agtgaagcga cttgaggaat gctgccagc agtatctagt
                                                                    420 ggaaaaaaca ttaagagaac acttgctgcc atgccggaag aggagacaac tgaagctaat
                                                                    480 gccggtcagt ttctctcctt tgcaagtcta ttccttccga aattggtagt aggagaaaag
                                                                    540 gcttgccttg agaaggttca aaggcaaatt caagtacatg cagagcaagg actgatacaa
                                                                    600 tatccaacag cttggcaatc agtaggacac atgatggtga ttttccgttt gatgcgaaca
                                                                    660 aattttctga tcaaatttct cctaatacac caagggatgc acatggttgc cgggcatgat
                                                                    720 gccaacgatg ctgtgatttc aaattcagtg ctcaagctc gttttttcagg cttattgatt
                                                                    780 gtcaaaacag tacttgatca tatcctacaa aagacagaac gaggagttcg tctccatcct
                                                                    840 cttgcaagga ccgccaaggt aaaaaatgag gtgaactcct ttaaggctgc actcagctcc
                                                                    900 ctggccaagc atggagagta tgctcctttc gcccgacttt tgaaccttc tggagtaaat
                                                                    960 aatcttgagc atggtctttt ccctcaacta tcggcaattg cactcggagt cgccacagca
                                                                    1020 cacgggagta ccctcgcagg agtaaatgtt ggagaacagt atcaacaact cagagaggct
                                                                    1080
```

-continued

```
gccactgagg ctgagaagca actccaacaa tatgcagagt ctcgcgaact tgaccatctt
1140 ggacttgatg atcaggaaaa gaaaattctt atgaacttcc atcagaaaaa gaacgaaatc
1200 agcttccagc aaacaaacgc tatggtaact ctaagaaaag agcgcctggc caagctgaca
1260 gaagctatca ctgctgcgtc actgcccaaa acaagtggac attacgatga tgatgacgac
1320 attcccttc caggacccat caatgatgac gacaatccta gccatcaaga tgatgatccg
1380 actgactcac aggatacgac cattcccgat gtggtggttg atcccgatga tggaagctac
1440 ggcgaatacc agagttactc ggaaaacggc atgaatgcac cagatgactt ggtcctattc
1500 gatctagacg aggacgacga ggacactaag ccagtgccta atagatcgac caagggtgga
1560 caacagaaga acagtcaaaa gggccagcat atagagggca gacagacaca atccaggcca
1620 attcaaaatg tcccaggccc tcacagaaca atccaccacg ccagtgcgcc actcacggac
1680 aatgacagaa gaaatgaacc ctccggctca accagccctc gcatgctgac accaattaac
1740 gaagaggcag acccactgga cgatgccgac gacgagacgt ctagccttcc gcccttggag
1800 tcagatgatg aagagcagga cagggacgga acttccaacc gcacacccac tgtcgcccca
1860 ccggctcccg tatacagaga tcactctgaa aagaaagaac tcccgcaaga cgagcaacaa
1920 gatcaggacc acactcaaga ggccaggaac caggacagtg acaacaccca gtcagaacac
1980 tcttttgagg agatgtatcg ccacattcta agatcacagg ggccatttga tgctgttttg
2040 tattatcata tgatgaagga tgagcctgta gttttcagta ccagtgatgg caaagagtac
2100 acgtatccag actcccttga agaggaatat ccaccatggc tcactgaaaa agaggctatg
2160 aatgaagaga atagatttgt tacattggat ggtcaacaat tttattggcc ggtgatgaat
2220 cacaagaata aattcatggc aatcctgcaa catcatcagt gaatgagcat ggaacaatgg
2280 gatgattcaa ccgacaaata gctaacatta gtagtccag gaacgaaaac aggaagaatt
2340 tttgatgtct aaggtgtgaa ttattatcac aataaaagtg attcttattt ttgaatttgg
2400 gcgagctcga attcccgagc ttatcgat
2428

<210> 3
<211> 847
<212> DNA
<213> Ebola zaire

<400> 3
atcgatctcc agacaccaag caagacctga gaaaaaacca tggctaaagc tacgggacga
60 tacaatctaa tatcgcccaa aaaggacctg gagaaggggt tgtcttaag cgacctctgt
120
```

```
aacttcttag ttagccaaac tattcagggg tggaaggttt attgggctgg tattgagttt    180
gatgtgactc acaaaggaat ggccctattg catagactga aaactaatga ctttgcccct    240
gcatggtcaa tgacaaggaa tctctttcct catttatttc aaaatccgaa ttccacaatt    300
gaatcaccgc tgtgggcatt gagagtcatc cttgcagcag ggatacagga ccagctgatt    360
gaccagtctt tgattgaacc cttagcagga gcccttggtc tgatctctga ttggctgcta    420
acaaccaaca ctaaccattt caacatgcga acacaacgtg tcaaggaaca attgagccta    480
aaaatgctgt cgttgattcg atccaatatt ctcaagttta ttaacaaatt ggatgctcta    540
catgtcgtga actacaacgg attgttgagc agtattgaaa ttggaactca aaatcataca    600
atcatcataa ctcgaactaa catgggtttt ctggtggagc tccaagaacc cgacaaatcg    660
gcaatgaacc gcatgaagcc tgggccggcg aaatttttccc tccttcatga gtccacactg    720
aaagcattta caaggatc ctcgacacga atgcaaagtt tgattcttga atttaatagc    780
tctcttgcta tctaactaag gtagaatact tcatattgag ctaactcata tatgctgact    840
catcgat                                                             847

<210> 4
<211> 973
<212> DNA
<213> Ebola zaire

<400> 4
atcgatcaga tctgcgaacc ggtagagttt agttgcaacc taacacacat aaagcattgg    60
tcaaaaagtc aatagaaatt taaacagtga gtggagacaa cttttaaatg gaagcttcat    120
atgagagagg acgcccacga gctgccagac agcattcaag ggatggacac gaccaccatg    180
ttcgagcacg atcatcatcc agagagaatt atcgaggtga gtaccgtcaa tcaaggagcg    240
cctcacaagt gcgcgttcct actgtatttc ataagaagag agttgaacca ttaacagttc    300
ctccagcacc taaagacata tgtccgacct tgaaaaaagg attttttgtgt gacagtagtt    360 tttgcaaaaa agatcaccag ttggagagtt taactgatag ggaattactc ctactaatcg    420
cccgtaagac ttgtggatca gtagaacaac aattaaatat aactgcaccc aaggactcgc    480
gcttagcaaa tccaacggct gatgatttcc agcaagagga aggtccaaaa attaccttgt    540
tgacactgat caagacggca gaacactggg cgagacaaga catcagaacc atagaggatt    600
caaaattaag agcattgttg actctatgtg ctgtgatgac gaggaaattc tcaaaatccc    660
agctgagtct tttatgtgag acacacctaa ggcgcgaggg gcttgggcaa gatcaggcag    
```

-continued

```
aacccgttct cgaagtatat caacgattac acagtgataa aggaggcagt tttgaagctg    720
cactatggca acaatgggac ctacaatccc taattatgtt tatcactgca ttcttgaata    780
ttgctctcca gttaccgtgt gaaagttctg ctgtcgttgt ttcagggtta agaacattgg    840
ttcctcaatc agataatgag gaagcttcaa ccaacccggg acatgctca tggtctgatg     900
agggtacatc gat                                                       960
                                                                     973
```

```
<210> 5
<211> 1148
<212> DNA
<213> Ebola zaire

<400> 5
```

```
atcgatagaa aagctggtct aacaagatga caactagaac aaagggcagg ggccatactg    60
cggccacgac tcaaaacgac agaatgccag gccctgagct ttcgggctgg atctctgagc   120
agctaatgac cggaagaatt cctgtaagcg acatcttctg tgatattgag aacaatccag   180
gattatgcta cgcatcccaa atgcaacaaa cgaagccaaa cccgaagacg cgcaacagtc   240
aaacccaaac ggacccaatt tgcaatcata gttttgagga ggtagtacaa acattggctt   300
cattggctac tgttgtgcaa caacaaacca tcgcatcaga atcattagaa caacgcatta   360
cgagtcttga aatggtcta aagccagttt atgatatggc aaaaacaatc tcctcattga   420
acaggggttg tgctgagatg gttgcaaaat atgatcttct ggtgatgaca accggtcggg   480
caacagcaac cgctgcggca actgaggctt attgggccga acatggtcaa ccaccacctg   540
gaccatcact ttatgaagaa agtgcgattc ggggtaagat tgaatctaga gatgagaccg   600
tccctcaaag tgttagggag gcattcaaca atctaaacag taccacttca ctaactgagg   660
aaaattttgg gaaacctgac atttcggcaa aggatttgag aaacattatg tatgatcact   720
tgcctggttt tggaactgct ttccaccaat tagtacaagt gatttgtaaa ttgggaaaag   780
atagcaactc attggacatc attcatgctg agttccaggc cagcctggct gaaggagact   840
ctcctcaatg tgccctaatt caaattacaa aaagagttcc aatcttccaa gatgctgctc   900
cacctgtcat ccacatccgc tctcgaggtg acattccccg agcttgccag aaaagcttgc   960
gtccagtccc accatcgccc aagattgatc gaggttgggt atgtgttttt cagcttcaag  1020
atggtaaaac acttggactc aaaatttgag ccaatctccc ttccctccga agaggcgaa   1080
taatagcaga ggcttcaact gctgaactat agggtacgtt acattaatga tacacttgtg  1140
```

```
agatcgat
1148

<210> 6
<211> 1123
<212> DNA
<213> Ebola zaire

<400> 6
atcgatccta cctcggctga gagagtgttt tttcattaac cttcatcttg taaacgttga      60
gcaaaattgt taaaaatatg aggcgggtta tattgcctac tgctcctcct gaatatatgg     120
aggccatata ccctgtcagg tcaaattcaa caattgctag aggtggcaac agcaatacag     180
gcttcctgac accggagtca gtcaatgggg acactccatc gaatccactc aggccaattg     240
ccgatgacac catcgaccat gccagccaca caccaggcag tgtgtcatca gcattcatcc     300
ttgaagctat ggtgaatgtc atatcgggcc ccaaagtgct aatgaagcaa attccaattt     360
ggcttcctct aggtgtcgct gatcaaaaga cctacagctt tgactcaact acggccgcca     420
tcatgcttgc ttcatacact atcacccatt tcggcaaggc aaccaatcca cttgtcagag     480
tcaatcggct gggtcctgga atcccggatc atccctcag gctcctgcga attggaaacc     540
aggctttcct ccaggagttc gttcttccgc cagtccaact accccagtat ttcacctttg     600
atttgacagc actcaaactg atcacccaac cactgcctgc tgcaacatgg accgatgaca     660
ctccaacagg atcaaatgga gcgttgcgtc caggaatttc atttcatcca aaacttcgcc     720
ccattctttt acccaacaaa gtgggaaga aggggaacag tgccgatcta acatctccgg     780
agaaaatcca agcaataatg acttcactcc aggactttaa gatcgttcca attgatccaa     840
ccaaaaatat catgggaatc gaagtgccag aaactctggt ccacaagctg accggtaaga     900
aggtgacttc taaaaatgga caaccaatca tccctgttct tttgccaaag tacattgggt     960
tggacccggt ggctccagga gacctcacca tggtaatcac acaggattgt gacacgtgtc    1020
attctcctgc aagtcttcca gctgtgattg agaagtaatt gcaataattg actcagatcc    1080
agttttatag aatcttctca gggatagtgc ataacatatc gat                       1123

<210> 7
<211> 1165
<212> DNA
<213> Ebola zaire

<400> 7
atcgatcaga tctgcgaacc ggtagagttt agttgcaacc taacacacat aaagcattgg      60
tcaaaaagtc aatagaaatt taaacagtga gtggagacaa cttttaaatg gaagcttcat     120
atgagagagg acgcccacga gctgccagac agcattcaag ggatggacac gaccaccatg    180
```

```
ttcgagcacg atcatcatcc agagagaatt atcgaggtga gtaccgtcaa tcaaggagcg    240
cctcacaagt gcgcgttcct actgtatttc ataagaagag agttgaacca ttaacagttc    300
ctccagcacc taaagacata tgtccgacct tgaaaaaagg atttttgtgt gacagtagtt    360
tttgcaaaaa agatcaccag ttggagagtt taactgatag ggaattactc ctactaatcg    420
cccgtaagac ttgtggatca gtagaacaac aattaaatat aactgcaccc aaggactcgc    480
gcttagcaaa tccaacggct gatgatttcc agcaagagga aggtccaaaa attaccttgt    540
tgacactgat caagacggca gaacactggg cgagacaaga catcagaacc atagaggatt    600
caaaattaag agcattgttg actctatgtg ctgtgatgac gaggaaattc tcaaaatccc    660
agctgagtct tttatgtgag acacacctaa ggcgcgaggg gcttgggcaa gatcaggcag    720
aacccgttct cgaagtatat caacgattac acagtgataa aggaggcagt tttgaagctg    780
cactatggca acaatgggac cgacaatccc taatcatgtt tatcactgca ttcttgaata    840
ttgctctcca gttaccgtgt gaaagttctg ctgtcgttgt ttcagggtta agaacattgg    900
ttcctcaatc agataatgag gaagcttcaa ccaacccggg gacatgctca tggtctgatg    960
agggtacccc ttaataaggc tgactaaaac actatataac cttctacttg atcacaatac   1020
tccgtatacc tatcatcata tatttaatca agacgatatc ctttaaaact tattcagtac   1080
tataatcact ctcgtttcaa attaataaga tgtgcatgat tgccctaata tatgaagagg   1140
tatgatacaa ccctaacaga tcgat                                         1165

<210> 8
<211> 30
<212> DNA
<213> Artificial Sequence

<220>
<223> Description of Artificial Sequence: Forward primer
      for VP24

<400> 8
gggatcgatc tccagacacc aagcaagacc                                      30

<210> 9
<211> 33
<212> DNA
<213> Artificial Sequence

<220>
<223> Description of Artificial Sequence: Reverse primer
      for VP24

<400> 9
gggatcgatg agtcagcata tatgagttag ctc                                  33

<210> 10

-continued

```
<212> DNA
<213> Artificial Sequence

<220>
<223> Description of Artificial Sequence: Forward primer
      for VP30

<400> 10
cccatcgatc agatctgcga accggtagag
30

<210> 11
<211> 31
<212> DNA
<213> Artificial Sequence

<220>
<223> Description of Artificial Sequence: Reverse primer
      for VP30

<400> 11
cccatcgatg taccctcatc agaccatgag c
31

<210> 12
<211> 33
<212> DNA
<213> Artificial Sequence

<220>
<223> Description of Artificial Sequence: Forward primer
      for VP35

<400> 12
gggatcgata gaaaagctgg tctaacaaga tga
33

<210> 13
<211> 36
<212> DNA
<213> Artificial Sequence

<220>
<223> Description of Artificial Sequence: Reverse primer
      for VP35

<400> 13
cccatcgatc tcacaagtgt atcattaatg taacgt
36

<210> 14
<211> 30
<212> DNA
<213> Artificial Sequence

<220>
<223> Description of Artificial Sequence: Forward primer
      for VP40

<400> 14
cccatcgatc ctacctcggc tgagagagtg
30

<210> 15
<211> 33
<212> DNA
<213> Artificial Sequence

<220>
<223> Description of Artificial Sequence: Reverse primer
      for VP40

<400> 15
cccatcgata tgttatgcac tatccctgag aag
33

<210> 16
<211> 30
<212> DNA
<213> Artificial Sequence
```

<220>
<223> Description of Artificial Sequence: Reverse primer
      for VP30#2

<400> 16
cccatcgatc tgttagggtt gtatcatacc          30

<210> 17
<211> 676
<212> PRT
<213> Ebola zaire

<400> 17

```
Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350
```

```
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
        370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
                420                 425                 430
Glu Asn Thr Asn Thr Ser Lys Ser Thr Asp Phe Leu Asp Pro Ala Thr
                435                 440                 445
Thr Thr Ser Pro Gln Asn His Ser Glu Thr Ala Gly Asn Asn Asn Thr
                450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
                500                 505                 510
Pro Asn Leu His Tyr Trp Thr Thr Gln Asp Glu Gly Ala Ala Ile Gly
                515                 520                 525
Leu Ala Trp Ile Pro Tyr Phe Gly Pro Ala Ala Glu Gly Ile Tyr Ile
        530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Phe Ser Ile Leu Asn Arg Lys Ala Ile Asp Phe
                580                 585                 590
Leu Leu Gln Arg Trp Gly Gly Thr Cys His Ile Leu Gly Pro Asp Cys
        595                 600                 605
Cys Ile Glu Pro His Asp Trp Thr Lys Asn Ile Thr Asp Lys Ile Asp
        610                 615                 620
Gln Ile Ile His Asp Phe Val Asp Lys Thr Leu Pro Asp Gln Gly Asp
625                 630                 635                 640
Asn Asp Asn Trp Trp Thr Gly Trp Arg Gln Trp Ile Pro Ala Gly Ile
                645                 650                 655
Gly Val Thr Gly Val Val Ile Ala Val Ile Ala Leu Phe Cys Ile Cys
                660                 665                 670
Lys Phe Val Phe
        675

<210> 18
<211> 739
<212> PRT
<213> Ebola zaire

<400> 18
Met Asp Ser Arg Pro Gln Lys Ile Trp Met Ala Pro Ser Leu Thr Glu
  1               5                  10                  15
Ser Asp Met Asp Tyr His Lys Ile Leu Thr Ala Gly Leu Ser Val Gln
                 20                  25                  30
Gln Gly Ile Val Arg Gln Arg Val Ile Pro Val Tyr Gln Val Asn Asn
         35                  40                  45
Leu Glu Glu Ile Cys Gln Leu Ile Ile Gln Ala Phe Glu Ala Gly Val
```

-continued

```
                50                  55                  60
Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                 85                  90                  95

Lys Tyr Leu Glu Gly His Gly Phe Arg Phe Glu Val Lys Lys Arg Asp
            100                 105                 110

Gly Val Lys Arg Leu Glu Leu Leu Pro Ala Val Ser Ser Gly Lys
            115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
            195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
            275                 280                 285

Lys His Gly Glu Tyr Ala Pro Phe Ala Arg Leu Leu Asn Leu Ser Gly
            290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
            355                 360                 365

Asp Asp Gln Glu Lys Lys Ile Leu Met Asn Phe His Gln Lys Lys Asn
            370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
                405                 410                 415

Thr Ser Gly His Tyr Asp Asp Asp Asp Ile Pro Phe Pro Gly Pro
            420                 425                 430

Ile Asn Asp Asp Asn Pro Gly His Gln Asp Asp Pro Thr Asp
            435                 440                 445

Ser Gln Asp Thr Thr Ile Pro Asp Val Val Asp Pro Asp Gly
            450                 455                 460

Ser Tyr Gly Glu Tyr Gln Ser Tyr Ser Glu Asn Gly Met Asn Ala Pro
465                 470                 475                 480
```

-continued

```
Asp Asp Leu Val Leu Phe Asp Leu Asp Glu Asp Thr Lys
            485             490             495

Pro Val Pro Asn Arg Ser Thr Lys Gly Gly Gln Gln Lys Asn Ser Gln
        500                 505                 510

Lys Gly Gln His Ile Glu Gly Arg Gln Thr Gln Ser Arg Pro Ile Gln
    515                 520                 525

Asn Val Pro Gly Pro His Arg Thr Ile His His Ala Ser Ala Pro Leu
530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Pro Leu Glu Ser Asp Asp Glu Glu Gln
            580                 585                 590

Asp Arg Asp Gly Thr Ser Asn Arg Thr Pro Thr Val Ala Pro Pro Ala
        595                 600                 605

Pro Val Tyr Arg Asp His Ser Glu Lys Lys Glu Leu Pro Gln Asp Glu
    610                 615                 620

Gln Gln Asp Gln Asp His Thr Gln Glu Ala Arg Asn Gln Asp Ser Asp
625                 630                 635                 640

Asn Thr Gln Ser Glu His Ser Phe Glu Glu Met Tyr Arg His Ile Leu
                645                 650                 655

Arg Ser Gln Gly Pro Phe Asp Ala Val Leu Tyr Tyr His Met Met Lys
            660                 665                 670

Asp Glu Pro Val Val Phe Ser Thr Ser Asp Gly Lys Glu Tyr Thr Tyr
        675                 680                 685

Pro Asp Ser Leu Glu Glu Glu Tyr Pro Pro Trp Leu Thr Lys Glu
    690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> 19
<211> 251
<212> PRT
<213> Ebola zaire

<400> 19
Met Ala Lys Ala Thr Gly Arg Tyr Asn Leu Ile Ser Pro Lys Lys Asp
  1               5                  10                  15

Leu Glu Lys Gly Val Val Leu Ser Asp Leu Cys Asn Phe Leu Val Ser
                20                  25                  30

Gln Thr Ile Gln Gly Trp Lys Val Tyr Trp Ala Gly Ile Glu Phe Asp
            35                  40                  45

Val Thr His Lys Gly Met Ala Leu Leu His Arg Leu Lys Thr Asn Asp
        50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125
```

-continued

```
Thr Asn Thr Asn His Phe Asn Met Arg Thr Gln Arg Val Lys Glu Gln
            130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Thr Arg
                180                 185                 190

Thr Asn Met Gly Phe Leu Val Glu Leu Gln Glu Pro Asp Lys Ser Ala
                195                 200                 205

Met Asn Arg Met Lys Pro Gly Pro Ala Lys Phe Ser Leu Leu His Glu
            210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250

<210> 20
<211> 324
<212> PRT
<213> Ebola zaire

<400> 20
Met Glu Ala Ser Tyr Glu Arg Gly Arg Pro Arg Ala Ala Arg Gln His
1               5                   10                  15

Ser Arg Asp Gly His Asp His Val Arg Ala Arg Ser Ser Ser Arg
            20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
    50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
                100                 105                 110

Glu Gln Gln Leu Asn Ile Thr Ala Pro Lys Asp Ser Arg Leu Ala Asn
            115                 120                 125

Pro Thr Ala Asp Asp Phe Gln Gln Glu Glu Gly Pro Lys Ile Thr Leu
130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
            195                 200                 205

Glu Val Tyr Gln Arg Leu His Ser Asp Lys Gly Gly Ser Phe Glu Ala
    210                 215                 220

Ala Leu Trp Gln Gln Trp Asp Leu Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270
```

```
Ala Ser Thr Asn Pro Gly Thr Cys Ser Trp Ser Asp Glu Gly Thr Ser
        275                 280                 285

Ile Gln Gln Gln Leu Ala Ser Cys Leu His Arg Thr Arg Gly Asp Trp
290                 295                 300

His Ala Ala Leu Lys Phe Leu Phe Tyr Phe Ser Phe Leu Phe Arg Ile
305                 310                 315                 320

Gly Phe Cys Phe

<210> 21
<211> 340
<212> PRT
<213> Ebola zaire

<400> 21
Met Thr Thr Arg Thr Lys Gly Arg Gly His Thr Ala Ala Thr Thr Gln
1               5                   10                  15

Asn Asp Arg Met Pro Gly Pro Glu Leu Ser Gly Trp Ile Ser Glu Gln
                20                  25                  30

Leu Met Thr Gly Arg Ile Pro Val Ser Asp Ile Phe Cys Asp Ile Glu
        35                  40                  45

Asn Asn Pro Gly Leu Cys Tyr Ala Ser Gln Met Gln Gln Thr Lys Pro
    50                  55                  60

Asn Pro Lys Thr Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

Ser Ser Leu Asn Arg Val Cys Ala Glu Met Val Ala Lys Tyr Asp Leu
    130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asn Ser Thr Thr Ser
        195                 200                 205

Leu Thr Glu Glu Asn Phe Gly Lys Pro Asp Ile Ser Ala Lys Asp Leu
    210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335
```

```
Gly Leu Lys Ile
            340

<210> 22
<211> 326
<212> PRT
<213> Ebola zaire

<400> 22
Met Arg Arg Val Ile Leu Pro Thr Ala Pro Pro Glu Tyr Met Glu Ala
  1               5                  10                  15

Ile Tyr Pro Val Arg Ser Asn Ser Thr Ile Ala Arg Gly Gly Asn Ser
                 20                  25                  30

Asn Thr Gly Phe Leu Thr Pro Glu Ser Val Asn Gly Asp Thr Pro Ser
             35                  40                  45

Asn Pro Leu Arg Pro Ile Ala Asp Asp Thr Ile Asp His Ala Ser His
 50                  55                  60

Thr Pro Gly Ser Val Ser Ser Ala Phe Ile Leu Glu Ala Met Val Asn
 65                  70                  75                  80

Val Ile Ser Gly Pro Lys Val Leu Met Lys Gln Ile Pro Ile Trp Leu
                 85                  90                  95

Pro Leu Gly Val Ala Asp Gln Lys Thr Tyr Ser Phe Asp Ser Thr Thr
                100                 105                 110

Ala Ala Ile Met Leu Ala Ser Tyr Thr Ile Thr His Phe Gly Lys Ala
            115                 120                 125

Thr Asn Pro Leu Val Arg Val Asn Arg Leu Gly Pro Gly Ile Pro Asp
        130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
            325

<210> 23
<211> 288
<212> PRT
<213> Ebola zaire

<400> 23
Met Glu Ala Ser Tyr Glu Arg Gly Arg Pro Arg Ala Ala Arg Gln His
```

-continued

```
              1               5                  10                  15
Ser Arg Asp Gly His Asp His Val Arg Ala Arg Ser Ser Ser Arg
                20                  25                  30

Glu Asn Tyr Arg Gly Glu Tyr Arg Gln Ser Arg Ser Ala Ser Gln Val
        35                  40                  45

Arg Val Pro Thr Val Phe His Lys Lys Arg Val Glu Pro Leu Thr Val
    50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
    130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> 24
<211> 11
<212> PRT
<213> Ebola zaire

<400> 24
Val Tyr Gln Val Asn Asn Leu Glu Glu Ile Cys
 1               5                  10

<210> 25
<211> 23
<212> PRT
<213> Ebola zaire

<400> 25
Leu Lys Phe Ile Asn Lys Leu Asp Ala Leu Leu Val Val Asn Tyr Asn
 1               5                  10                  15

Gly Leu Leu Ser Ser Ile Phe
            20

<210> 26
<211> 8
<212> PRT
<213> Ebola zaire

<400> 26
```

-continued

```
Gly Gln Phe Leu Phe Ala Ser Leu
  1               5

<210> 27
<211> 9
<212> PRT
<213> Ebola zaire

<400> 27
Asp Ala Val Leu Tyr Tyr His Met Met
  1               5

<210> 28
<211> 9
<212> PRT
<213> Ebola zaire

<400> 28
Ser Phe Lys Ala Ala Leu Ser Ser Leu
  1               5

<210> 29
<211> 15
<212> PRT
<213> Ebola zaire

<400> 29
Trp Ile Pro Tyr Phe Gly Pro Ala Ala Glu Gly Ile Tyr Thr Glu
  1               5                  10                  15

<210> 30
<211> 14
<212> PRT
<213> Ebola zaire

<400> 30
Asn Tyr Asn Gly Leu Leu Ser Ser Ile Glu Gly Thr Gln Asn
  1               5                  10

<210> 31
<211> 25
<212> PRT
<213> Ebola zaire

<400> 31
Arg Met Lys Pro Gly Pro Ala Lys Phe Ser Leu Leu His Glu Ser Thr
  1               5                  10                  15
Leu Lys Ala Phe Thr Gln Gly Ser Ser
              20                  25

<210> 32
<211> 15
<212> PRT
<213> Ebola zaire

<400> 32
Phe Ser Lys Ser Gln Leu Ser Leu Leu Cys Glu Thr His Leu Arg
  1               5                  10                  15

<210> 33
<211> 15
<212> PRT
<213> Ebola zaire

<400> 33
Asp Leu Gln Ser Leu Ile Met Phe Ile Thr Ala Phe Leu Asn Ile
  1               5                  10                  15

<210> 34
<211> 8
<212> PRT
<213> Ebola zaire

<400> 34
Arg Asn Ile Met Tyr Asp His Leu
  1               5

<210> 35
<211> 8
```

-continued

```
<212> PRT
<213> Ebola zaire

<400> 35
Met Val Ala Lys Tyr Asp Leu Leu
1               5

<210> 36
<211> 9
<212> PRT
<213> Ebola zaire

<400> 36
Cys Asp Ile Glu Asn Asn Pro Gly Leu
1               5

<210> 37
<211> 15
<212> PRT
<213> Ebola zaire

<400> 37
Ala Phe Leu Gln Glu Phe Val Leu Pro Pro Val Gln Leu Pro Gln
1               5                   10                  15

<210> 38
<211> 20
<212> PRT
<213> Ebola zaire

<400> 38
Phe Val Leu Pro Pro Val Gln Leu Pro Gln Tyr Phe Thr Phe Asp Leu
1               5                   10                  15

Thr Ala Leu Lys
            20

<210> 39
<211> 30
<212> PRT
<213> Ebola zaire

<400> 39
Lys Ser Gly Lys Lys Gly Asn Ser Ala Asp Leu Thr Ser Pro Glu Lys
1               5                   10                  15

Ile Gln Ala Ile Met Thr Ser Leu Gln Asp Phe Lys Ile Val
            20                  25                  30

<210> 40
<211> 15
<212> PRT
<213> Ebola zaire

<400> 40
Pro Leu Arg Leu Leu Arg Ile Gly Asn Gln Ala Phe Leu Gln Glu
1               5                   10                  15

<210> 41
<211> 15
<212> PRT
<213> Ebola zaire

<400> 41
Arg Ile Gly Asn Gln Ala Phe Leu Gln Glu Phe Val Leu Pro Pro
1               5                   10                  15

<210> 42
<211> 9
<212> PRT
<213> Ebola zaire

<400> 42
Tyr Phe Gly Pro Ala Ala Glu Gly Ile
1               5

<210> 43
<211> 9
<212> PRT
<213> Ebola zaire
```

```
<400> 43
Lys Phe Ile Asn Lys Leu Asp Ala Leu
 1               5

<210> 44
<211> 9
<212> PRT
<213> Ebola zaire

<400> 44
Asn Tyr Asn Gly Leu Leu Ser Ser Ile
 1               5

<210> 45
<211> 9
<212> PRT
<213> Ebola zaire

<400> 45
Pro Gly Pro Ala Lys Phe Ser Leu Leu
 1               5

<210> 46
<211> 10
<212> PRT
<213> Ebola zaire

<400> 46
Leu Ser Leu Leu Cys Glu Thr His Leu Arg
 1               5                  10

<210> 47
<211> 9
<212> PRT
<213> Ebola zaire

<400> 47
Met Phe Ile Thr Ala Phe Leu Asn Ile
 1               5

<210> 48
<211> 9
<212> PRT
<213> Ebola zaire

<400> 48
Glu Phe Val Leu Pro Pro Val Gln Leu
 1               5

<210> 49
<211> 6
<212> PRT
<213> Ebola zaire

<400> 49
Phe Leu Val Pro Pro Val
 1               5

<210> 50
<211> 11
<212> PRT
<213> Ebola zaire

<400> 50
Gln Tyr Phe Thr Phe Asp Leu Thr Ala Leu Lys
 1               5                  10

<210> 51
<211> 9
<212> PRT
<213> Ebola zaire

<400> 51
Thr Ser Pro Glu Lys Ile Gln Ala Ile
 1               5

<210> 52
<211> 8
<212> PRT
```

-continued

<213> Ebola zaire

<400> 52
Arg Ile Gly Asn Gln Ala Phe Leu
 1               5

<210> 53
<211> 8
<212> PRT
<213> Ebola zaire

<400> 53
Gln Ala Phe Leu Gln Glu Phe Val
 1               5

SEQUENCE LISTING

<160> NUMBER OF SEQ ID NOS: 461

<210> SEQ ID NO 1
<211> LENGTH: 2298
<212> TYPE: DNA
<213> ORGANISM: Zaire ebolavirus

<400> SEQUENCE: 1

```
atcgataagc tcggaattcg agctcgcccg gggatcctct agagtcgaca acaacacaat      60
gggcgttaca ggaatattgc agttacctcg tgatcgattc aagaggacat cattctttct     120
ttgggtaatt atccttttcc aaagaacatt ttccatccca cttggagtca tccacaatag     180
cacattacag gttagtgatg tcgacaaact agtttgtcgt gacaaactgt catccacaaa     240
tcaattgaga tcagttggac tgaatctcga agggaatgga gtggcaactg acgtgccatc     300
tgcaactaaa agatggggct tcaggtccgg tgtcccacca aggtggtca attatgaagc     360
tggtgaatgg gctgaaaaact gctacaatct tgaaatcaaa aaacctgacg ggagtgagtg     420
tctaccagca gcgccagacg ggattcgggg cttccccgg tgccggtatg tgcacaaagt     480
atcaggaacg gaccgtgtg ccggagactt gccttccat aaagagggtg ctttcttcct     540
gtatgatcga cttgcttcca cagttatcta ccgaggaacg actttcgctg aaggtgtcgt     600
tgcatttctg atactgcccc aagctaagaa ggacttcttc agctcacacc ccttgagaga     660
gccggtcaat gcaacggagg acccgtctag tggctactat tctaccacaa ttagatatca     720
ggctaccggt tttggaacca atgagacaga gtacttgttc gaggttgaca atttgaccta     780
cgtccaactt gaatcaagat tcacaccaca gtttctgctc cagctgaatg agacaatata     840
tacaagtggg aaaaggagca ataccacggg aaaactaatt tggaaggtca ccccgaaat     900
tgatacaaca atcggggagt gggccttctg ggaaactaaa aaaaaacctca ctagaaaaat     960
tcgcagtgaa gagttgtctt tcacagttgt atcaaacgga ccaaaaaca tcagtggtca    1020
gagtccggcg cgaacttctt ccgacccagg accaacacaa caactgaag accacaaaat    1080
catggcttca gaaaattcct ctgcaatggt tcaagtgcac agtcaaggaa gggaagctgc    1140
agtgtcgcat ctaacaaccc ttgccacaat ctccacgagt ccccaatccc tcacaaccaa    1200
accaggtccg acaacagca cccataatac acccgtgtat aaacttgaca tctctgaggc    1260
aactcaagtt gaacaagatc accgcagaac agacaacgac agcacagcct ccgacactcc    1320
ctctgccacg accgcagccg gacccccaaa agcagagaac caacacga gcaagagcac    1380
tgacttcctg gaccccgcca ccacaacaag tcccaaaac acagcgaga ccgctggcaa    1440
caacaacact catcaccaag ataccggaga agagagtgcc agcagcggga agctaggctt    1500
```

```
aattaccaat actattgctg gagtcgcagg actgatcaca ggcgggagaa gaactcgaag    1560
agaagcaatt gtcaatgctc aacccaaatg caaccctaat ttacattact ggactactca    1620
ggatgaaggt gctgcaatcg gactggcctg gataccatat ttcgggccag cagccgaggg    1680
aatttacata gagggggctaa tgcacaatca agatggttta atctgtgggt tgagacagct    1740
ggccaacgag acgactcaag ctcttcaact gttcctgaga gccacaactg agctacgcac    1800
cttttcaatc ctcaaccgta aggcaattga tttcttgctg cagcgatggg gcggcacatg    1860
ccacattctg ggaccggact gctgtatcga accacatgat tggaccaaga acataacaga    1920
caaaattgat cagattattc atgattttgt tgataaaacc cttccggacc aggggggacaa    1980 tgacaattgg tggacaggat ggagacaatg gataccggca ggtattggag ttacaggcgt    2040
tgtaattgca gttatcgctt tattctgtat atgcaaattt gtcttttagt ttttcttcag    2100
attgcttcat ggaaaagctc agcctcaaat caatgaaacc aggatttaat tatatggatt    2160
acttgaatct aagattactt gacaaatgat aatataatac actggagctt taaacatagc    2220
caatgtgatt ctaactcctt taaactcaca gttaatcata acaaggtttt gagtcgacct    2280
gcagccaagc ttatcgat                                                  2298

<210> SEQ ID NO 2
<211> LENGTH: 2428
<212> TYPE: DNA
<213> ORGANISM: Zaire ebolavirus

<400> SEQUENCE: 2
atcgataagc ttggctgcag gtcgactcta gaggatccga gtatggattc tcgtcctcag      60
aaaatctgga tggcgccgag tctcactgaa tctgacatgg attaccacaa gatcttgaca     120
gcaggtctgt ccgttcaaca ggggattgtt cggcaaagag tcatcccagt gtatcaagta     180
aacaatcttg aagaaatttg ccaacttatc atacaggcct ttgaagcagg tgttgatttt     240
caagagagtg cggacagttt ccttctgatg ctttgtcttc atcatgcgta ccagggagat     300
tacaaacttt tcttggaaag tggcgcagtc aagtatttgg aagggcacgg gttccgtttt     360
gaagtcaaga agcgtgatgg agtgaagcga cttgaggaat tgctgccagc agtatctagt     420
ggaaaaaaca ttaagagaac acttgctgcc atgccggaag aggagacaac tgaagctaat     480
gccggtcagt ttctctcctt tgcaagtcta ttccttccga aattggtagt aggagaaaag     540
gcttgccttg agaaggttca aaggcaaatt caagtacatg cagagcaagg actgatacaa     600
tatccaacag cttggcaatc agtaggacac atgatggtga ttttccgttt gatgcgaaca     660
aattttctga tcaaatttct cctaatacac aagggatgc acatggttgc cgggcatgat     720
gccaacgatg ctgtgatttc aaattcagtg gctcaagctc gttttttcagg cttattgatt     780 gtcaaaacag tacttgatca tatcctacaa aagacagaac gaggagttcg tctccatcct     840
cttgcaagga ccgccaaggt aaaaaatgag gtgaactcct ttaaggctgc actcagctcc     900
ctggccaagc atgagagta tgctcctttc gcccgacttt tgaacctttc tggagtaaat     960
aatcttgagc atggtctttt ccctcaacta tcggcaattg cactcggagt cgccacagca    1020
cacgggagta ccctcgcagg agtaaatgtt ggagaacagt atcaacaact cagagaggct    1080
gccactgagg ctgagaagca actccaacaa tatgcagagt ctcgcgaact tgaccatctt    1140
ggacttgatg atcaggaaaa gaaaattctt atgaacttcc atcagaaaaa gaacgaaatc    1200
agcttccagc aaacaaacgc tatggtaact ctaagaaaag agcgcctggc caagctgaca    1260
```

```
gaagctatca ctgctgcgtc actgcccaaa acaagtggac attacgatga tgatgacgac   1320
attccctttc caggacccat caatgatgac gacaatccta gccatcaaga tgatgatccg   1380
actgactcac aggatacgac cattcccgat gtggtggttg atcccgatga tggaagctac   1440
ggcgaatacc agagttactc ggaaaacggc atgaatgcac cagatgactt ggtcctattc   1500
gatctagacg aggacgacga ggacactaag ccagtgccta atagatcgac caagggtgga   1560
caacagaaga acagtcaaaa gggccagcat atagagggca gacagacaca atccaggcca   1620
attcaaaatg tcccaggccc tcacagaaca atccaccacg ccagtgcgcc actcacggac   1680
aatgacagaa gaaatgaacc ctccggctca accagccctc gcatgctgac accaattaac   1740
gaagaggcag acccactgga cgatgccgac gacgagacgt ctagccttcc gcccttggag   1800
tcagatgatg aagagcagga cagggacgga acttccaacc gcacacccac tgtcgcccca   1860
ccggctcccg tatacagaga tcactctgaa aagaaagaac tcccgcaaga cgagcaacaa   1920
gatcaggacc acactcaaga ggccaggaac caggacagta caacaccca gtcagaacac   1980 tcttttgagg agatgtatcg ccacattcta agatcacagg ggccatttga tgctgttttg   2040
tattatcata tgatgaagga tgagcctgta gtttttcagta ccagtgatgg caaagagtac   2100
acgtatccag actcccttga agaggaatat ccaccatggc tcactgaaaa agaggctatg   2160
aatgaagaga atagatttgt tacattggat ggtcaacaat tttattggcc ggtgatgaat   2220
cacaagaata aattcatggc aatcctgcaa catcatcagt gaatgagcat ggaacaatgg   2280
gatgattcaa ccgacaaata gctaacatta gtagtccag aacgaaaac aggaagaatt   2340 tttgatgtct aaggtgtgaa ttattatcac aataaaagtg attcttattt ttgaatttgg   2400
gcgagctcga attcccgagc ttatcgat                                      2428

<210> SEQ ID NO 3
<211> LENGTH: 847
<212> TYPE: DNA
<213> ORGANISM: Zaire ebolavirus

<400> SEQUENCE: 3
atcgatctcc agacaccaag caagacctga gaaaaaacca tggctaaagc tacgggacga   60
tacaatctaa tatcgcccaa aaaggacctg gagaaagggg ttgtcttaag cgacctctgt   120
aacttcttag ttagccaaac tattcagggg tggaaggttt attgggctgg tattgagttt   180
gatgtgactc acaaaggaat ggccctattg catagactga aaactaatga ctttgccccct   240 gcatggtcaa tgacaaggaa tctctttcct catttatttc aaaatccgaa ttccacaatt   300
gaatcaccgc tgtgggcatt gagagtcatc cttgcagcag ggatacagga ccagctgatt   360
gaccagtctt tgattgaacc cttagcagga gcccttggtc tgatctctga ttggctgcta   420
acaaccaaca ctaaccattt caacatgcga acacaacgtg tcaaggaaca attgagccta   480
aaaatgctgt cgttgattcg atccaatatt ctcaagttta ttaacaaatt ggatgctcta   540
catgtcgtga actacaacgg attgttgagc agtattgaaa ttggaactca aaatcataca   600
atcatcataa ctcgaactaa catgggtttt ctggtggagc tccaagaacc cgacaaatcg   660
gcaatgaacc gcatgaagcc tgggccggcg aaattttccc tccttcatga gtccacactg   720
aaagcattta cacaaggatc ctcgacacga atgcaaagtt tgattcttga atttaatagc   780
tctcttgcta tctaactaag gtagaatact tcatattgag ctaactcata tatgctgact   840
catcgat                                                              847
```

<210> SEQ ID NO 4
<211> LENGTH: 973
<212> TYPE: DNA
<213> ORGANISM: Zaire ebolavirus

<400> SEQUENCE: 4

| | | | | | | |
|---|---|---|---|---|---|---|
| atcgatcaga | tctgcgaacc | ggtagagttt | agttgcaacc | taacacacat | aaagcattgg | 60 |
| tcaaaaagtc | aatagaaatt | taaacagtga | gtggagacaa | cttttaaatg | gaagcttcat | 120 |
| atgagagagg | acgcccacga | gctgccagac | agcattcaag | ggatggacac | gaccaccatg | 180 |
| ttcgagcacg | atcatcatcc | agagagaatt | atcgaggtga | gtaccgtcaa | tcaaggagcg | 240 |
| cctcacaagt | gcgcgttcct | actgtatttc | ataagaagag | agttgaacca | ttaacagttc | 300 |
| ctccagcacc | taaagacata | tgtccgacct | tgaaaaaagg | atttttgtgt | gacagtagtt | 360 |
| tttgcaaaaa | agatcaccag | ttggagagtt | taactgatag | ggaattactc | ctactaatcg | 420 |
| cccgtaagac | ttgtggatca | gtagaacaac | aattaaatat | aactgcaccc | aaggactcgc | 480 |
| gcttagcaaa | tccaacggct | gatgatttcc | agcaagagga | aggtccaaaa | attaccttgt | 540 |
| tgacactgat | caagacggca | gaacactggg | cgagacaaga | catcagaacc | atagaggatt | 600 |
| caaaattaag | agcattgttg | actctatgtg | ctgtgatgac | gaggaaattc | tcaaaatccc | 660 |
| agctgagtct | tttatgtgag | acacacctaa | ggcgcgaggg | gcttgggcaa | gatcaggcag | 720 |
| aacccgttct | cgaagtatat | caacgattac | acagtgataa | aggaggcagt | tttgaagctg | 780 |
| cactatggca | acaatgggac | ctacaatccc | taattatgtt | tatcactgca | ttcttgaata | 840 |
| ttgctctcca | gttaccgtgt | gaaagttctg | ctgtcgttgt | ttcagggtta | agaacattgg | 900 |
| ttcctcaatc | agataatgag | gaagcttcaa | ccaacccggg | gacatgctca | tggtctgatg | 960 |
| agggtacatc | gat | | | | | 973 |

<210> SEQ ID NO 5
<211> LENGTH: 1148
<212> TYPE: DNA
<213> ORGANISM: Zaire ebolavirus

<400> SEQUENCE: 5

| | | | | | | |
|---|---|---|---|---|---|---|
| atcgatagaa | aagctggtct | aacaagatga | caactagaac | aaagggcagg | ggccatactg | 60 |
| cggccacgac | tcaaaacgac | agaatgccag | gccctgagct | tcgggctgg | atctctgagc | 120 |
| agctaatgac | cggaagaatt | cctgtaagcg | acatcttctg | tgatattgag | aacaatccag | 180 |
| gattatgcta | cgcatcccaa | atgcaacaaa | cgaagccaaa | cccgaagacg | cgcaacagtc | 240 |
| aaacccaaac | ggacccaatt | tgcaatcata | gttttgagga | ggtagtacaa | acattggctt | 300 |
| cattggctac | tgttgtgcaa | caacaaacca | tcgcatcaga | atcattagaa | caacgcatta | 360 |
| cgagtcttga | gaatggtcta | aagccagttt | atgatatggc | aaaaacaatc | tcctcattga | 420 |
| acagggtttg | tgctgagatg | gttgcaaaat | atgatcttct | ggtgatgaca | accggtcggg | 480 |
| caacagcaac | cgctgcggca | actgaggctt | attgggccga | acatggtcaa | ccaccacctg | 540 |
| gaccatcact | ttatgaagaa | agtgcgattc | ggggtaagat | tgaatctaga | gatgagaccg | 600 |
| tccctcaaag | tgttagggag | gcattcaaca | atctaaacag | taccacttca | ctaactgagg | 660 |
| aaaattttgg | gaaacctgac | atttcggcaa | aggatttgag | aaacattatg | tatgatcact | 720 |
| tgcctggttt | tggaactgct | ttccaccaat | tagtacaagt | gatttgtaaa | ttgggaaaag | 780 |
| atagcaactc | attggacatc | attcatgctg | agttccaggc | cagcctggct | gaaggagact | 840 |
| ctcctcaatg | tgccctaatt | caaattacaa | aaagagttcc | aatcttccaa | gatgctgctc | 900 |

| | | |
|---|---|---|
| cacctgtcat ccacatccgc tctcgaggtg acattccccg agcttgccag aaaagcttgc | 960 | |
| gtccagtccc accatcgccc aagattgatc gaggttgggt atgtgttttt cagcttcaag | 1020 | |
| atggtaaaac acttggactc aaaatttgag ccaatctccc ttccctccga aagaggcgaa | 1080 | |
| taatagcaga ggcttcaact gctgaactat agggtacgtt acattaatga tacacttgtg | 1140 | |
| agatcgat | 1148 | |

<210> SEQ ID NO 6
<211> LENGTH: 1123
<212> TYPE: DNA
<213> ORGANISM: Zaire ebolavirus

<400> SEQUENCE: 6

| | | |
|---|---|---|
| atcgatccta cctcggctga gagagtgttt tttcattaac cttcatcttg taaacgttga | 60 | |
| gcaaaattgt taaaaatatg aggcgggtta tattgcctac tgctcctcct gaatatatgg | 120 | |
| aggccatata ccctgtcagg tcaaattcaa caattgctag aggtggcaac agcaatacag | 180 | |
| gcttcctgac accggagtca gtcaatgggg acactccatc gaatccactc aggccaattg | 240 | |
| ccgatgacac catcgaccat gccagccaca caccaggcag tgtgtcatca gcattcatcc | 300 | |
| ttgaagctat ggtgaatgtc atatcgggcc ccaaagtgct aatgaagcaa attccaattt | 360 | |
| ggcttcctct aggtgtcgct gatcaaaaga cctacagctt tgactcaact acggccgcca | 420 | |
| tcatgcttgc ttcatacact atcacccatt tcggcaaggc aaccaatcca cttgtcagag | 480 | |
| tcaatcggct gggtcctgga atcccggatc atcccctcag gctcctgcga attggaaacc | 540 | |
| aggctttcct ccaggagttc gttcttccgc cagtccaact accccagtat ttcacctttg | 600 | |
| atttgacagc actcaaactg atcacccaac cactgcctgc tgcaacatgg accgatgaca | 660 | |
| ctccaacagg atcaaatgga gcgttgcgtc caggaatttc atttcatcca aaacttcgcc | 720 | |
| ccattctttt acccaacaaa agtgggaaga aggggaacag tgccgatcta acatctccgg | 780 | |
| agaaaatcca agcaataatg acttcactcc aggactttaa gatcgttcca attgatccaa | 840 | |
| ccaaaaatat catgggaatc gaagtgccag aaactctggt ccacaagctg accggtaaga | 900 | |
| aggtgacttc taaaaatgga caaccaatca tccctgttct tttgccaaag tacattgggt | 960 | |
| tggacccggt ggctccagga gacctcacca tggtaatcac acaggattgt gacacgtgtc | 1020 | |
| attctcctgc aagtcttcca gctgtgattg agaagtaatt gcaataattg actcagatcc | 1080 | |
| agttttatag aatcttctca gggatagtgc ataacatatc gat | 1123 | |

<210> SEQ ID NO 7
<211> LENGTH: 1165
<212> TYPE: DNA
<213> ORGANISM: Zaire ebolavirus

<400> SEQUENCE: 7

| | | |
|---|---|---|
| atcgatcaga tctgcgaacc ggtagagttt agttgcaacc taacacacat aaagcattgg | 60 | |
| tcaaaaagtc aatagaaatt taaacagtga gtggagacaa cttttaaatg gaagcttcat | 120 | |
| atgagagagg acgcccacga gctgccagac agcattcaag gatggacac gaccaccatg | 180 | |
| ttcgagcacg atcatcatcc agagagaatt atcgaggtga gtaccgtcaa tcaaggagcg | 240 | |
| cctcacaagt gcgcgttcct actgtatttc ataagaagag agttgaacca ttaacagttc | 300 | |
| ctccagcacc taaagacata tgtccgacct tgaaaaaagg atttttgtgt gacagtagtt | 360 | |
| tttgcaaaaa agatcaccag ttggagagtt taactgatag ggaattactc ctactaatcg | 420 | |
| cccgtaagac ttgtggatca gtagaacaac aattaaatat aactgcaccc aaggactcgc | 480 | |

-continued

```
gcttagcaaa tccaacggct gatgatttcc agcaagagga aggtccaaaa attaccttgt    540
tgacactgat caagacggca gaacactggg cgagacaaga catcagaacc atagaggatt    600
caaaattaag agcattgttg actctatgtg ctgtgatgac gaggaaattc tcaaaatccc    660
agctgagtct tttatgtgag acacacctaa ggcgcgaggg gcttgggcaa gatcaggcag    720
aacccgttct cgaagtatat caacgattac acagtgataa aggaggcagt tttgaagctg    780
cactatggca acaatgggac cgacaatccc taatcatgtt tatcactgca ttcttgaata    840
ttgctctcca gttaccgtgt gaaagttctg ctgtcgttgt ttcagggtta agaacattgg    900
ttcctcaatc agataatgag gaagcttcaa ccaacccggg gacatgctca tggtctgatg    960
agggtacccc ttaataaggc tgactaaaac actatataac cttctacttg atcacaaatac   1020 tccgtatacc tatcatcata tatttaatca agacgatatc ctttaaaact tattcagtac   1080
tataatcact ctcgtttcaa attaataaga tgtgcatgat tgccctaata tatgaagagg   1140
tatgatacaa ccctaacaga tcgat                                         1165
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggatcgatc tccagacacc aagcaagacc                                    30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggatcgatg agtcagcata tatgagttag ctc                                33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccatcgatc agatctgcga accggtagag                                    30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccatcgatg taccctcatc agaccatgag c                                  31

<210> SEQ ID NO 12

```
<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggatcgata gaaaagctgg tctaacaaga tga                                33

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccatcgatc tcacaagtgt atcattaatg taacgt                             36

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccatcgatc ctacctcggc tgagagagtg                                    30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccatcgata tgttatgcac tatccctgag aag                                33

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccatcgatc tgttagggtt gtatcatacc                                    30

<210> SEQ ID NO 17
<211> LENGTH: 676
<212> TYPE: PRT
<213> ORGANISM: Zaire ebolavirus

<400> SEQUENCE: 17

Met Gly Val Thr Gly Ile Leu Gln Leu Pro Arg Asp Arg Phe Lys Arg
  1               5                  10                  15

Thr Ser Phe Phe Leu Trp Val Ile Ile Leu Phe Gln Arg Thr Phe Ser
             20                  25                  30

Ile Pro Leu Gly Val Ile His Asn Ser Thr Leu Gln Val Ser Asp Val
         35                  40                  45
```

```
Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
             100                 105                 110

Ile Lys Lys Pro Asp Gly Ser Glu Cys Leu Pro Ala Ala Pro Asp Gly
         115                 120                 125

Ile Arg Gly Phe Pro Arg Cys Arg Tyr Val His Lys Val Ser Gly Thr
     130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                 165                 170                 175

Ala Glu Gly Val Val Ala Phe Leu Ile Leu Pro Gln Ala Lys Lys Asp
             180                 185                 190

Phe Phe Ser Ser His Pro Leu Arg Glu Pro Val Asn Ala Thr Glu Asp
         195                 200                 205

Pro Ser Ser Gly Tyr Tyr Ser Thr Thr Ile Arg Tyr Gln Ala Thr Gly
     210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                 245                 250                 255

Asn Glu Thr Ile Tyr Thr Ser Gly Lys Arg Ser Asn Thr Thr Gly Lys
             260                 265                 270

Leu Ile Trp Lys Val Asn Pro Glu Ile Asp Thr Thr Ile Gly Glu Trp
         275                 280                 285

Ala Phe Trp Glu Thr Lys Lys Asn Leu Thr Arg Lys Ile Arg Ser Glu
     290                 295                 300

Glu Leu Ser Phe Thr Val Val Ser Asn Gly Ala Lys Asn Ile Ser Gly
305                 310                 315                 320

Gln Ser Pro Ala Arg Thr Ser Asp Pro Gly Thr Asn Thr Thr Thr
                 325                 330                 335

Glu Asp His Lys Ile Met Ala Ser Glu Asn Ser Ser Ala Met Val Gln
             340                 345                 350

Val His Ser Gln Gly Arg Glu Ala Ala Val Ser His Leu Thr Thr Leu
         355                 360                 365

Ala Thr Ile Ser Thr Ser Pro Gln Ser Leu Thr Thr Lys Pro Gly Pro
     370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                 405                 410                 415

Ala Ser Asp Thr Pro Ser Ala Thr Thr Ala Ala Gly Pro Pro Lys Ala
             420                 425                 430

Glu Asn Thr Asn Thr Ser Lys Ser Thr Asp Phe Leu Asp Pro Ala Thr
         435                 440                 445

Thr Thr Ser Pro Gln Asn His Ser Glu Thr Ala Gly Asn Asn Asn
     450                 455                 460
```

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
        530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Val Ile Ala Val Ile Ala Leu Phe Cys Ile Cys
            660                 665                 670

Lys Phe Val Phe
        675

<210> SEQ ID NO 18
<211> LENGTH: 739
<212> TYPE: PRT
<213> ORGANISM: Zaire ebolavirus

<400> SEQUENCE: 18

Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Leu Pro Ala Val Ser Ser Gly Lys
        115                 120                 125

Asn Ile Lys Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

-continued

```
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ala Trp Gln
            180                 185                 190
Ser Val Gly His Met Met Val Ile Phe Arg Leu Met Arg Thr Asn Phe
        195                 200                 205
Leu Ile Lys Phe Leu Leu Ile His Gln Gly Met His Met Val Ala Gly
    210                 215                 220
His Asp Ala Asn Asp Ala Val Ile Ser Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Glu Arg Gly Val Arg Leu His Pro Leu Ala Arg Thr Ala Lys
            260                 265                 270
Val Lys Asn Glu Val Asn Ser Phe Lys Ala Ala Leu Ser Ser Leu Ala
        275                 280                 285
Lys His Gly Glu Tyr Ala Pro Phe Ala Arg Leu Leu Asn Leu Ser Gly
    290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
            340                 345                 350
Gln Leu Gln Gln Tyr Ala Glu Ser Arg Glu Leu Asp His Leu Gly Leu
        355                 360                 365
Asp Asp Gln Glu Lys Lys Ile Leu Met Asn Phe His Gln Lys Lys Asn
    370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
                405                 410                 415
Thr Ser Gly His Tyr Asp Asp Asp Asp Ile Pro Phe Pro Gly Pro
            420                 425                 430
Ile Asn Asp Asp Asp Asn Pro Gly His Gln Asp Asp Pro Thr Asp
        435                 440                 445
Ser Gln Asp Thr Thr Ile Pro Asp Val Val Asp Pro Asp Asp Gly
    450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Glu Asp Thr Lys
                485                 490                 495
Pro Val Pro Asn Arg Ser Thr Lys Gly Gly Gln Gln Lys Asn Ser Gln
            500                 505                 510
Lys Gly Gln His Ile Glu Gly Arg Gln Thr Gln Ser Arg Pro Ile Gln
        515                 520                 525
Asn Val Pro Gly Pro His Arg Thr Ile His His Ala Ser Ala Pro Leu
    530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
                565                 570                 575
```

```
Asp Glu Thr Ser Ser Leu Pro Pro Leu Glu Ser Asp Asp Glu Glu Gln
                580                 585                 590

Asp Arg Asp Gly Thr Ser Asn Arg Thr Pro Thr Val Ala Pro Pro Ala
            595                 600                 605

Pro Val Tyr Arg Asp His Ser Glu Lys Lys Glu Leu Pro Gln Asp Glu
        610                 615                 620

Gln Gln Asp Gln Asp His Thr Gln Glu Ala Arg Asn Gln Asp Ser Asp
625                 630                 635                 640

Asn Thr Gln Ser Glu His Ser Phe Glu Glu Met Tyr Arg His Ile Leu
                645                 650                 655

Arg Ser Gln Gly Pro Phe Asp Ala Val Leu Tyr Tyr His Met Met Lys
            660                 665                 670

Asp Glu Pro Val Val Phe Ser Thr Ser Asp Gly Lys Glu Tyr Thr Tyr
        675                 680                 685

Pro Asp Ser Leu Glu Glu Glu Tyr Pro Pro Trp Leu Thr Glu Lys Glu
        690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> SEQ ID NO 19
<211> LENGTH: 251
<212> TYPE: PRT
<213> ORGANISM: Zaire ebolavirus

<400> SEQUENCE: 19

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
                20                  25                  30

Gln Thr Ile Gln Gly Trp Lys Val Tyr Trp Ala Gly Ile Glu Phe Asp
            35                  40                  45

Val Thr His Lys Gly Met Ala Leu Leu His Arg Leu Lys Thr Asn Asp
        50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
    130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Ile Thr Arg
            180                 185                 190

Thr Asn Met Gly Phe Leu Val Glu Leu Gln Glu Pro Asp Lys Ser Ala
        195                 200                 205
```

```
Met Asn Arg Met Lys Pro Gly Pro Ala Lys Phe Ser Leu Leu His Glu
            210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250

<210> SEQ ID NO 20
<211> LENGTH: 324
<212> TYPE: PRT
<213> ORGANISM: Zaire ebolavirus

<400> SEQUENCE: 20

Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Ser Arg
                20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
        50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Leu Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Ser
        275                 280                 285

Ile Gln Gln Gln Leu Ala Ser Cys Leu His Arg Thr Arg Gly Asp Trp
    290                 295                 300

His Ala Ala Leu Lys Phe Leu Phe Tyr Phe Ser Phe Leu Phe Arg Ile
305                 310                 315                 320

Gly Phe Cys Phe
```

<210> SEQ ID NO 21
<211> LENGTH: 340
<212> TYPE: PRT
<213> ORGANISM: Zaire ebolavirus

<400> SEQUENCE: 21

Met Thr Thr Arg Thr Lys Gly Arg Gly His Thr Ala Ala Thr Thr Gln
1               5                   10                  15

Asn Asp Arg Met Pro Gly Pro Glu Leu Ser Gly Trp Ile Ser Glu Gln
            20                  25                  30

Leu Met Thr Gly Arg Ile Pro Val Ser Asp Ile Phe Cys Asp Ile Glu
        35                  40                  45

Asn Asn Pro Gly Leu Cys Tyr Ala Ser Gln Met Gln Gln Thr Lys Pro
    50                  55                  60

Asn Pro Lys Thr Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

Ser Ser Leu Asn Arg Val Cys Ala Glu Met Val Ala Lys Tyr Asp Leu
    130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asn Ser Thr Thr Ser
        195                 200                 205

Leu Thr Glu Glu Asn Phe Gly Lys Pro Asp Ile Ser Ala Lys Asp Leu
    210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 22
<211> LENGTH: 326
<212> TYPE: PRT
<213> ORGANISM: Zaire ebolavirus

<400> SEQUENCE: 22

```
Met Arg Arg Val Ile Leu Pro Thr Ala Pro Glu Tyr Met Glu Ala
1               5                   10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
                325
```

<210> SEQ ID NO 23
<211> LENGTH: 288
<212> TYPE: PRT
<213> ORGANISM: Zaire ebolavirus

<400> SEQUENCE: 23

```
Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Arg
            20                  25                  30
```

```
Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
 50                  55                  60

Pro Pro Ala Pro Lys Asp Ile Cys Pro Thr Leu Lys Lys Gly Phe Leu
 65                  70                  75                  80

Cys Asp Ser Ser Phe Cys Lys Lys Asp His Gln Leu Glu Ser Leu Thr
                 85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
            115                 120                 125

Pro Thr Ala Asp Asp Phe Gln Gln Glu Glu Gly Pro Lys Ile Thr Leu
            130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
                180                 185                 190

His Leu Arg Arg Glu Gly Leu Gly Gln Asp Gln Ala Glu Pro Val Leu
            195                 200                 205

Glu Val Tyr Gln Arg Leu His Ser Asp Lys Gly Gly Ser Phe Glu Ala
            210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
            275                 280                 285

<210> SEQ ID NO 24
<211> LENGTH: 11
<212> TYPE: PRT
<213> ORGANISM: Zaire ebolavirus

<400> SEQUENCE: 24

Val Tyr Gln Val Asn Asn Leu Glu Glu Ile Cys
1               5                   10

<210> SEQ ID NO 25
<211> LENGTH: 23
<212> TYPE: PRT
<213> ORGANISM: Zaire ebolavirus

<400> SEQUENCE: 25

Leu Lys Phe Ile Asn Lys Leu Asp Ala Leu Leu Val Val Asn Tyr Asn
1               5                   10                  15

Gly Leu Leu Ser Ser Ile Phe
            20

<210> SEQ ID NO 26
<211> LENGTH: 8
<212> TYPE: PRT
<213> ORGANISM: Zaire ebolavirus
```

```
<400> SEQUENCE: 26

Gly Gln Phe Leu Phe Ala Ser Leu
1               5

<210> SEQ ID NO 27
<211> LENGTH: 9
<212> TYPE: PRT
<213> ORGANISM: Zaire ebolavirus

<400> SEQUENCE: 27

Asp Ala Val Leu Tyr Tyr His Met Met
1               5

<210> SEQ ID NO 28
<211> LENGTH: 9
<212> TYPE: PRT
<213> ORGANISM: Zaire ebolavirus

<400> SEQUENCE: 28

Ser Phe Lys Ala Ala Leu Ser Ser Leu
1               5

<210> SEQ ID NO 29
<211> LENGTH: 15
<212> TYPE: PRT
<213> ORGANISM: Zaire ebolavirus

<400> SEQUENCE: 29

Trp Ile Pro Tyr Phe Gly Pro Ala Ala Glu Gly Ile Tyr Thr Glu
1               5                   10                  15

<210> SEQ ID NO 30
<211> LENGTH: 14
<212> TYPE: PRT
<213> ORGANISM: Zaire ebolavirus

<400> SEQUENCE: 30

Asn Tyr Asn Gly Leu Leu Ser Ser Ile Glu Gly Thr Gln Asn
1               5                   10

<210> SEQ ID NO 31
<211> LENGTH: 25
<212> TYPE: PRT
<213> ORGANISM: Zaire ebolavirus

<400> SEQUENCE: 31

Arg Met Lys Pro Gly Pro Ala Lys Phe Ser Leu Leu His Glu Ser Thr
1               5                   10                  15

Leu Lys Ala Phe Thr Gln Gly Ser Ser
            20                  25

<210> SEQ ID NO 32
<211> LENGTH: 15
<212> TYPE: PRT
<213> ORGANISM: Zaire ebolavirus

<400> SEQUENCE: 32

Phe Ser Lys Ser Gln Leu Ser Leu Leu Cys Glu Thr His Leu Arg
1               5                   10                  15

<210> SEQ ID NO 33
<211> LENGTH: 15
<212> TYPE: PRT
```

```
<213> ORGANISM: Zaire ebolavirus

<400> SEQUENCE: 33

Asp Leu Gln Ser Leu Ile Met Phe Ile Thr Ala Phe Leu Asn Ile
1               5                   10                  15

<210> SEQ ID NO 34
<211> LENGTH: 8
<212> TYPE: PRT
<213> ORGANISM: Zaire ebolavirus

<400> SEQUENCE: 34

Arg Asn Ile Met Tyr Asp His Leu
1               5

<210> SEQ ID NO 35
<211> LENGTH: 8
<212> TYPE: PRT
<213> ORGANISM: Zaire ebolavirus

<400> SEQUENCE: 35

Met Val Ala Lys Tyr Asp Leu Leu
1               5

<210> SEQ ID NO 36
<211> LENGTH: 9
<212> TYPE: PRT
<213> ORGANISM: Zaire ebolavirus

<400> SEQUENCE: 36

Cys Asp Ile Glu Asn Asn Pro Gly Leu
1               5

<210> SEQ ID NO 37
<211> LENGTH: 15
<212> TYPE: PRT
<213> ORGANISM: Zaire ebolavirus

<400> SEQUENCE: 37

Ala Phe Leu Gln Glu Phe Val Leu Pro Pro Val Gln Leu Pro Gln
1               5                   10                  15

<210> SEQ ID NO 38
<211> LENGTH: 20
<212> TYPE: PRT
<213> ORGANISM: Zaire ebolavirus

<400> SEQUENCE: 38

Phe Val Leu Pro Pro Val Gln Leu Pro Gln Tyr Phe Thr Phe Asp Leu
1               5                   10                  15

Thr Ala Leu Lys
            20

<210> SEQ ID NO 39
<211> LENGTH: 30
<212> TYPE: PRT
<213> ORGANISM: Zaire ebolavirus

<400> SEQUENCE: 39

Lys Ser Gly Lys Lys Gly Asn Ser Ala Asp Leu Thr Ser Pro Glu Lys
1               5                   10                  15

Ile Gln Ala Ile Met Thr Ser Leu Gln Asp Phe Lys Ile Val
            20                  25                  30
```

```
<210> SEQ ID NO 40
<211> LENGTH: 15
<212> TYPE: PRT
<213> ORGANISM: Zaire ebolavirus

<400> SEQUENCE: 40

Pro Leu Arg Leu Leu Arg Ile Gly Asn Gln Ala Phe Leu Gln Glu
1               5                   10                  15

<210> SEQ ID NO 41
<211> LENGTH: 15
<212> TYPE: PRT
<213> ORGANISM: Zaire ebolavirus

<400> SEQUENCE: 41

Arg Ile Gly Asn Gln Ala Phe Leu Gln Glu Phe Val Leu Pro Pro
1               5                   10                  15

<210> SEQ ID NO 42
<211> LENGTH: 9
<212> TYPE: PRT
<213> ORGANISM: Zaire ebolavirus

<400> SEQUENCE: 42

Tyr Phe Gly Pro Ala Ala Glu Gly Ile
1               5

<210> SEQ ID NO 43
<211> LENGTH: 9
<212> TYPE: PRT
<213> ORGANISM: Zaire ebolavirus

<400> SEQUENCE: 43

Lys Phe Ile Asn Lys Leu Asp Ala Leu
1               5

<210> SEQ ID NO 44
<211> LENGTH: 9
<212> TYPE: PRT
<213> ORGANISM: Zaire ebolavirus

<400> SEQUENCE: 44

Asn Tyr Asn Gly Leu Leu Ser Ser Ile
1               5

<210> SEQ ID NO 45
<211> LENGTH: 9
<212> TYPE: PRT
<213> ORGANISM: Zaire ebolavirus

<400> SEQUENCE: 45

Pro Gly Pro Ala Lys Phe Ser Leu Leu
1               5

<210> SEQ ID NO 46
<211> LENGTH: 10
<212> TYPE: PRT
<213> ORGANISM: Zaire ebolavirus

<400> SEQUENCE: 46

Leu Ser Leu Leu Cys Glu Thr His Leu Arg
1               5                   10

<210> SEQ ID NO 47
```

```
<211> LENGTH: 9
<212> TYPE: PRT
<213> ORGANISM: Zaire ebolavirus

<400> SEQUENCE: 47

Met Phe Ile Thr Ala Phe Leu Asn Ile
1               5

<210> SEQ ID NO 48
<211> LENGTH: 9
<212> TYPE: PRT
<213> ORGANISM: Zaire ebolavirus

<400> SEQUENCE: 48

Glu Phe Val Leu Pro Pro Val Gln Leu
1               5

<210> SEQ ID NO 49
<211> LENGTH: 6
<212> TYPE: PRT
<213> ORGANISM: Zaire ebolavirus

<400> SEQUENCE: 49

Phe Leu Val Pro Pro Val
1               5

<210> SEQ ID NO 50
<211> LENGTH: 11
<212> TYPE: PRT
<213> ORGANISM: Zaire ebolavirus

<400> SEQUENCE: 50

Gln Tyr Phe Thr Phe Asp Leu Thr Ala Leu Lys
1               5                   10

<210> SEQ ID NO 51
<211> LENGTH: 9
<212> TYPE: PRT
<213> ORGANISM: Zaire ebolavirus

<400> SEQUENCE: 51

Thr Ser Pro Glu Lys Ile Gln Ala Ile
1               5

<210> SEQ ID NO 52
<211> LENGTH: 8
<212> TYPE: PRT
<213> ORGANISM: Zaire ebolavirus

<400> SEQUENCE: 52

Arg Ile Gly Asn Gln Ala Phe Leu
1               5

<210> SEQ ID NO 53
<211> LENGTH: 8
<212> TYPE: PRT
<213> ORGANISM: Zaire ebolavirus

<400> SEQUENCE: 53

Gln Ala Phe Leu Gln Glu Phe Val
1               5

<210> SEQ ID NO 54
<211> LENGTH: 15
<212> TYPE: PRT
```

```
<213> ORGANISM: Zaire ebolavirus

<400> SEQUENCE: 54

Trp Ile Pro Tyr Phe Gly Pro Ala Ala Glu Gly Ile Tyr Thr Glu
1               5                   10                  15

<210> SEQ ID NO 55
<211> LENGTH: 15
<212> TYPE: PRT
<213> ORGANISM: Zaire ebolavirus

<400> SEQUENCE: 55

Asn Gln Leu Arg Ser Val Gly Leu Asn Leu Glu Gly Asn Gly Val
1               5                   10                  15

<210> SEQ ID NO 56
<211> LENGTH: 15
<212> TYPE: PRT
<213> ORGANISM: Zaire ebolavirus

<400> SEQUENCE: 56

Pro Asp Gly Ile Arg Gly Phe Pro Arg Cys Arg Tyr Val His Lys
1               5                   10                  15

<210> SEQ ID NO 57
<211> LENGTH: 15
<212> TYPE: PRT
<213> ORGANISM: Zaire ebolavirus

<400> SEQUENCE: 57

Glu Tyr Leu Phe Glu Val Asp Asn Leu Thr Tyr Val Gln Leu Glu
1               5                   10                  15

<210> SEQ ID NO 58
<211> LENGTH: 15
<212> TYPE: PRT
<213> ORGANISM: Zaire ebolavirus

<400> SEQUENCE: 58

Asn Leu Thr Arg Lys Ile Arg Ser Glu Glu Leu Ser Phe Thr Val
1               5                   10                  15

<210> SEQ ID NO 59
<211> LENGTH: 15
<212> TYPE: PRT
<213> ORGANISM: Zaire ebolavirus

<400> SEQUENCE: 59

His Ser Phe Glu Glu Met Tyr Arg His Ile Leu Arg Ser Gln Gly
1               5                   10                  15

<210> SEQ ID NO 60
<211> LENGTH: 15
<212> TYPE: PRT
<213> ORGANISM: Zaire ebolavirus

<400> SEQUENCE: 60

Asn Thr Gln Ser Glu His Ser Phe Glu Glu Met Tyr Arg His Ile
1               5                   10                  15

<210> SEQ ID NO 61
<211> LENGTH: 15
<212> TYPE: PRT
<213> ORGANISM: Zaire ebolavirus
```

```
<400> SEQUENCE: 61

Thr Gln Gly Ser Ser Thr Arg Met Gln Ser Leu Ile Leu Glu Phe
1               5                   10                  15

<210> SEQ ID NO 62
<211> LENGTH: 15
<212> TYPE: PRT
<213> ORGANISM: Zaire ebolavirus

<400> SEQUENCE: 62

Val Tyr Asp Met Ala Lys Thr Ile Ser Ser Leu Asn Arg Val Cys
1               5                   10                  15

<210> SEQ ID NO 63
<211> LENGTH: 15
<212> TYPE: PRT
<213> ORGANISM: Zaire ebolavirus

<400> SEQUENCE: 63

Phe Ala Glu Gly Val Val Ala Phe Leu Ile Leu Pro Gln Ala Lys
1               5                   10                  15

<210> SEQ ID NO 64
<211> LENGTH: 15
<212> TYPE: PRT
<213> ORGANISM: Zaire ebolavirus

<400> SEQUENCE: 64

Tyr Thr Ser Gly Lys Arg Ser Asn Thr Thr Gly Lys Leu Ile Trp
1               5                   10                  15

<210> SEQ ID NO 65
<211> LENGTH: 15
<212> TYPE: PRT
<213> ORGANISM: Zaire ebolavirus

<400> SEQUENCE: 65

Arg Ser Asn Thr Thr Gly Lys Leu Ile Trp Lys Val Asn Pro Glu
1               5                   10                  15

<210> SEQ ID NO 66
<211> LENGTH: 15
<212> TYPE: PRT
<213> ORGANISM: Zaire ebolavirus

<400> SEQUENCE: 66

Gly Lys Leu Ile Trp Lys Val Asn Pro Glu Ile Asp Thr Thr Ile
1               5                   10                  15

<210> SEQ ID NO 67
<211> LENGTH: 15
<212> TYPE: PRT
<213> ORGANISM: Zaire ebolavirus

<400> SEQUENCE: 67

Lys Val Asn Pro Glu Ile Asp Thr Thr Ile Gly Glu Trp Ala Phe
1               5                   10                  15

<210> SEQ ID NO 68
<211> LENGTH: 15
<212> TYPE: PRT
<213> ORGANISM: Zaire ebolavirus

<400> SEQUENCE: 68
```

```
Ile Asp Thr Thr Ile Gly Glu Trp Ala Phe Trp Glu Thr Lys Lys
1               5                   10                  15
```

<210> SEQ ID NO 69
<211> LENGTH: 15
<212> TYPE: PRT
<213> ORGANISM: Zaire ebolavirus

<400> SEQUENCE: 69

```
Gly Glu Trp Ala Phe Trp Glu Thr Lys Lys Asn Leu Thr Arg Lys
1               5                   10                  15
```

<210> SEQ ID NO 70
<211> LENGTH: 15
<212> TYPE: PRT
<213> ORGANISM: Zaire ebolavirus

<400> SEQUENCE: 70

```
Trp Glu Thr Lys Lys Asn Leu Thr Arg Lys Ile Arg Ser Glu Glu
1               5                   10                  15
```

<210> SEQ ID NO 71
<211> LENGTH: 15
<212> TYPE: PRT
<213> ORGANISM: Zaire ebolavirus

<400> SEQUENCE: 71

```
Asn Leu Thr Arg Lys Ile Arg Ser Glu Glu Leu Ser Phe Thr Val
1               5                   10                  15
```

<210> SEQ ID NO 72
<211> LENGTH: 15
<212> TYPE: PRT
<213> ORGANISM: Zaire ebolavirus

<400> SEQUENCE: 72

```
Ile Arg Ser Glu Glu Leu Ser Phe Thr Val Val Ser Asn Gly Ala
1               5                   10                  15
```

<210> SEQ ID NO 73
<211> LENGTH: 15
<212> TYPE: PRT
<213> ORGANISM: Zaire ebolavirus

<400> SEQUENCE: 73

```
Leu Ser Phe Thr Val Val Ser Asn Gly Ala Lys Asn Ile Ser Gly
1               5                   10                  15
```

<210> SEQ ID NO 74
<211> LENGTH: 15
<212> TYPE: PRT
<213> ORGANISM: Zaire ebolavirus

<400> SEQUENCE: 74

```
Val Ser Asn Gly Ala Lys Asn Ile Ser Gly Gln Ser Pro Ala Arg
1               5                   10                  15
```

<210> SEQ ID NO 75
<211> LENGTH: 15
<212> TYPE: PRT
<213> ORGANISM: Zaire ebolavirus

<400> SEQUENCE: 75

```
Lys Asn Ile Ser Gly Gln Ser Pro Ala Arg Thr Ser Ser Asp Pro
1               5                   10                  15
```

<210> SEQ ID NO 76
<211> LENGTH: 15
<212> TYPE: PRT
<213> ORGANISM: Zaire ebolavirus

<400> SEQUENCE: 76

Gln Ser Pro Ala Arg Thr Ser Ser Asp Pro Gly Thr Asn Thr Thr
1               5                   10                  15

<210> SEQ ID NO 77
<211> LENGTH: 15
<212> TYPE: PRT
<213> ORGANISM: Zaire ebolavirus

<400> SEQUENCE: 77

Asn Arg Lys Ala Ile Asp Phe Leu Leu Gln Arg Trp Gly Gly Thr
1               5                   10                  15

<210> SEQ ID NO 78
<211> LENGTH: 15
<212> TYPE: PRT
<213> ORGANISM: Zaire ebolavirus

<400> SEQUENCE: 78

Asp Phe Leu Leu Gln Arg Trp Gly Gly Thr Cys His Ile Leu Gly
1               5                   10                  15

<210> SEQ ID NO 79
<211> LENGTH: 15
<212> TYPE: PRT
<213> ORGANISM: Zaire ebolavirus

<400> SEQUENCE: 79

Arg Trp Gly Gly Thr Cys His Ile Leu Gly Pro Asp Cys Cys Ile
1               5                   10                  15

<210> SEQ ID NO 80
<211> LENGTH: 15
<212> TYPE: PRT
<213> ORGANISM: Zaire ebolavirus

<400> SEQUENCE: 80

Cys His Ile Leu Gly Pro Asp Cys Cys Ile Glu Pro His Asp Trp
1               5                   10                  15

<210> SEQ ID NO 81
<211> LENGTH: 15
<212> TYPE: PRT
<213> ORGANISM: Zaire ebolavirus

<400> SEQUENCE: 81

Pro Asp Cys Cys Ile Glu Pro His Asp Trp Thr Lys Asn Ile Thr
1               5                   10                  15

<210> SEQ ID NO 82
<211> LENGTH: 15
<212> TYPE: PRT
<213> ORGANISM: Zaire ebolavirus

<400> SEQUENCE: 82

Glu Pro His Asp Trp Thr Lys Asn Ile Thr Asp Lys Ile Asp Gln
1               5                   10                  15

-continued

<210> SEQ ID NO 83
<211> LENGTH: 15
<212> TYPE: PRT
<213> ORGANISM: Zaire ebolavirus

<400> SEQUENCE: 83

Thr Lys Asn Ile Thr Asp Lys Ile Asp Gln Ile Ile His Asp Phe
1               5                   10                  15

<210> SEQ ID NO 84
<211> LENGTH: 15
<212> TYPE: PRT
<213> ORGANISM: Zaire ebolavirus

<400> SEQUENCE: 84

Asp Lys Ile Asp Gln Ile Ile His Asp Phe Val Asp Lys Thr Leu
1               5                   10                  15

<210> SEQ ID NO 85
<211> LENGTH: 15
<212> TYPE: PRT
<213> ORGANISM: Zaire ebolavirus

<400> SEQUENCE: 85

Ile Ile His Asp Phe Val Asp Lys Thr Leu Pro Asp Gln Gly Asp
1               5                   10                  15

<210> SEQ ID NO 86
<211> LENGTH: 15
<212> TYPE: PRT
<213> ORGANISM: Zaire ebolavirus

<400> SEQUENCE: 86

Val Asp Lys Thr Leu Pro Asp Gln Gly Asp Asn Asp Asn Trp Trp
1               5                   10                  15

<210> SEQ ID NO 87
<211> LENGTH: 15
<212> TYPE: PRT
<213> ORGANISM: Zaire ebolavirus

<400> SEQUENCE: 87

Pro Asp Gln Gly Asp Asn Asp Asn Trp Trp Thr Gly Trp Arg Gln
1               5                   10                  15

<210> SEQ ID NO 88
<211> LENGTH: 15
<212> TYPE: PRT
<213> ORGANISM: Zaire ebolavirus

<400> SEQUENCE: 88

Asn Asp Asn Trp Trp Thr Gly Trp Arg Gln Trp Ile Pro Ala Gly
1               5                   10                  15

<210> SEQ ID NO 89
<211> LENGTH: 15
<212> TYPE: PRT
<213> ORGANISM: Zaire ebolavirus

<400> SEQUENCE: 89

Thr Gly Trp Arg Gln Trp Ile Pro Ala Gly Ile Gly Val Thr Gly
1               5                   10                  15

<210> SEQ ID NO 90
<211> LENGTH: 15

```
<212> TYPE: PRT
<213> ORGANISM: Zaire ebolavirus

<400> SEQUENCE: 90

Thr Ile Glu Ser Pro Leu Trp Ala Leu Arg Val Ile Leu Ala Ala
1               5                   10                  15

<210> SEQ ID NO 91
<211> LENGTH: 15
<212> TYPE: PRT
<213> ORGANISM: Zaire ebolavirus

<400> SEQUENCE: 91

Gly Gln Pro Ile Ile Pro Val Leu Leu Pro Lys Tyr Ile Gly Leu
1               5                   10                  15

<210> SEQ ID NO 92
<211> LENGTH: 15
<212> TYPE: PRT
<213> ORGANISM: Zaire ebolavirus

<400> SEQUENCE: 92

Lys Val Asn Pro Glu Ile Asp Thr Thr Ile Gly Glu Trp Ala Phe
1               5                   10                  15

<210> SEQ ID NO 93
<211> LENGTH: 15
<212> TYPE: PRT
<213> ORGANISM: Zaire ebolavirus

<400> SEQUENCE: 93

Ile Asp Thr Thr Ile Gly Glu Trp Ala Phe Trp Glu Thr Lys Lys
1               5                   10                  15

<210> SEQ ID NO 94
<211> LENGTH: 15
<212> TYPE: PRT
<213> ORGANISM: Zaire ebolavirus

<400> SEQUENCE: 94

Ala Ala Gly Pro Leu Lys Ala Glu Asn Thr Asn Thr Ser Lys Gly
1               5                   10                  15

<210> SEQ ID NO 95
<211> LENGTH: 15
<212> TYPE: PRT
<213> ORGANISM: Zaire ebolavirus

<400> SEQUENCE: 95

Lys Ala Glu Asn Thr Asn Thr Ser Lys Gly Thr Asp Leu Leu Asp
1               5                   10                  15

<210> SEQ ID NO 96
<211> LENGTH: 15
<212> TYPE: PRT
<213> ORGANISM: Zaire ebolavirus

<400> SEQUENCE: 96

Trp Ile Pro Ala Gly Ile Gly Val Thr Gly Val Ile Ile Ala Val
1               5                   10                  15

<210> SEQ ID NO 97
<211> LENGTH: 15
<212> TYPE: PRT
<213> ORGANISM: Zaire ebolavirus
```

```
<400> SEQUENCE: 97

Ile Gly Val Thr Gly Val Ile Ile Ala Val Ile Ala Leu Phe Cys
1               5                  10                  15

<210> SEQ ID NO 98
<211> LENGTH: 15
<212> TYPE: PRT
<213> ORGANISM: Zaire ebolavirus

<400> SEQUENCE: 98

Val Ile Ile Ala Val Ile Ala Leu Phe Cys Ile Cys Lys Phe Val
1               5                  10                  15

<210> SEQ ID NO 99
<211> LENGTH: 15
<212> TYPE: PRT
<213> ORGANISM: Zaire ebolavirus

<400> SEQUENCE: 99

Ile Ile Ala Val Ile Ala Leu Phe Cys Ile Cys Lys Phe Val Phe
1               5                  10                  15

<210> SEQ ID NO 100
<211> LENGTH: 15
<212> TYPE: PRT
<213> ORGANISM: Zaire ebolavirus

<400> SEQUENCE: 100

Asn Leu Thr Arg Lys Ile Arg Ser Glu Glu Leu Ser Phe Ser Ala
1               5                  10                  15

<210> SEQ ID NO 101
<211> LENGTH: 15
<212> TYPE: PRT
<213> ORGANISM: Zaire ebolavirus

<400> SEQUENCE: 101

Ile Arg Ser Glu Glu Leu Ser Phe Ser Ala Val Ser Asn Arg Ala
1               5                  10                  15

<210> SEQ ID NO 102
<211> LENGTH: 15
<212> TYPE: PRT
<213> ORGANISM: Zaire ebolavirus

<400> SEQUENCE: 102

Leu Ser Phe Ser Ala Val Ser Asn Arg Ala Lys Asn Ile Ser Gly
1               5                  10                  15

<210> SEQ ID NO 103
<211> LENGTH: 15
<212> TYPE: PRT
<213> ORGANISM: Zaire ebolavirus

<400> SEQUENCE: 103

Val Ser Asn Arg Ala Lys Asn Ile Ser Gly Gln Ser Pro Ala Arg
1               5                  10                  15

<210> SEQ ID NO 104
<211> LENGTH: 15
<212> TYPE: PRT
<213> ORGANISM: Zaire ebolavirus

<400> SEQUENCE: 104
```

```
Gln Gly Arg Glu Ala Ala Val Ser His Leu Thr Thr Leu Gly Thr
1               5                   10                  15

<210> SEQ ID NO 105
<211> LENGTH: 15
<212> TYPE: PRT
<213> ORGANISM: Zaire ebolavirus

<400> SEQUENCE: 105

Ala Val Ser His Leu Thr Thr Leu Gly Thr Ile Ser Thr Ser Pro
1               5                   10                  15

<210> SEQ ID NO 106
<211> LENGTH: 15
<212> TYPE: PRT
<213> ORGANISM: Zaire ebolavirus

<400> SEQUENCE: 106

Thr Thr Leu Gly Thr Ile Ser Thr Ser Pro Gln Pro Pro Thr Thr
1               5                   10                  15

<210> SEQ ID NO 107
<211> LENGTH: 15
<212> TYPE: PRT
<213> ORGANISM: Zaire ebolavirus

<400> SEQUENCE: 107

Ile Ser Thr Ser Pro Gln Pro Pro Thr Thr Lys Pro Gly Pro Asp
1               5                   10                  15

<210> SEQ ID NO 108
<211> LENGTH: 15
<212> TYPE: PRT
<213> ORGANISM: Zaire ebolavirus

<400> SEQUENCE: 108

Gln Pro Pro Thr Thr Lys Pro Gly Pro Asp Asn Ser Thr His Asn
1               5                   10                  15

<210> SEQ ID NO 109
<211> LENGTH: 15
<212> TYPE: PRT
<213> ORGANISM: Zaire ebolavirus

<400> SEQUENCE: 109

Thr Asp Asn Asp Ser Thr Ala Ser Asp Thr Pro Pro Ala Thr Thr
1               5                   10                  15

<210> SEQ ID NO 110
<211> LENGTH: 15
<212> TYPE: PRT
<213> ORGANISM: Zaire ebolavirus

<400> SEQUENCE: 110

Thr Ala Ser Asp Thr Pro Pro Ala Thr Thr Ala Ala Gly Pro Leu
1               5                   10                  15

<210> SEQ ID NO 111
<211> LENGTH: 15
<212> TYPE: PRT
<213> ORGANISM: Zaire ebolavirus

<400> SEQUENCE: 111

Pro Pro Ala Thr Thr Ala Ala Gly Pro Leu Lys Ala Glu Asn Thr
```

```
1               5                  10                  15
```

<210> SEQ ID NO 112
<211> LENGTH: 15
<212> TYPE: PRT
<213> ORGANISM: Zaire ebolavirus

<400> SEQUENCE: 112

```
Ala Ala Gly Pro Leu Lys Ala Glu Asn Thr Asn Thr Ser Lys Gly
1               5                   10                  15
```

<210> SEQ ID NO 113
<211> LENGTH: 15
<212> TYPE: PRT
<213> ORGANISM: Zaire ebolavirus

<400> SEQUENCE: 113

```
Lys Ala Glu Asn Thr Asn Thr Ser Lys Gly Thr Asp Leu Leu Asp
1               5                   10                  15
```

<210> SEQ ID NO 114
<211> LENGTH: 15
<212> TYPE: PRT
<213> ORGANISM: Zaire ebolavirus

<400> SEQUENCE: 114

```
Asn Thr Ser Lys Gly Thr Asp Leu Leu Asp Pro Ala Thr Thr Thr
1               5                   10                  15
```

<210> SEQ ID NO 115
<211> LENGTH: 15
<212> TYPE: PRT
<213> ORGANISM: Zaire ebolavirus

<400> SEQUENCE: 115

```
Thr Asp Leu Leu Asp Pro Ala Thr Thr Thr Ser Pro Gln Asn His
1               5                   10                  15
```

<210> SEQ ID NO 116
<211> LENGTH: 15
<212> TYPE: PRT
<213> ORGANISM: Zaire ebolavirus

<400> SEQUENCE: 116

```
Ile Ala Gly Val Ala Gly Leu Ile Thr Gly Gly Arg Arg Ala Arg
1               5                   10                  15
```

<210> SEQ ID NO 117
<211> LENGTH: 15
<212> TYPE: PRT
<213> ORGANISM: Zaire ebolavirus

<400> SEQUENCE: 117

```
Gly Leu Ile Thr Gly Gly Arg Arg Ala Arg Arg Glu Ala Ile Val
1               5                   10                  15
```

<210> SEQ ID NO 118
<211> LENGTH: 15
<212> TYPE: PRT
<213> ORGANISM: Zaire ebolavirus

<400> SEQUENCE: 118

```
Gly Arg Arg Ala Arg Arg Glu Ala Ile Val Asn Ala Gln Pro Lys
1               5                   10                  15
```

```
<210> SEQ ID NO 119
<211> LENGTH: 15
<212> TYPE: PRT
<213> ORGANISM: Zaire ebolavirus

<400> SEQUENCE: 119

Trp Ile Pro Tyr Phe Gly Pro Ala Ala Glu Gly Ile Tyr Thr Glu
1               5                   10                  15

<210> SEQ ID NO 120
<211> LENGTH: 15
<212> TYPE: PRT
<213> ORGANISM: Zaire ebolavirus

<400> SEQUENCE: 120

Gly Pro Ala Ala Glu Gly Ile Tyr Thr Glu Gly Leu Met His Asn
1               5                   10                  15

<210> SEQ ID NO 121
<211> LENGTH: 15
<212> TYPE: PRT
<213> ORGANISM: Zaire ebolavirus

<400> SEQUENCE: 121

Gly Ile Tyr Thr Glu Gly Leu Met His Asn Gln Asp Gly Leu Phe
1               5                   10                  15

<210> SEQ ID NO 122
<211> LENGTH: 15
<212> TYPE: PRT
<213> ORGANISM: Zaire ebolavirus

<400> SEQUENCE: 122

Phe Ser Ile Pro Leu Gly Val Ile His Asn Ser Thr Leu Gln Val
1               5                   10                  15

<210> SEQ ID NO 123
<211> LENGTH: 15
<212> TYPE: PRT
<213> ORGANISM: Zaire ebolavirus

<400> SEQUENCE: 123

Val Val Asn Tyr Glu Ala Gly Glu Trp Ala Glu Asn Cys Tyr Asn
1               5                   10                  15

<210> SEQ ID NO 124
<211> LENGTH: 15
<212> TYPE: PRT
<213> ORGANISM: Zaire ebolavirus

<400> SEQUENCE: 124

Leu Tyr Asp Arg Leu Ala Ser Thr Val Ile Tyr Arg Gly Thr Thr
1               5                   10                  15

<210> SEQ ID NO 125
<211> LENGTH: 15
<212> TYPE: PRT
<213> ORGANISM: Zaire ebolavirus

<400> SEQUENCE: 125

Gly Thr Asn Glu Thr Glu Tyr Leu Phe Glu Val Asp Asn Leu Thr
1               5                   10                  15

<210> SEQ ID NO 126
```

```
<211> LENGTH: 15
<212> TYPE: PRT
<213> ORGANISM: Zaire ebolavirus

<400> SEQUENCE: 126

Trp Glu Thr Lys Lys Asn Leu Thr Arg Lys Ile Arg Ser Glu Glu
1               5                   10                  15

<210> SEQ ID NO 127
<211> LENGTH: 15
<212> TYPE: PRT
<213> ORGANISM: Zaire ebolavirus

<400> SEQUENCE: 127

Gln Gly Arg Glu Ala Ala Val Ser His Leu Thr Thr Leu Ala Thr
1               5                   10                  15

<210> SEQ ID NO 128
<211> LENGTH: 15
<212> TYPE: PRT
<213> ORGANISM: Zaire ebolavirus

<400> SEQUENCE: 128

Pro Ser Ala Thr Thr Ala Ala Gly Pro Pro Lys Ala Glu Asn Thr
1               5                   10                  15

<210> SEQ ID NO 129
<211> LENGTH: 15
<212> TYPE: PRT
<213> ORGANISM: Zaire ebolavirus

<400> SEQUENCE: 129

Ile Ala Gly Val Ala Gly Leu Ile Thr Gly Gly Arg Arg Thr Arg
1               5                   10                  15

<210> SEQ ID NO 130
<211> LENGTH: 15
<212> TYPE: PRT
<213> ORGANISM: Zaire ebolavirus

<400> SEQUENCE: 130

Gln Asp Gly Leu Ile Cys Gly Leu Arg Gln Leu Ala Asn Glu Thr
1               5                   10                  15

<210> SEQ ID NO 131
<211> LENGTH: 15
<212> TYPE: PRT
<213> ORGANISM: Zaire ebolavirus

<400> SEQUENCE: 131

Thr Lys Asn Ile Thr Asp Lys Ile Asp Gln Ile Ile His Asp Phe
1               5                   10                  15

<210> SEQ ID NO 132
<211> LENGTH: 15
<212> TYPE: PRT
<213> ORGANISM: Zaire ebolavirus

<400> SEQUENCE: 132

Leu Ser Phe Ser Ala Val Ser Asn Arg Ala Lys Asn Ile Ser Gly
1               5                   10                  15

<210> SEQ ID NO 133
<211> LENGTH: 15
<212> TYPE: PRT
```

<213> ORGANISM: Zaire ebolavirus

<400> SEQUENCE: 133

Thr Asp Leu Leu Asp Pro Ala Thr Thr Thr Ser Pro Gln Asn His
1               5                   10                  15

<210> SEQ ID NO 134
<211> LENGTH: 15
<212> TYPE: PRT
<213> ORGANISM: Zaire ebolavirus

<400> SEQUENCE: 134

Gly Val Ile His Asn Ser Thr Leu Gln Val Ser Asp Val Asp Lys
1               5                   10                  15

<210> SEQ ID NO 135
<211> LENGTH: 15
<212> TYPE: PRT
<213> ORGANISM: Zaire ebolavirus

<400> SEQUENCE: 135

Ala Gly Glu Trp Ala Glu Asn Cys Tyr Asn Leu Glu Ile Lys Lys
1               5                   10                  15

<210> SEQ ID NO 136
<211> LENGTH: 15
<212> TYPE: PRT
<213> ORGANISM: Zaire ebolavirus

<400> SEQUENCE: 136

Ala Ser Thr Val Ile Tyr Arg Gly Thr Thr Phe Ala Glu Gly Val
1               5                   10                  15

<210> SEQ ID NO 137
<211> LENGTH: 15
<212> TYPE: PRT
<213> ORGANISM: Zaire ebolavirus

<400> SEQUENCE: 137

Glu Tyr Leu Phe Glu Val Asp Asn Leu Thr Tyr Val Gln Leu Glu
1               5                   10                  15

<210> SEQ ID NO 138
<211> LENGTH: 15
<212> TYPE: PRT
<213> ORGANISM: Zaire ebolavirus

<400> SEQUENCE: 138

Trp Glu Thr Lys Lys Asn Leu Thr Arg Lys Ile Arg Ser Glu Glu
1               5                   10                  15

<210> SEQ ID NO 139
<211> LENGTH: 15
<212> TYPE: PRT
<213> ORGANISM: Zaire ebolavirus

<400> SEQUENCE: 139

Ala Val Ser His Leu Thr Thr Leu Ala Thr Ile Ser Thr Ser Pro
1               5                   10                  15

<210> SEQ ID NO 140
<211> LENGTH: 15
<212> TYPE: PRT
<213> ORGANISM: Zaire ebolavirus

```
<400> SEQUENCE: 140

Ala Ala Gly Pro Pro Lys Ala Glu Asn Thr Asn Thr Ser Lys Ser
1               5                   10                  15

<210> SEQ ID NO 141
<211> LENGTH: 15
<212> TYPE: PRT
<213> ORGANISM: Zaire ebolavirus

<400> SEQUENCE: 141

Gly Leu Ile Thr Gly Gly Arg Arg Thr Arg Arg Glu Ala Ile Val
1               5                   10                  15

<210> SEQ ID NO 142
<211> LENGTH: 15
<212> TYPE: PRT
<213> ORGANISM: Zaire ebolavirus

<400> SEQUENCE: 142

Cys Gly Leu Arg Gln Leu Ala Asn Glu Thr Thr Gln Ala Leu Gln
1               5                   10                  15

<210> SEQ ID NO 143
<211> LENGTH: 15
<212> TYPE: PRT
<213> ORGANISM: Zaire ebolavirus

<400> SEQUENCE: 143

Asp Lys Ile Asp Gln Ile Ile His Asp Phe Val Asp Lys Thr Leu
1               5                   10                  15

<210> SEQ ID NO 144
<211> LENGTH: 15
<212> TYPE: PRT
<213> ORGANISM: Zaire ebolavirus

<400> SEQUENCE: 144

Val Ser Asn Arg Ala Lys Asn Ile Ser Gly Gln Ser Pro Ala Arg
1               5                   10                  15

<210> SEQ ID NO 145
<211> LENGTH: 15
<212> TYPE: PRT
<213> ORGANISM: Zaire ebolavirus

<400> SEQUENCE: 145

Ile Ala Gly Val Ala Gly Leu Ile Thr Gly Gly Arg Arg Ala Arg
1               5                   10                  15

<210> SEQ ID NO 146
<211> LENGTH: 15
<212> TYPE: PRT
<213> ORGANISM: Zaire ebolavirus

<400> SEQUENCE: 146

Val Ile Ile Ala Val Ile Ala Leu Phe Cys Ile Cys Lys Phe Val
1               5                   10                  15

<210> SEQ ID NO 147
<211> LENGTH: 15
<212> TYPE: PRT
<213> ORGANISM: Zaire ebolavirus

<400> SEQUENCE: 147
```

Ser His Pro Leu Arg Glu Pro Val Asn Ala Thr Glu Asp Pro Ser
1               5                   10                  15

<210> SEQ ID NO 148
<211> LENGTH: 15
<212> TYPE: PRT
<213> ORGANISM: Zaire ebolavirus

<400> SEQUENCE: 148

Glu Pro Val Asn Ala Thr Glu Asp Pro Ser Ser Gly Tyr Tyr Ser
1               5                   10                  15

<210> SEQ ID NO 149
<211> LENGTH: 15
<212> TYPE: PRT
<213> ORGANISM: Zaire ebolavirus

<400> SEQUENCE: 149

Thr Glu Asp Pro Ser Ser Gly Tyr Tyr Ser Thr Thr Ile Arg Tyr
1               5                   10                  15

<210> SEQ ID NO 150
<211> LENGTH: 15
<212> TYPE: PRT
<213> ORGANISM: Zaire ebolavirus

<400> SEQUENCE: 150

Ser Gly Tyr Tyr Ser Thr Thr Ile Arg Tyr Gln Ala Thr Gly Phe
1               5                   10                  15

<210> SEQ ID NO 151
<211> LENGTH: 15
<212> TYPE: PRT
<213> ORGANISM: Zaire ebolavirus

<400> SEQUENCE: 151

Thr Thr Ile Arg Tyr Gln Ala Thr Gly Phe Gly Thr Asn Glu Thr
1               5                   10                  15

<210> SEQ ID NO 152
<211> LENGTH: 15
<212> TYPE: PRT
<213> ORGANISM: Zaire ebolavirus

<400> SEQUENCE: 152

Gln Ala Thr Gly Phe Gly Thr Asn Glu Thr Glu Tyr Leu Phe Glu
1               5                   10                  15

<210> SEQ ID NO 153
<211> LENGTH: 15
<212> TYPE: PRT
<213> ORGANISM: Zaire ebolavirus

<400> SEQUENCE: 153

Gly Thr Asn Glu Thr Glu Tyr Leu Phe Glu Val Asp Asn Leu Thr
1               5                   10                  15

<210> SEQ ID NO 154
<211> LENGTH: 15
<212> TYPE: PRT
<213> ORGANISM: Zaire ebolavirus

<400> SEQUENCE: 154

Glu Tyr Leu Phe Glu Val Asp Asn Leu Thr Tyr Val Gln Leu Glu
1               5                   10                  15

```
<210> SEQ ID NO 155
<211> LENGTH: 15
<212> TYPE: PRT
<213> ORGANISM: Zaire ebolavirus

<400> SEQUENCE: 155

Val Asp Asn Leu Thr Tyr Val Gln Leu Glu Ser Arg Phe Thr Pro
1               5                   10                  15

<210> SEQ ID NO 156
<211> LENGTH: 15
<212> TYPE: PRT
<213> ORGANISM: Zaire ebolavirus

<400> SEQUENCE: 156

Tyr Val Gln Leu Glu Ser Arg Phe Thr Pro Gln Phe Leu Leu Gln
1               5                   10                  15

<210> SEQ ID NO 157
<211> LENGTH: 15
<212> TYPE: PRT
<213> ORGANISM: Zaire ebolavirus

<400> SEQUENCE: 157

Ser Arg Phe Thr Pro Gln Phe Leu Leu Gln Leu Asn Glu Thr Ile
1               5                   10                  15

<210> SEQ ID NO 158
<211> LENGTH: 15
<212> TYPE: PRT
<213> ORGANISM: Zaire ebolavirus

<400> SEQUENCE: 158

Gln Phe Leu Leu Gln Leu Asn Glu Thr Ile Tyr Thr Ser Gly Lys
1               5                   10                  15

<210> SEQ ID NO 159
<211> LENGTH: 15
<212> TYPE: PRT
<213> ORGANISM: Zaire ebolavirus

<400> SEQUENCE: 159

Leu Asn Glu Thr Ile Tyr Thr Ser Gly Lys Arg Ser Asn Thr Thr
1               5                   10                  15

<210> SEQ ID NO 160
<211> LENGTH: 15
<212> TYPE: PRT
<213> ORGANISM: Zaire ebolavirus

<400> SEQUENCE: 160

Gln Asp Glu Gly Ala Ala Ile Gly Leu Ala Trp Ile Pro Tyr Phe
1               5                   10                  15

<210> SEQ ID NO 161
<211> LENGTH: 15
<212> TYPE: PRT
<213> ORGANISM: Zaire ebolavirus

<400> SEQUENCE: 161

Ala Ile Gly Leu Ala Trp Ile Pro Tyr Phe Gly Pro Ala Ala Glu
1               5                   10                  15
```

```
<210> SEQ ID NO 162
<211> LENGTH: 15
<212> TYPE: PRT
<213> ORGANISM: Zaire ebolavirus

<400> SEQUENCE: 162

Trp Ile Pro Tyr Phe Gly Pro Ala Ala Glu Gly Ile Tyr Thr Glu
1               5                   10                  15

<210> SEQ ID NO 163
<211> LENGTH: 15
<212> TYPE: PRT
<213> ORGANISM: Zaire ebolavirus

<400> SEQUENCE: 163

Gly Pro Ala Ala Glu Gly Ile Tyr Thr Glu Gly Leu Met His Asn
1               5                   10                  15

<210> SEQ ID NO 164
<211> LENGTH: 15
<212> TYPE: PRT
<213> ORGANISM: Zaire ebolavirus

<400> SEQUENCE: 164

Gly Ile Tyr Thr Glu Gly Leu Met His Asn Gln Asp Gly Leu Ile
1               5                   10                  15

<210> SEQ ID NO 165
<211> LENGTH: 15
<212> TYPE: PRT
<213> ORGANISM: Zaire ebolavirus

<400> SEQUENCE: 165

Gly Leu Met His Asn Gln Asp Gly Leu Ile Cys Gly Leu Arg Gln
1               5                   10                  15

<210> SEQ ID NO 166
<211> LENGTH: 15
<212> TYPE: PRT
<213> ORGANISM: Zaire ebolavirus

<400> SEQUENCE: 166

Gln Asp Gly Leu Ile Cys Gly Leu Arg Gln Leu Ala Asn Glu Thr
1               5                   10                  15

<210> SEQ ID NO 167
<211> LENGTH: 15
<212> TYPE: PRT
<213> ORGANISM: Zaire ebolavirus

<400> SEQUENCE: 167

Cys Gly Leu Arg Gln Leu Ala Asn Glu Thr Thr Gln Ala Leu Gln
1               5                   10                  15

<210> SEQ ID NO 168
<211> LENGTH: 15
<212> TYPE: PRT
<213> ORGANISM: Zaire ebolavirus

<400> SEQUENCE: 168

Leu Ala Asn Glu Thr Thr Gln Ala Leu Gln Leu Phe Leu Arg Ala
1               5                   10                  15

<210> SEQ ID NO 169
<211> LENGTH: 15
```

```
<212> TYPE: PRT
<213> ORGANISM: Zaire ebolavirus

<400> SEQUENCE: 169

Thr Gln Ala Leu Gln Leu Phe Leu Arg Ala Thr Thr Glu Leu Arg
1               5                   10                  15

<210> SEQ ID NO 170
<211> LENGTH: 15
<212> TYPE: PRT
<213> ORGANISM: Zaire ebolavirus

<400> SEQUENCE: 170

Leu Phe Leu Arg Ala Thr Thr Glu Leu Arg Thr Phe Ser Ile Leu
1               5                   10                  15

<210> SEQ ID NO 171
<211> LENGTH: 15
<212> TYPE: PRT
<213> ORGANISM: Zaire ebolavirus

<400> SEQUENCE: 171

Thr Thr Glu Leu Arg Thr Phe Ser Ile Leu Asn Arg Lys Ala Ile
1               5                   10                  15

<210> SEQ ID NO 172
<211> LENGTH: 15
<212> TYPE: PRT
<213> ORGANISM: Zaire ebolavirus

<400> SEQUENCE: 172

Thr Phe Ser Ile Leu Asn Arg Lys Ala Ile Asp Phe Leu Leu Gln
1               5                   10                  15

<210> SEQ ID NO 173
<211> LENGTH: 15
<212> TYPE: PRT
<213> ORGANISM: Zaire ebolavirus

<400> SEQUENCE: 173

Met Gly Val Thr Gly Ile Leu Gln Leu Pro Arg Asp Arg Phe Lys
1               5                   10                  15

<210> SEQ ID NO 174
<211> LENGTH: 15
<212> TYPE: PRT
<213> ORGANISM: Zaire ebolavirus

<400> SEQUENCE: 174

Ile Leu Gln Leu Pro Arg Asp Arg Phe Lys Arg Thr Ser Phe Phe
1               5                   10                  15

<210> SEQ ID NO 175
<211> LENGTH: 15
<212> TYPE: PRT
<213> ORGANISM: Zaire ebolavirus

<400> SEQUENCE: 175

Arg Asp Arg Phe Lys Arg Thr Ser Phe Phe Leu Trp Val Ile Ile
1               5                   10                  15

<210> SEQ ID NO 176
<211> LENGTH: 15
<212> TYPE: PRT
<213> ORGANISM: Zaire ebolavirus
```

```
<400> SEQUENCE: 176

Arg Thr Ser Phe Phe Leu Trp Val Ile Ile Leu Phe Gln Arg Thr
1               5                   10                  15

<210> SEQ ID NO 177
<211> LENGTH: 15
<212> TYPE: PRT
<213> ORGANISM: Zaire ebolavirus

<400> SEQUENCE: 177

Leu Trp Val Ile Ile Leu Phe Gln Arg Thr Phe Ser Ile Pro Leu
1               5                   10                  15

<210> SEQ ID NO 178
<211> LENGTH: 15
<212> TYPE: PRT
<213> ORGANISM: Zaire ebolavirus

<400> SEQUENCE: 178

Leu Phe Gln Arg Thr Phe Ser Ile Pro Leu Gly Val Ile His Asn
1               5                   10                  15

<210> SEQ ID NO 179
<211> LENGTH: 15
<212> TYPE: PRT
<213> ORGANISM: Zaire ebolavirus

<400> SEQUENCE: 179

Phe Ser Ile Pro Leu Gly Val Ile His Asn Ser Thr Leu Gln Val
1               5                   10                  15

<210> SEQ ID NO 180
<211> LENGTH: 15
<212> TYPE: PRT
<213> ORGANISM: Zaire ebolavirus

<400> SEQUENCE: 180

Gly Val Ile His Asn Ser Thr Leu Gln Val Ser Asp Val Asp Lys
1               5                   10                  15

<210> SEQ ID NO 181
<211> LENGTH: 15
<212> TYPE: PRT
<213> ORGANISM: Zaire ebolavirus

<400> SEQUENCE: 181

Ser Thr Leu Gln Val Ser Asp Val Asp Lys Leu Val Cys Arg Asp
1               5                   10                  15

<210> SEQ ID NO 182
<211> LENGTH: 15
<212> TYPE: PRT
<213> ORGANISM: Zaire ebolavirus

<400> SEQUENCE: 182

Ser Asp Val Asp Lys Leu Val Cys Arg Asp Lys Leu Ser Ser Thr
1               5                   10                  15

<210> SEQ ID NO 183
<211> LENGTH: 15
<212> TYPE: PRT
<213> ORGANISM: Zaire ebolavirus

<400> SEQUENCE: 183
```

```
Leu Val Cys Arg Asp Lys Leu Ser Ser Thr Asn Gln Leu Arg Ser
1               5                   10                  15

<210> SEQ ID NO 184
<211> LENGTH: 15
<212> TYPE: PRT
<213> ORGANISM: Zaire ebolavirus

<400> SEQUENCE: 184

Lys Leu Ser Ser Thr Asn Gln Leu Arg Ser Val Gly Leu Asn Leu
1               5                   10                  15

<210> SEQ ID NO 185
<211> LENGTH: 15
<212> TYPE: PRT
<213> ORGANISM: Zaire ebolavirus

<400> SEQUENCE: 185

Leu Val Cys Arg Asp Lys Leu Ser Ser Thr Asn Gln Leu Arg Ser
1               5                   10                  15

<210> SEQ ID NO 186
<211> LENGTH: 15
<212> TYPE: PRT
<213> ORGANISM: Zaire ebolavirus

<400> SEQUENCE: 186

Ile Leu Gln Leu Pro Arg Asp Arg Phe Lys Arg Thr Ser Phe Phe
1               5                   10                  15

<210> SEQ ID NO 187
<211> LENGTH: 15
<212> TYPE: PRT
<213> ORGANISM: Zaire ebolavirus

<400> SEQUENCE: 187

Glu Gly Asn Gly Val Ala Thr Asp Val Pro Ser Ala Thr Lys Arg
1               5                   10                  15

<210> SEQ ID NO 188
<211> LENGTH: 15
<212> TYPE: PRT
<213> ORGANISM: Zaire ebolavirus

<400> SEQUENCE: 188

Arg Tyr Val His Lys Val Ser Gly Thr Gly Pro Cys Ala Gly Asp
1               5                   10                  15

<210> SEQ ID NO 189
<211> LENGTH: 15
<212> TYPE: PRT
<213> ORGANISM: Zaire ebolavirus

<400> SEQUENCE: 189

Glu Pro Val Asn Ala Thr Glu Asp Pro Ser Ser Gly Tyr Tyr Ser
1               5                   10                  15

<210> SEQ ID NO 190
<211> LENGTH: 15
<212> TYPE: PRT
<213> ORGANISM: Zaire ebolavirus

<400> SEQUENCE: 190

Arg Ser Asn Thr Thr Gly Lys Leu Ile Trp Lys Val Asn Pro Glu
```

```
1               5                   10                  15
```

<210> SEQ ID NO 191
<211> LENGTH: 15
<212> TYPE: PRT
<213> ORGANISM: Zaire ebolavirus

<400> SEQUENCE: 191

```
Gly Thr Asn Thr Thr Thr Glu Asp His Lys Ile Met Ala Ser Glu
1               5                   10                  15
```

<210> SEQ ID NO 192
<211> LENGTH: 15
<212> TYPE: PRT
<213> ORGANISM: Zaire ebolavirus

<400> SEQUENCE: 192

```
Leu Asp Ile Ser Glu Ala Thr Gln Val Glu Gln His His Arg Arg
1               5                   10                  15
```

<210> SEQ ID NO 193
<211> LENGTH: 15
<212> TYPE: PRT
<213> ORGANISM: Zaire ebolavirus

<400> SEQUENCE: 193

```
Asn Asn Asn Thr His His Gln Asp Thr Gly Glu Glu Ser Ala Ser
1               5                   10                  15
```

<210> SEQ ID NO 194
<211> LENGTH: 15
<212> TYPE: PRT
<213> ORGANISM: Zaire ebolavirus

<400> SEQUENCE: 194

```
Ala Ile Gly Leu Ala Trp Ile Pro Tyr Phe Gly Pro Ala Ala Glu
1               5                   10                  15
```

<210> SEQ ID NO 195
<211> LENGTH: 15
<212> TYPE: PRT
<213> ORGANISM: Zaire ebolavirus

<400> SEQUENCE: 195

```
Asp Phe Leu Leu Gln Arg Trp Gly Gly Thr Cys His Ile Leu Gly
1               5                   10                  15
```

<210> SEQ ID NO 196
<211> LENGTH: 15
<212> TYPE: PRT
<213> ORGANISM: Zaire ebolavirus

<400> SEQUENCE: 196

```
Ile Gly Val Thr Gly Val Ile Ile Ala Val Ile Ala Leu Phe Cys
1               5                   10                  15
```

<210> SEQ ID NO 197
<211> LENGTH: 15
<212> TYPE: PRT
<213> ORGANISM: Zaire ebolavirus

<400> SEQUENCE: 197

```
Thr Ala Ser Asp Thr Pro Pro Ala Thr Thr Ala Ala Gly Pro Leu
1               5                   10                  15
```

```
<210> SEQ ID NO 198
<211> LENGTH: 15
<212> TYPE: PRT
<213> ORGANISM: Zaire ebolavirus

<400> SEQUENCE: 198

Arg Asp Arg Phe Lys Arg Thr Ser Phe Phe Leu Trp Val Ile Ile
1               5                   10                  15

<210> SEQ ID NO 199
<211> LENGTH: 15
<212> TYPE: PRT
<213> ORGANISM: Zaire ebolavirus

<400> SEQUENCE: 199

Ala Thr Asp Val Pro Ser Ala Thr Lys Arg Trp Gly Phe Arg Ser
1               5                   10                  15

<210> SEQ ID NO 200
<211> LENGTH: 15
<212> TYPE: PRT
<213> ORGANISM: Zaire ebolavirus

<400> SEQUENCE: 200

Val Ser Gly Thr Gly Pro Cys Ala Gly Asp Phe Ala Phe His Lys
1               5                   10                  15

<210> SEQ ID NO 201
<211> LENGTH: 15
<212> TYPE: PRT
<213> ORGANISM: Zaire ebolavirus

<400> SEQUENCE: 201

Thr Glu Asp Pro Ser Ser Gly Tyr Tyr Ser Thr Thr Ile Arg Tyr
1               5                   10                  15

<210> SEQ ID NO 202
<211> LENGTH: 15
<212> TYPE: PRT
<213> ORGANISM: Zaire ebolavirus

<400> SEQUENCE: 202

Gly Lys Leu Ile Trp Lys Val Asn Pro Glu Ile Asp Thr Thr Ile
1               5                   10                  15

<210> SEQ ID NO 203
<211> LENGTH: 15
<212> TYPE: PRT
<213> ORGANISM: Zaire ebolavirus

<400> SEQUENCE: 203

Thr Glu Asp His Lys Ile Met Ala Ser Glu Asn Ser Ser Ala Met
1               5                   10                  15

<210> SEQ ID NO 204
<211> LENGTH: 15
<212> TYPE: PRT
<213> ORGANISM: Zaire ebolavirus

<400> SEQUENCE: 204

Ala Thr Gln Val Glu Gln His His Arg Arg Thr Asp Asn Asp Ser
1               5                   10                  15

<210> SEQ ID NO 205
```

```
<211> LENGTH: 15
<212> TYPE: PRT
<213> ORGANISM: Zaire ebolavirus

<400> SEQUENCE: 205

His Gln Asp Thr Gly Glu Glu Ser Ala Ser Ser Gly Lys Leu Gly
1               5                   10                  15

<210> SEQ ID NO 206
<211> LENGTH: 15
<212> TYPE: PRT
<213> ORGANISM: Zaire ebolavirus

<400> SEQUENCE: 206

Trp Ile Pro Tyr Phe Gly Pro Ala Ala Glu Gly Ile Tyr Thr Glu
1               5                   10                  15

<210> SEQ ID NO 207
<211> LENGTH: 15
<212> TYPE: PRT
<213> ORGANISM: Zaire ebolavirus

<400> SEQUENCE: 207

Arg Trp Gly Gly Thr Cys His Ile Leu Gly Pro Asp Cys Cys Ile
1               5                   10                  15

<210> SEQ ID NO 208
<211> LENGTH: 15
<212> TYPE: PRT
<213> ORGANISM: Zaire ebolavirus

<400> SEQUENCE: 208

Val Ile Ile Ala Val Ile Ala Leu Phe Cys Ile Cys Lys Phe Val
1               5                   10                  15

<210> SEQ ID NO 209
<211> LENGTH: 15
<212> TYPE: PRT
<213> ORGANISM: Zaire ebolavirus

<400> SEQUENCE: 209

Pro Pro Ala Thr Thr Ala Ala Gly Pro Leu Lys Ala Glu Asn Thr
1               5                   10                  15

<210> SEQ ID NO 210
<211> LENGTH: 15
<212> TYPE: PRT
<213> ORGANISM: Zaire ebolavirus

<400> SEQUENCE: 210

Arg Thr Ser Phe Phe Leu Trp Val Ile Ile Leu Phe Gln Arg Thr
1               5                   10                  15

<210> SEQ ID NO 211
<211> LENGTH: 15
<212> TYPE: PRT
<213> ORGANISM: Zaire ebolavirus

<400> SEQUENCE: 211

Ser Ala Thr Lys Arg Trp Gly Phe Arg Ser Gly Val Pro Pro Lys
1               5                   10                  15

<210> SEQ ID NO 212
<211> LENGTH: 15
<212> TYPE: PRT
```

-continued

<213> ORGANISM: Zaire ebolavirus

<400> SEQUENCE: 212

Pro Cys Ala Gly Asp Phe Ala Phe His Lys Glu Gly Ala Phe Phe
1               5                   10                  15

<210> SEQ ID NO 213
<211> LENGTH: 15
<212> TYPE: PRT
<213> ORGANISM: Zaire ebolavirus

<400> SEQUENCE: 213

Ser Gly Tyr Tyr Ser Thr Thr Ile Arg Tyr Gln Ala Thr Gly Phe
1               5                   10                  15

<210> SEQ ID NO 214
<211> LENGTH: 15
<212> TYPE: PRT
<213> ORGANISM: Zaire ebolavirus

<400> SEQUENCE: 214

Lys Val Asn Pro Glu Ile Asp Thr Thr Ile Gly Glu Trp Ala Phe
1               5                   10                  15

<210> SEQ ID NO 215
<211> LENGTH: 15
<212> TYPE: PRT
<213> ORGANISM: Zaire ebolavirus

<400> SEQUENCE: 215

Ile Met Ala Ser Glu Asn Ser Ser Ala Met Val Gln Val His Ser
1               5                   10                  15

<210> SEQ ID NO 216
<211> LENGTH: 15
<212> TYPE: PRT
<213> ORGANISM: Zaire ebolavirus

<400> SEQUENCE: 216

Gln His His Arg Arg Thr Asp Asn Asp Ser Thr Ala Ser Asp Thr
1               5                   10                  15

<210> SEQ ID NO 217
<211> LENGTH: 15
<212> TYPE: PRT
<213> ORGANISM: Zaire ebolavirus

<400> SEQUENCE: 217

Glu Glu Ser Ala Ser Ser Gly Lys Leu Gly Leu Ile Thr Asn Thr
1               5                   10                  15

<210> SEQ ID NO 218
<211> LENGTH: 15
<212> TYPE: PRT
<213> ORGANISM: Zaire ebolavirus

<400> SEQUENCE: 218

Gly Pro Ala Ala Glu Gly Ile Tyr Thr Glu Gly Leu Met His Asn
1               5                   10                  15

<210> SEQ ID NO 219
<211> LENGTH: 15
<212> TYPE: PRT
<213> ORGANISM: Zaire ebolavirus -continued

<400> SEQUENCE: 219

Cys His Ile Leu Gly Pro Asp Cys Cys Ile Glu Pro His Asp Trp
1               5                   10                  15

<210> SEQ ID NO 220
<211> LENGTH: 15
<212> TYPE: PRT
<213> ORGANISM: Zaire ebolavirus

<400> SEQUENCE: 220

Ile Ile Ala Val Ile Ala Leu Phe Cys Ile Cys Lys Phe Val Phe
1               5                   10                  15

<210> SEQ ID NO 221
<211> LENGTH: 15
<212> TYPE: PRT
<213> ORGANISM: Zaire ebolavirus

<400> SEQUENCE: 221

Ala Ala Gly Pro Leu Lys Ala Glu Asn Thr Asn Thr Ser Lys Gly
1               5                   10                  15

<210> SEQ ID NO 222
<211> LENGTH: 15
<212> TYPE: PRT
<213> ORGANISM: Zaire ebolavirus

<400> SEQUENCE: 222

Val Arg Gln Arg Val Ile Pro Val Tyr Gln Val Asn Asn Leu Glu
1               5                   10                  15

<210> SEQ ID NO 223
<211> LENGTH: 15
<212> TYPE: PRT
<213> ORGANISM: Zaire ebolavirus

<400> SEQUENCE: 223

Gly His Gly Phe Arg Phe Glu Val Lys Lys Arg Asp Gly Val Lys
1               5                   10                  15

<210> SEQ ID NO 224
<211> LENGTH: 15
<212> TYPE: PRT
<213> ORGANISM: Zaire ebolavirus

<400> SEQUENCE: 224

Lys Ala Cys Leu Glu Lys Val Gln Arg Gln Ile Gln Val His Ala
1               5                   10                  15

<210> SEQ ID NO 225
<211> LENGTH: 15
<212> TYPE: PRT
<213> ORGANISM: Zaire ebolavirus

<400> SEQUENCE: 225

Val Ile Ser Asn Ser Val Ala Gln Ala Arg Phe Ser Gly Leu Leu
1               5                   10                  15

<210> SEQ ID NO 226
<211> LENGTH: 15
<212> TYPE: PRT
<213> ORGANISM: Zaire ebolavirus

<400> SEQUENCE: 226

```
Phe Ala Arg Leu Leu Asn Leu Ser Gly Val Asn Asn Leu Glu His
1               5                   10                  15

<210> SEQ ID NO 227
<211> LENGTH: 15
<212> TYPE: PRT
<213> ORGANISM: Zaire ebolavirus

<400> SEQUENCE: 227

Arg Glu Leu Asp His Leu Gly Leu Asp Asp Gln Glu Lys Lys Ile
1               5                   10                  15

<210> SEQ ID NO 228
<211> LENGTH: 15
<212> TYPE: PRT
<213> ORGANISM: Zaire ebolavirus

<400> SEQUENCE: 228

Asp Ile Pro Phe Pro Gly Pro Ile Asn Asp Asp Asp Asn Pro Gly
1               5                   10                  15

<210> SEQ ID NO 229
<211> LENGTH: 15
<212> TYPE: PRT
<213> ORGANISM: Zaire ebolavirus

<400> SEQUENCE: 229

Asp Asp Glu Asp Thr Lys Pro Val Pro Asn Arg Ser Thr Lys Gly
1               5                   10                  15

<210> SEQ ID NO 230
<211> LENGTH: 15
<212> TYPE: PRT
<213> ORGANISM: Zaire ebolavirus

<400> SEQUENCE: 230

Ser Thr Ser Pro Arg Met Leu Thr Pro Ile Asn Glu Glu Ala Asp
1               5                   10                  15

<210> SEQ ID NO 231
<211> LENGTH: 15
<212> TYPE: PRT
<213> ORGANISM: Zaire ebolavirus

<400> SEQUENCE: 231

Pro Gln Asp Glu Gln Gln Asp Gln Asp His Thr Gln Glu Ala Arg
1               5                   10                  15

<210> SEQ ID NO 232
<211> LENGTH: 15
<212> TYPE: PRT
<213> ORGANISM: Zaire ebolavirus

<400> SEQUENCE: 232

Tyr Thr Tyr Pro Asp Ser Leu Glu Glu Glu Tyr Pro Pro Trp Leu
1               5                   10                  15

<210> SEQ ID NO 233
<211> LENGTH: 15
<212> TYPE: PRT
<213> ORGANISM: Zaire ebolavirus

<400> SEQUENCE: 233

Leu Val Val Gly Glu Lys Ala Cys Leu Glu Lys Val Gln Arg Gln
1               5                   10                  15
```

```
<210> SEQ ID NO 234
<211> LENGTH: 15
<212> TYPE: PRT
<213> ORGANISM: Zaire ebolavirus

<400> SEQUENCE: 234

Thr Gln Glu Ala Arg Asn Gln Asp Ser Asp Asn Thr Gln Pro Glu
1               5                   10                  15

<210> SEQ ID NO 235
<211> LENGTH: 15
<212> TYPE: PRT
<213> ORGANISM: Zaire ebolavirus

<400> SEQUENCE: 235

Thr Ile Glu Asp Ser Lys Leu Arg Ala Leu Leu Thr Leu Cys Ala
1               5                   10                  15

<210> SEQ ID NO 236
<211> LENGTH: 15
<212> TYPE: PRT
<213> ORGANISM: Zaire ebolavirus

<400> SEQUENCE: 236

Lys Leu Arg Ala Leu Leu Thr Leu Cys Ala Val Met Thr Arg Lys
1               5                   10                  15

<210> SEQ ID NO 237
<211> LENGTH: 15
<212> TYPE: PRT
<213> ORGANISM: Zaire ebolavirus

<400> SEQUENCE: 237

Leu Thr Leu Cys Ala Val Met Thr Arg Lys Phe Ser Lys Ser Gln
1               5                   10                  15

<210> SEQ ID NO 238
<211> LENGTH: 15
<212> TYPE: PRT
<213> ORGANISM: Zaire ebolavirus

<400> SEQUENCE: 238

Val Met Thr Arg Lys Phe Ser Lys Ser Gln Leu Ser Leu Leu Cys
1               5                   10                  15

<210> SEQ ID NO 239
<211> LENGTH: 15
<212> TYPE: PRT
<213> ORGANISM: Zaire ebolavirus

<400> SEQUENCE: 239

Phe Ser Lys Ser Gln Leu Ser Leu Leu Cys Glu Thr His Leu Arg
1               5                   10                  15

<210> SEQ ID NO 240
<211> LENGTH: 15
<212> TYPE: PRT
<213> ORGANISM: Zaire ebolavirus

<400> SEQUENCE: 240

Leu Ser Leu Leu Cys Glu Thr His Leu Arg Arg Glu Gly Leu Gly
1               5                   10                  15
```

```
<210> SEQ ID NO 241
<211> LENGTH: 15
<212> TYPE: PRT
<213> ORGANISM: Zaire ebolavirus

<400> SEQUENCE: 241

Glu Thr His Leu Arg Arg Glu Gly Leu Gly Gln Asp Gln Ala Glu
1               5                   10                  15

<210> SEQ ID NO 242
<211> LENGTH: 15
<212> TYPE: PRT
<213> ORGANISM: Zaire ebolavirus

<400> SEQUENCE: 242

Arg Glu Gly Leu Gly Gln Asp Gln Ala Glu Pro Val Leu Glu Val
1               5                   10                  15

<210> SEQ ID NO 243
<211> LENGTH: 15
<212> TYPE: PRT
<213> ORGANISM: Zaire ebolavirus

<400> SEQUENCE: 243

Gly Thr Ala Phe His Gln Leu Val Gln Val Ile Cys Lys Leu Gly
1               5                   10                  15

<210> SEQ ID NO 244
<211> LENGTH: 15
<212> TYPE: PRT
<213> ORGANISM: Zaire ebolavirus

<400> SEQUENCE: 244

Ser Val Asn Gly Asp Thr Pro Ser Asn Pro Leu Arg Pro Ile Ala
1               5                   10                  15

<210> SEQ ID NO 245
<211> LENGTH: 15
<212> TYPE: PRT
<213> ORGANISM: Zaire ebolavirus

<400> SEQUENCE: 245

Thr Pro Ser Asn Pro Leu Arg Pro Ile Ala Asp Asp Thr Ile Asp
1               5                   10                  15

<210> SEQ ID NO 246
<211> LENGTH: 15
<212> TYPE: PRT
<213> ORGANISM: Zaire ebolavirus

<400> SEQUENCE: 246

Leu Arg Pro Ile Ala Asp Asp Thr Ile Asp His Ala Ser His Thr
1               5                   10                  15

<210> SEQ ID NO 247
<211> LENGTH: 15
<212> TYPE: PRT
<213> ORGANISM: Zaire ebolavirus

<400> SEQUENCE: 247

Asp Asp Thr Ile Asp His Ala Ser His Thr Pro Gly Ser Val Ser
1               5                   10                  15

<210> SEQ ID NO 248
<211> LENGTH: 15
```

-continued

<212> TYPE: PRT
<213> ORGANISM: Zaire ebolavirus

<400> SEQUENCE: 248

His Ala Ser His Thr Pro Gly Ser Val Ser Ser Ala Phe Ile Leu
1               5                   10                  15

<210> SEQ ID NO 249
<211> LENGTH: 15
<212> TYPE: PRT
<213> ORGANISM: Zaire ebolavirus

<400> SEQUENCE: 249

Pro Gly Ser Val Ser Ser Ala Phe Ile Leu Glu Ala Met Val Asn
1               5                   10                  15

<210> SEQ ID NO 250
<211> LENGTH: 15
<212> TYPE: PRT
<213> ORGANISM: Zaire ebolavirus

<400> SEQUENCE: 250

Ser Ala Phe Ile Leu Glu Ala Met Val Asn Val Ile Ser Gly Pro
1               5                   10                  15

<210> SEQ ID NO 251
<211> LENGTH: 15
<212> TYPE: PRT
<213> ORGANISM: Zaire ebolavirus

<400> SEQUENCE: 251

Glu Ala Met Val Asn Val Ile Ser Gly Pro Lys Val Leu Met Lys
1               5                   10                  15

<210> SEQ ID NO 252
<211> LENGTH: 15
<212> TYPE: PRT
<213> ORGANISM: Zaire ebolavirus

<400> SEQUENCE: 252

Gly Ala Leu Arg Pro Gly Ile Ser Phe His Pro Lys Leu Arg Pro
1               5                   10                  15

<210> SEQ ID NO 253
<211> LENGTH: 15
<212> TYPE: PRT
<213> ORGANISM: Zaire ebolavirus

<400> SEQUENCE: 253

Gly Ile Ser Phe His Pro Lys Leu Arg Pro Ile Leu Leu Pro Asn
1               5                   10                  15

<210> SEQ ID NO 254
<211> LENGTH: 15
<212> TYPE: PRT
<213> ORGANISM: Zaire ebolavirus

<400> SEQUENCE: 254

Pro Lys Leu Arg Pro Ile Leu Leu Pro Asn Lys Ser Gly Lys Lys
1               5                   10                  15

<210> SEQ ID NO 255
<211> LENGTH: 15
<212> TYPE: PRT
<213> ORGANISM: Zaire ebolavirus -continued

```
<400> SEQUENCE: 255

Ile Leu Leu Pro Asn Lys Ser Gly Lys Gly Asn Ser Ala Asp
1               5                   10                  15

<210> SEQ ID NO 256
<211> LENGTH: 15
<212> TYPE: PRT
<213> ORGANISM: Zaire ebolavirus

<400> SEQUENCE: 256

Lys Ser Gly Lys Gly Asn Ser Ala Asp Leu Thr Ser Pro Glu
1               5                   10                  15

<210> SEQ ID NO 257
<211> LENGTH: 15
<212> TYPE: PRT
<213> ORGANISM: Zaire ebolavirus

<400> SEQUENCE: 257

Gly Asn Ser Ala Asp Leu Thr Ser Pro Glu Lys Ile Gln Ala Ile
1               5                   10                  15

<210> SEQ ID NO 258
<211> LENGTH: 15
<212> TYPE: PRT
<213> ORGANISM: Zaire ebolavirus

<400> SEQUENCE: 258

Leu Thr Ser Pro Glu Lys Ile Gln Ala Ile Met Thr Ser Leu Gln
1               5                   10                  15

<210> SEQ ID NO 259
<211> LENGTH: 15
<212> TYPE: PRT
<213> ORGANISM: Zaire ebolavirus

<400> SEQUENCE: 259

Lys Ile Gln Ala Ile Met Thr Ser Leu Gln Asp Phe Lys Ile Val
1               5                   10                  15

<210> SEQ ID NO 260
<211> LENGTH: 15
<212> TYPE: PRT
<213> ORGANISM: Zaire ebolavirus

<400> SEQUENCE: 260

Met Arg Arg Val Ile Leu Pro Thr Ala Pro Pro Glu Tyr Met Glu
1               5                   10                  15

<210> SEQ ID NO 261
<211> LENGTH: 15
<212> TYPE: PRT
<213> ORGANISM: Zaire ebolavirus

<400> SEQUENCE: 261

Ser Val Asn Gly Asp Thr Pro Ser Asn Pro Leu Arg Pro Ile Ala
1               5                   10                  15

<210> SEQ ID NO 262
<211> LENGTH: 15
<212> TYPE: PRT
<213> ORGANISM: Zaire ebolavirus

<400> SEQUENCE: 262
```

Val Ile Ser Gly Pro Lys Val Leu Met Lys Gln Ile Pro Ile Trp
1               5                   10                  15

<210> SEQ ID NO 263
<211> LENGTH: 15
<212> TYPE: PRT
<213> ORGANISM: Zaire ebolavirus

<400> SEQUENCE: 263

Thr Ile Thr His Phe Gly Lys Ala Thr Asn Pro Leu Val Arg Val
1               5                   10                  15

<210> SEQ ID NO 264
<211> LENGTH: 15
<212> TYPE: PRT
<213> ORGANISM: Zaire ebolavirus

<400> SEQUENCE: 264

Phe Val Leu Pro Pro Val Gln Leu Pro Gln Tyr Phe Thr Phe Asp
1               5                   10                  15

<210> SEQ ID NO 265
<211> LENGTH: 15
<212> TYPE: PRT
<213> ORGANISM: Zaire ebolavirus

<400> SEQUENCE: 265

Gly Ala Leu Arg Pro Gly Ile Ser Phe His Pro Lys Leu Arg Pro
1               5                   10                  15

<210> SEQ ID NO 266
<211> LENGTH: 15
<212> TYPE: PRT
<213> ORGANISM: Zaire ebolavirus

<400> SEQUENCE: 266

Met Thr Ser Leu Gln Asp Phe Lys Ile Val Pro Ile Asp Pro Thr
1               5                   10                  15

<210> SEQ ID NO 267
<211> LENGTH: 15
<212> TYPE: PRT
<213> ORGANISM: Zaire ebolavirus

<400> SEQUENCE: 267

Gly Gln Pro Ile Ile Pro Val Leu Leu Pro Lys Tyr Ile Gly Leu
1               5                   10                  15

<210> SEQ ID NO 268
<211> LENGTH: 15
<212> TYPE: PRT
<213> ORGANISM: Zaire ebolavirus

<400> SEQUENCE: 268

Ala Ile Tyr Pro Val Arg Ser Asn Ser Thr Ile Ala Arg Gly Gly
1               5                   10                  15

<210> SEQ ID NO 269
<211> LENGTH: 15
<212> TYPE: PRT
<213> ORGANISM: Zaire ebolavirus

<400> SEQUENCE: 269

Asp Asp Thr Ile Asp His Ala Ser His Thr Pro Gly Ser Val Ser

```
                1               5                  10                  15
```

<210> SEQ ID NO 270
<211> LENGTH: 15
<212> TYPE: PRT
<213> ORGANISM: Zaire ebolavirus

<400> SEQUENCE: 270

```
Leu Pro Leu Gly Val Ala Asp Gln Lys Thr Tyr Ser Phe Asp Ser
1               5                  10                  15
```

<210> SEQ ID NO 271
<211> LENGTH: 15
<212> TYPE: PRT
<213> ORGANISM: Zaire ebolavirus

<400> SEQUENCE: 271

```
Asn Arg Leu Gly Pro Gly Ile Pro Asp His Pro Leu Arg Leu Leu
1               5                  10                  15
```

<210> SEQ ID NO 272
<211> LENGTH: 15
<212> TYPE: PRT
<213> ORGANISM: Zaire ebolavirus

<400> SEQUENCE: 272

```
Leu Thr Ala Leu Lys Leu Ile Thr Gln Pro Leu Pro Ala Ala Thr
1               5                  10                  15
```

<210> SEQ ID NO 273
<211> LENGTH: 15
<212> TYPE: PRT
<213> ORGANISM: Zaire ebolavirus

<400> SEQUENCE: 273

```
Ile Leu Leu Pro Asn Lys Ser Gly Lys Lys Gly Asn Ser Ala Asp
1               5                  10                  15
```

<210> SEQ ID NO 274
<211> LENGTH: 15
<212> TYPE: PRT
<213> ORGANISM: Zaire ebolavirus

<400> SEQUENCE: 274

```
Lys Asn Ile Met Gly Ile Glu Val Pro Glu Thr Leu Val His Lys
1               5                  10                  15
```

<210> SEQ ID NO 275
<211> LENGTH: 15
<212> TYPE: PRT
<213> ORGANISM: Zaire ebolavirus

<400> SEQUENCE: 275

```
Asp Pro Val Ala Pro Gly Asp Leu Thr Met Val Ile Thr Gln Asp
1               5                  10                  15
```

<210> SEQ ID NO 276
<211> LENGTH: 15
<212> TYPE: PRT
<213> ORGANISM: Zaire ebolavirus

<400> SEQUENCE: 276

```
Leu Trp Val Ile Ile Leu Phe Gln Arg Thr Phe Ser Ile Pro Leu
1               5                  10                  15
```

<210> SEQ ID NO 277
<211> LENGTH: 15
<212> TYPE: PRT
<213> ORGANISM: Zaire ebolavirus

<400> SEQUENCE: 277

Trp Gly Phe Arg Ser Gly Val Pro Pro Lys Val Val Asn Tyr Glu
1               5                   10                  15

<210> SEQ ID NO 278
<211> LENGTH: 15
<212> TYPE: PRT
<213> ORGANISM: Zaire ebolavirus

<400> SEQUENCE: 278

Phe Ala Phe His Lys Glu Gly Ala Phe Phe Leu Tyr Asp Arg Leu
1               5                   10                  15

<210> SEQ ID NO 279
<211> LENGTH: 15
<212> TYPE: PRT
<213> ORGANISM: Zaire ebolavirus

<400> SEQUENCE: 279

Thr Thr Ile Arg Tyr Gln Ala Thr Gly Phe Gly Thr Asn Glu Thr
1               5                   10                  15

<210> SEQ ID NO 280
<211> LENGTH: 15
<212> TYPE: PRT
<213> ORGANISM: Zaire ebolavirus

<400> SEQUENCE: 280

Ile Asp Thr Thr Ile Gly Glu Trp Ala Phe Trp Glu Thr Lys Lys
1               5                   10                  15

<210> SEQ ID NO 281
<211> LENGTH: 15
<212> TYPE: PRT
<213> ORGANISM: Zaire ebolavirus

<400> SEQUENCE: 281

Asn Ser Ser Ala Met Val Gln Val His Ser Gln Gly Arg Glu Ala
1               5                   10                  15

<210> SEQ ID NO 282
<211> LENGTH: 15
<212> TYPE: PRT
<213> ORGANISM: Zaire ebolavirus

<400> SEQUENCE: 282

Thr Asp Asn Asp Ser Thr Ala Ser Asp Thr Pro Ser Ala Thr Thr
1               5                   10                  15

<210> SEQ ID NO 283
<211> LENGTH: 15
<212> TYPE: PRT
<213> ORGANISM: Zaire ebolavirus

<400> SEQUENCE: 283

Ser Gly Lys Leu Gly Leu Ile Thr Asn Thr Ile Ala Gly Val Ala
1               5                   10                  15

<210> SEQ ID NO 284

```
<211> LENGTH: 15
<212> TYPE: PRT
<213> ORGANISM: Zaire ebolavirus

<400> SEQUENCE: 284

Gly Ile Tyr Thr Glu Gly Leu Met His Asn Gln Asp Gly Leu Ile
1               5                   10                  15

<210> SEQ ID NO 285
<211> LENGTH: 15
<212> TYPE: PRT
<213> ORGANISM: Zaire ebolavirus

<400> SEQUENCE: 285

Pro Asp Cys Cys Ile Glu Pro His Asp Trp Thr Lys Asn Ile Thr
1               5                   10                  15

<210> SEQ ID NO 286
<211> LENGTH: 15
<212> TYPE: PRT
<213> ORGANISM: Zaire ebolavirus

<400> SEQUENCE: 286

Asn Leu Thr Arg Lys Ile Arg Ser Glu Glu Leu Ser Phe Ser Ala
1               5                   10                  15

<210> SEQ ID NO 287
<211> LENGTH: 15
<212> TYPE: PRT
<213> ORGANISM: Zaire ebolavirus

<400> SEQUENCE: 287

Lys Ala Glu Asn Thr Asn Thr Ser Lys Gly Thr Asp Leu Leu Asp
1               5                   10                  15

<210> SEQ ID NO 288
<211> LENGTH: 15
<212> TYPE: PRT
<213> ORGANISM: Zaire ebolavirus

<400> SEQUENCE: 288

Leu Phe Gln Arg Thr Phe Ser Ile Pro Leu Gly Val Ile His Asn
1               5                   10                  15

<210> SEQ ID NO 289
<211> LENGTH: 15
<212> TYPE: PRT
<213> ORGANISM: Zaire ebolavirus

<400> SEQUENCE: 289

Gly Val Pro Pro Lys Val Val Asn Tyr Glu Ala Gly Glu Trp Ala
1               5                   10                  15

<210> SEQ ID NO 290
<211> LENGTH: 15
<212> TYPE: PRT
<213> ORGANISM: Zaire ebolavirus

<400> SEQUENCE: 290

Glu Gly Ala Phe Phe Leu Tyr Asp Arg Leu Ala Ser Thr Val Ile
1               5                   10                  15

<210> SEQ ID NO 291
<211> LENGTH: 15
<212> TYPE: PRT
```

-continued

<210> SEQ ID NO 291
<211> LENGTH: 15
<212> TYPE: PRT
<213> ORGANISM: Zaire ebolavirus

<400> SEQUENCE: 291

Gln Ala Thr Gly Phe Gly Thr Asn Glu Thr Glu Tyr Leu Phe Glu
1               5                   10                  15

<210> SEQ ID NO 292
<211> LENGTH: 15
<212> TYPE: PRT
<213> ORGANISM: Zaire ebolavirus

<400> SEQUENCE: 292

Gly Glu Trp Ala Phe Trp Glu Thr Lys Lys Asn Leu Thr Arg Lys
1               5                   10                  15

<210> SEQ ID NO 293
<211> LENGTH: 15
<212> TYPE: PRT
<213> ORGANISM: Zaire ebolavirus

<400> SEQUENCE: 293

Val Gln Val His Ser Gln Gly Arg Glu Ala Ala Val Ser His Leu
1               5                   10                  15

<210> SEQ ID NO 294
<211> LENGTH: 15
<212> TYPE: PRT
<213> ORGANISM: Zaire ebolavirus

<400> SEQUENCE: 294

Thr Ala Ser Asp Thr Pro Ser Ala Thr Thr Ala Ala Gly Pro Pro
1               5                   10                  15

<210> SEQ ID NO 295
<211> LENGTH: 15
<212> TYPE: PRT
<213> ORGANISM: Zaire ebolavirus

<400> SEQUENCE: 295

Leu Ile Thr Asn Thr Ile Ala Gly Val Ala Gly Leu Ile Thr Gly
1               5                   10                  15

<210> SEQ ID NO 296
<211> LENGTH: 15
<212> TYPE: PRT
<213> ORGANISM: Zaire ebolavirus

<400> SEQUENCE: 296

Gly Leu Met His Asn Gln Asp Gly Leu Ile Cys Gly Leu Arg Gln
1               5                   10                  15

<210> SEQ ID NO 297
<211> LENGTH: 15
<212> TYPE: PRT
<213> ORGANISM: Zaire ebolavirus

<400> SEQUENCE: 297

Glu Pro His Asp Trp Thr Lys Asn Ile Thr Asp Lys Ile Asp Gln
1               5                   10                  15

<210> SEQ ID NO 298
<211> LENGTH: 15
<212> TYPE: PRT
<213> ORGANISM: Zaire ebolavirus -continued

<400> SEQUENCE: 298

Ile Arg Ser Glu Glu Leu Ser Phe Ser Ala Val Ser Asn Arg Ala
1               5                   10                  15

<210> SEQ ID NO 299
<211> LENGTH: 15
<212> TYPE: PRT
<213> ORGANISM: Zaire ebolavirus

<400> SEQUENCE: 299

Asn Thr Ser Lys Gly Thr Asp Leu Leu Asp Pro Ala Thr Thr Thr
1               5                   10                  15

<210> SEQ ID NO 300
<211> LENGTH: 15
<212> TYPE: PRT
<213> ORGANISM: Zaire ebolavirus

<400> SEQUENCE: 300

Met Thr Arg Asn Leu Phe Pro His Leu Phe Gln Asn Pro Asn Ser
1               5                   10                  15

<210> SEQ ID NO 301
<211> LENGTH: 15
<212> TYPE: PRT
<213> ORGANISM: Zaire ebolavirus

<400> SEQUENCE: 301

Phe Pro His Leu Phe Gln Asn Pro Asn Ser Thr Ile Glu Ser Pro
1               5                   10                  15

<210> SEQ ID NO 302
<211> LENGTH: 15
<212> TYPE: PRT
<213> ORGANISM: Zaire ebolavirus

<400> SEQUENCE: 302

Gln Asn Pro Asn Ser Thr Ile Glu Ser Pro Leu Trp Ala Leu Arg
1               5                   10                  15

<210> SEQ ID NO 303
<211> LENGTH: 15
<212> TYPE: PRT
<213> ORGANISM: Zaire ebolavirus

<400> SEQUENCE: 303

Thr Ile Glu Ser Pro Leu Trp Ala Leu Arg Val Ile Leu Leu Ala
1               5                   10                  15

<210> SEQ ID NO 304
<211> LENGTH: 15
<212> TYPE: PRT
<213> ORGANISM: Zaire ebolavirus

<400> SEQUENCE: 304

Leu Trp Ala Leu Arg Val Ile Leu Leu Ala Gly Ile Gln Asp Gln
1               5                   10                  15

<210> SEQ ID NO 305
<211> LENGTH: 15
<212> TYPE: PRT
<213> ORGANISM: Zaire ebolavirus

<400> SEQUENCE: 305

-continued

Val Ile Leu Leu Ala Gly Ile Gln Asp Gln Leu Ile Asp Gln Ser
1               5                   10                  15

<210> SEQ ID NO 306
<211> LENGTH: 15
<212> TYPE: PRT
<213> ORGANISM: Zaire ebolavirus

<400> SEQUENCE: 306

Gly Ile Gln Asp Gln Leu Ile Asp Gln Ser Leu Ile Glu Pro Leu
1               5                   10                  15

<210> SEQ ID NO 307
<211> LENGTH: 15
<212> TYPE: PRT
<213> ORGANISM: Zaire ebolavirus

<400> SEQUENCE: 307

Leu Ile Asp Gln Ser Leu Ile Glu Pro Leu Ala Gly Ala Leu Gly
1               5                   10                  15

<210> SEQ ID NO 308
<211> LENGTH: 15
<212> TYPE: PRT
<213> ORGANISM: Zaire ebolavirus

<400> SEQUENCE: 308

Leu Ile Glu Pro Leu Ala Gly Ala Leu Gly Leu Ile Ser Asp Trp
1               5                   10                  15

<210> SEQ ID NO 309
<211> LENGTH: 15
<212> TYPE: PRT
<213> ORGANISM: Zaire ebolavirus

<400> SEQUENCE: 309

Ala Gly Ala Leu Gly Leu Ile Ser Asp Trp Leu Leu Thr Thr Asn
1               5                   10                  15

<210> SEQ ID NO 310
<211> LENGTH: 15
<212> TYPE: PRT
<213> ORGANISM: Zaire ebolavirus

<400> SEQUENCE: 310

Leu Ile Ser Asp Trp Leu Leu Thr Thr Asn Thr Asn His Phe Asn
1               5                   10                  15

<210> SEQ ID NO 311
<211> LENGTH: 15
<212> TYPE: PRT
<213> ORGANISM: Zaire ebolavirus

<400> SEQUENCE: 311

Leu Leu Thr Thr Asn Thr Asn His Phe Asn Met Arg Thr Gln Arg
1               5                   10                  15

<210> SEQ ID NO 312
<211> LENGTH: 15
<212> TYPE: PRT
<213> ORGANISM: Zaire ebolavirus

<400> SEQUENCE: 312

Thr Asn His Phe Asn Met Arg Thr Gln Arg Val Lys Glu Gln Leu
1               5                   10                  15

<210> SEQ ID NO 313
<211> LENGTH: 15
<212> TYPE: PRT
<213> ORGANISM: Zaire ebolavirus

<400> SEQUENCE: 313

Met Arg Thr Gln Arg Val Lys Glu Gln Leu Ser Leu Lys Met Leu
1               5                   10                  15

<210> SEQ ID NO 314
<211> LENGTH: 15
<212> TYPE: PRT
<213> ORGANISM: Zaire ebolavirus

<400> SEQUENCE: 314

Val Lys Glu Gln Leu Ser Leu Lys Met Leu Ser Leu Ile Arg Ser
1               5                   10                  15

<210> SEQ ID NO 315
<211> LENGTH: 15
<212> TYPE: PRT
<213> ORGANISM: Zaire ebolavirus

<400> SEQUENCE: 315

Ser Leu Lys Met Leu Ser Leu Ile Arg Ser Asn Ile Leu Lys Phe
1               5                   10                  15

<210> SEQ ID NO 316
<211> LENGTH: 15
<212> TYPE: PRT
<213> ORGANISM: Zaire ebolavirus

<400> SEQUENCE: 316

Ser Leu Ile Arg Ser Asn Ile Leu Lys Phe Ile Asn Lys Leu Asp
1               5                   10                  15

<210> SEQ ID NO 317
<211> LENGTH: 15
<212> TYPE: PRT
<213> ORGANISM: Zaire ebolavirus

<400> SEQUENCE: 317

Asn Ile Leu Lys Phe Ile Asn Lys Leu Asp Ala Leu His Val Val
1               5                   10                  15

<210> SEQ ID NO 318
<211> LENGTH: 15
<212> TYPE: PRT
<213> ORGANISM: Zaire ebolavirus

<400> SEQUENCE: 318

Ile Asn Lys Leu Asp Ala Leu His Val Val Asn Tyr Asn Gly Leu
1               5                   10                  15

<210> SEQ ID NO 319
<211> LENGTH: 15
<212> TYPE: PRT
<213> ORGANISM: Zaire ebolavirus

<400> SEQUENCE: 319

Ala Leu His Val Val Asn Tyr Asn Gly Leu Leu Ser Ser Ile Glu
1               5                   10                  15

```
<210> SEQ ID NO 320
<211> LENGTH: 15
<212> TYPE: PRT
<213> ORGANISM: Zaire ebolavirus

<400> SEQUENCE: 320

Asn Tyr Asn Gly Leu Leu Ser Ser Ile Glu Ile Gly Thr Gln Asn
1               5                   10                  15

<210> SEQ ID NO 321
<211> LENGTH: 15
<212> TYPE: PRT
<213> ORGANISM: Zaire ebolavirus

<400> SEQUENCE: 321

Val Val Leu Ser Asp Leu Cys Asn Phe Leu Val Ser Gln Thr Ile
1               5                   10                  15

<210> SEQ ID NO 322
<211> LENGTH: 15
<212> TYPE: PRT
<213> ORGANISM: Zaire ebolavirus

<400> SEQUENCE: 322

Leu Leu His Arg Leu Lys Thr Asn Asp Phe Ala Pro Ala Trp Ser
1               5                   10                  15

<210> SEQ ID NO 323
<211> LENGTH: 15
<212> TYPE: PRT
<213> ORGANISM: Zaire ebolavirus

<400> SEQUENCE: 323

Leu Trp Ala Leu Arg Val Ile Leu Leu Ala Gly Ile Gln Asp Gln
1               5                   10                  15

<210> SEQ ID NO 324
<211> LENGTH: 15
<212> TYPE: PRT
<213> ORGANISM: Zaire ebolavirus

<400> SEQUENCE: 324

Leu Leu Thr Thr Asn Thr Asn His Phe Asn Met Arg Thr Gln Arg
1               5                   10                  15

<210> SEQ ID NO 325
<211> LENGTH: 15
<212> TYPE: PRT
<213> ORGANISM: Zaire ebolavirus

<400> SEQUENCE: 325

Ile Asn Lys Leu Asp Ala Leu His Val Val Asn Tyr Asn Gly Leu
1               5                   10                  15

<210> SEQ ID NO 326
<211> LENGTH: 15
<212> TYPE: PRT
<213> ORGANISM: Zaire ebolavirus

<400> SEQUENCE: 326

Gly Phe Leu Val Glu Leu Gln Glu Pro Asp Lys Ser Ala Met Asn
1               5                   10                  15

<210> SEQ ID NO 327
<211> LENGTH: 15
```

```
<212> TYPE: PRT
<213> ORGANISM: Zaire ebolavirus

<400> SEQUENCE: 327

Thr Gln Gly Ser Ser Thr Arg Met Gln Ser Leu Ile Leu Glu Phe
1               5                   10                  15

<210> SEQ ID NO 328
<211> LENGTH: 15
<212> TYPE: PRT
<213> ORGANISM: Zaire ebolavirus

<400> SEQUENCE: 328

Leu Cys Asn Phe Leu Val Ser Gln Thr Ile Gln Gly Trp Lys Val
1               5                   10                  15

<210> SEQ ID NO 329
<211> LENGTH: 15
<212> TYPE: PRT
<213> ORGANISM: Zaire ebolavirus

<400> SEQUENCE: 329

Lys Thr Asn Asp Phe Ala Pro Ala Trp Ser Met Thr Arg Asn Leu
1               5                   10                  15

<210> SEQ ID NO 330
<211> LENGTH: 15
<212> TYPE: PRT
<213> ORGANISM: Zaire ebolavirus

<400> SEQUENCE: 330

Val Ile Leu Leu Ala Gly Ile Gln Asp Gln Leu Ile Asp Gln Ser
1               5                   10                  15

<210> SEQ ID NO 331
<211> LENGTH: 15
<212> TYPE: PRT
<213> ORGANISM: Zaire ebolavirus

<400> SEQUENCE: 331

Thr Asn His Phe Asn Met Arg Thr Gln Arg Val Lys Glu Gln Leu
1               5                   10                  15

<210> SEQ ID NO 332
<211> LENGTH: 15
<212> TYPE: PRT
<213> ORGANISM: Zaire ebolavirus

<400> SEQUENCE: 332

Ala Leu His Val Val Asn Tyr Asn Gly Leu Leu Ser Ser Glu Ile
1               5                   10                  15

<210> SEQ ID NO 333
<211> LENGTH: 15
<212> TYPE: PRT
<213> ORGANISM: Zaire ebolavirus

<400> SEQUENCE: 333

Leu Gln Glu Pro Asp Lys Ser Ala Met Asn Arg Met Lys Pro Gly
1               5                   10                  15

<210> SEQ ID NO 334
<211> LENGTH: 15
<212> TYPE: PRT
<213> ORGANISM: Zaire ebolavirus
```

```
<400> SEQUENCE: 334

Thr Arg Met Gln Ser Leu Ile Leu Glu Phe Asn Ser Ser Leu Ala
1               5                   10                  15

<210> SEQ ID NO 335
<211> LENGTH: 16
<212> TYPE: PRT
<213> ORGANISM: Zaire ebolavirus

<400> SEQUENCE: 335

His Ser Arg Asp Gly His Asp His His Val Arg Ala Arg Ser Ser
1               5                   10                  15

<210> SEQ ID NO 336
<211> LENGTH: 15
<212> TYPE: PRT
<213> ORGANISM: Zaire ebolavirus

<400> SEQUENCE: 336

Lys Lys Arg Val Glu Pro Leu Thr Val Pro Ala Pro Lys Asp
1               5                   10                  15

<210> SEQ ID NO 337
<211> LENGTH: 15
<212> TYPE: PRT
<213> ORGANISM: Zaire ebolavirus

<400> SEQUENCE: 337

Thr Asp Arg Glu Leu Leu Leu Leu Ile Ala Arg Lys Thr Cys Gly
1               5                   10                  15

<210> SEQ ID NO 338
<211> LENGTH: 15
<212> TYPE: PRT
<213> ORGANISM: Zaire ebolavirus

<400> SEQUENCE: 338

Gln Glu Glu Gly Pro Lys Ile Thr Leu Leu Thr Leu Ile Lys Thr
1               5                   10                  15

<210> SEQ ID NO 339
<211> LENGTH: 15
<212> TYPE: PRT
<213> ORGANISM: Zaire ebolavirus

<400> SEQUENCE: 339

Val Met Thr Arg Lys Phe Ser Lys Ser Gln Leu Ser Leu Leu Cys
1               5                   10                  15

<210> SEQ ID NO 340
<211> LENGTH: 15
<212> TYPE: PRT
<213> ORGANISM: Zaire ebolavirus

<400> SEQUENCE: 340

Ser Asp Lys Gly Gly Ser Phe Glu Ala Ala Leu Trp Gln Gln Trp
1               5                   10                  15

<210> SEQ ID NO 341
<211> LENGTH: 15
<212> TYPE: PRT
<213> ORGANISM: Zaire ebolavirus

<400> SEQUENCE: 341
```

-continued

```
Val Val Val Ser Gly Leu Arg Thr Leu Val Pro Gln Ser Asp Asn
1               5                  10                  15

<210> SEQ ID NO 342
<211> LENGTH: 14
<212> TYPE: PRT
<213> ORGANISM: Zaire ebolavirus

<400> SEQUENCE: 342

His Asp His His Val Arg Ala Arg Ser Ser Arg Glu Asn Tyr
1               5                  10

<210> SEQ ID NO 343
<211> LENGTH: 15
<212> TYPE: PRT
<213> ORGANISM: Zaire ebolavirus

<400> SEQUENCE: 343

Pro Leu Thr Val Pro Pro Ala Pro Lys Asp Ile Cys Pro Thr Leu
1               5                  10                  15

<210> SEQ ID NO 344
<211> LENGTH: 15
<212> TYPE: PRT
<213> ORGANISM: Zaire ebolavirus

<400> SEQUENCE: 344

Leu Leu Leu Ile Ala Arg Lys Thr Cys Gly Ser Val Glu Gln Gln
1               5                  10                  15

<210> SEQ ID NO 345
<211> LENGTH: 15
<212> TYPE: PRT
<213> ORGANISM: Zaire ebolavirus

<400> SEQUENCE: 345

Lys Ile Thr Leu Leu Thr Leu Ile Lys Thr Ala Glu His Trp Ala
1               5                  10                  15

<210> SEQ ID NO 346
<211> LENGTH: 15
<212> TYPE: PRT
<213> ORGANISM: Zaire ebolavirus

<400> SEQUENCE: 346

Phe Ser Lys Ser Gln Leu Ser Leu Leu Cys Glu Thr His Leu Arg
1               5                  10                  15

<210> SEQ ID NO 347
<211> LENGTH: 15
<212> TYPE: PRT
<213> ORGANISM: Zaire ebolavirus

<400> SEQUENCE: 347

Ser Phe Glu Ala Ala Leu Trp Gln Gln Trp Asp Arg Gln Ser Leu
1               5                  10                  15

<210> SEQ ID NO 348
<211> LENGTH: 15
<212> TYPE: PRT
<213> ORGANISM: Zaire ebolavirus

<400> SEQUENCE: 348

Leu Arg Thr Leu Val Pro Gln Ser Asp Asn Glu Glu Ala Ser Thr
```

```
                  1               5              10              15
```

<210> SEQ ID NO 349
<211> LENGTH: 15
<212> TYPE: PRT
<213> ORGANISM: Zaire ebolavirus

<400> SEQUENCE: 349

```
Leu Pro Thr Ala Pro Pro Glu Tyr Met Glu Ala Ile Tyr Pro Val
1               5                   10                  15
```

<210> SEQ ID NO 350
<211> LENGTH: 15
<212> TYPE: PRT
<213> ORGANISM: Zaire ebolavirus

<400> SEQUENCE: 350

```
Thr Pro Ser Asn Pro Leu Arg Pro Ile Ala Asp Asp Thr Ile Asp
1               5                   10                  15
```

<210> SEQ ID NO 351
<211> LENGTH: 15
<212> TYPE: PRT
<213> ORGANISM: Zaire ebolavirus

<400> SEQUENCE: 351

```
Lys Val Leu Met Lys Gln Ile Pro Ile Trp Leu Pro Leu Gly Val
1               5                   10                  15
```

<210> SEQ ID NO 352
<211> LENGTH: 15
<212> TYPE: PRT
<213> ORGANISM: Zaire ebolavirus

<400> SEQUENCE: 352

```
Gly Lys Ala Thr Asn Pro Leu Val Arg Val Asn Arg Leu Gly Pro
1               5                   10                  15
```

<210> SEQ ID NO 353
<211> LENGTH: 15
<212> TYPE: PRT
<213> ORGANISM: Zaire ebolavirus

<400> SEQUENCE: 353

```
Val Gln Leu Pro Gln Tyr Phe Thr Phe Asp Leu Thr Ala Leu Lys
1               5                   10                  15
```

<210> SEQ ID NO 354
<211> LENGTH: 15
<212> TYPE: PRT
<213> ORGANISM: Zaire ebolavirus

<400> SEQUENCE: 354

```
Gly Ile Ser Phe His Pro Lys Leu Arg Pro Ile Leu Leu Pro Asn
1               5                   10                  15
```

<210> SEQ ID NO 355
<211> LENGTH: 15
<212> TYPE: PRT
<213> ORGANISM: Zaire ebolavirus

<400> SEQUENCE: 355

```
Asp Phe Lys Ile Val Pro Ile Asp Pro Thr Lys Asn Ile Met Gly
1               5                   10                  15
```

-continued

<210> SEQ ID NO 356
<211> LENGTH: 15
<212> TYPE: PRT
<213> ORGANISM: Zaire ebolavirus

<400> SEQUENCE: 356

Pro Val Leu Leu Pro Lys Tyr Ile Gly Leu Asp Pro Val Ala Pro
1               5                   10                  15

<210> SEQ ID NO 357
<211> LENGTH: 15
<212> TYPE: PRT
<213> ORGANISM: Zaire ebolavirus

<400> SEQUENCE: 357

Ile Ala Arg Gly Gly Asn Ser Asn Thr Gly Phe Leu Thr Pro Glu
1               5                   10                  15

<210> SEQ ID NO 358
<211> LENGTH: 15
<212> TYPE: PRT
<213> ORGANISM: Zaire ebolavirus

<400> SEQUENCE: 358

Pro Gly Ser Val Ser Ser Ala Phe Ile Leu Glu Ala Met Val Asn
1               5                   10                  15

<210> SEQ ID NO 359
<211> LENGTH: 15
<212> TYPE: PRT
<213> ORGANISM: Zaire ebolavirus

<400> SEQUENCE: 359

Tyr Ser Phe Asp Ser Thr Thr Ala Ala Ile Met Leu Ala Ser Tyr
1               5                   10                  15

<210> SEQ ID NO 360
<211> LENGTH: 15
<212> TYPE: PRT
<213> ORGANISM: Zaire ebolavirus

<400> SEQUENCE: 360

Pro Leu Arg Leu Leu Arg Ile Gly Asn Gln Ala Phe Leu Gln Glu
1               5                   10                  15

<210> SEQ ID NO 361
<211> LENGTH: 15
<212> TYPE: PRT
<213> ORGANISM: Zaire ebolavirus

<400> SEQUENCE: 361

Leu Pro Ala Ala Thr Trp Thr Asp Asp Thr Pro Thr Gly Ser Asn
1               5                   10                  15

<210> SEQ ID NO 362
<211> LENGTH: 15
<212> TYPE: PRT
<213> ORGANISM: Zaire ebolavirus

<400> SEQUENCE: 362

Gly Asn Ser Ala Asp Leu Thr Ser Pro Glu Lys Ile Gln Ala Ile
1               5                   10                  15

<210> SEQ ID NO 363

```
<211> LENGTH: 15
<212> TYPE: PRT
<213> ORGANISM: Zaire ebolavirus

<400> SEQUENCE: 363

Thr Leu Val His Lys Leu Thr Gly Lys Lys Val Thr Ser Lys Asn
1               5                   10                  15

<210> SEQ ID NO 364
<211> LENGTH: 15
<212> TYPE: PRT
<213> ORGANISM: Zaire ebolavirus

<400> SEQUENCE: 364

Val Ile Thr Gln Asp Cys Asp Thr Cys His Ser Pro Ala Ser Leu
1               5                   10                  15

<210> SEQ ID NO 365
<211> LENGTH: 15
<212> TYPE: PRT
<213> ORGANISM: Zaire ebolavirus

<400> SEQUENCE: 365

Met Gly Val Thr Gly Ile Leu Gln Leu Pro Arg Asp Arg Phe Lys
1               5                   10                  15

<210> SEQ ID NO 366
<211> LENGTH: 15
<212> TYPE: PRT
<213> ORGANISM: Zaire ebolavirus

<400> SEQUENCE: 366

Val Gly Leu Asn Leu Glu Gly Asn Gly Val Ala Thr Asp Val Pro
1               5                   10                  15

<210> SEQ ID NO 367
<211> LENGTH: 15
<212> TYPE: PRT
<213> ORGANISM: Zaire ebolavirus

<400> SEQUENCE: 367

Gly Phe Pro Arg Cys Arg Tyr Val His Lys Val Ser Gly Thr Gly
1               5                   10                  15

<210> SEQ ID NO 368
<211> LENGTH: 15
<212> TYPE: PRT
<213> ORGANISM: Zaire ebolavirus

<400> SEQUENCE: 368

Ser His Pro Leu Arg Glu Pro Val Asn Ala Thr Glu Asp Pro Ser
1               5                   10                  15

<210> SEQ ID NO 369
<211> LENGTH: 15
<212> TYPE: PRT
<213> ORGANISM: Zaire ebolavirus

<400> SEQUENCE: 369

Tyr Thr Ser Gly Lys Arg Ser Asn Thr Thr Gly Lys Leu Ile Trp
1               5                   10                  15

<210> SEQ ID NO 370
<211> LENGTH: 15
<212> TYPE: PRT
```

-continued

<213> ORGANISM: Zaire ebolavirus

<400> SEQUENCE: 370

Thr Ser Ser Asp Pro Gly Thr Asn Thr Thr Glu Asp His Lys
1               5                   10                  15

<210> SEQ ID NO 371
<211> LENGTH: 15
<212> TYPE: PRT
<213> ORGANISM: Zaire ebolavirus

<400> SEQUENCE: 371

Thr Pro Val Tyr Lys Leu Asp Ile Ser Glu Ala Thr Gln Val Glu
1               5                   10                  15

<210> SEQ ID NO 372
<211> LENGTH: 15
<212> TYPE: PRT
<213> ORGANISM: Zaire ebolavirus

<400> SEQUENCE: 372

Ser Glu Thr Ala Gly Asn Asn Asn Thr His His Gln Asp Thr Gly
1               5                   10                  15

<210> SEQ ID NO 373
<211> LENGTH: 15
<212> TYPE: PRT
<213> ORGANISM: Zaire ebolavirus

<400> SEQUENCE: 373

Gln Asp Glu Gly Ala Ala Ile Gly Leu Ala Trp Ile Pro Tyr Phe
1               5                   10                  15

<210> SEQ ID NO 374
<211> LENGTH: 15
<212> TYPE: PRT
<213> ORGANISM: Zaire ebolavirus

<400> SEQUENCE: 374

Asn Arg Lys Ala Ile Asp Phe Leu Leu Gln Arg Trp Gly Gly Thr
1               5                   10                  15

<210> SEQ ID NO 375
<211> LENGTH: 15
<212> TYPE: PRT
<213> ORGANISM: Zaire ebolavirus

<400> SEQUENCE: 375

Trp Ile Pro Ala Gly Ile Gly Val Thr Gly Val Ile Ile Ala Val
1               5                   10                  15

<210> SEQ ID NO 376
<211> LENGTH: 15
<212> TYPE: PRT
<213> ORGANISM: Zaire ebolavirus

<400> SEQUENCE: 376

Thr Asp Asn Asp Ser Thr Ala Ser Asp Thr Pro Pro Ala Thr Thr
1               5                   10                  15

<210> SEQ ID NO 377
<211> LENGTH: 15
<212> TYPE: PRT
<213> ORGANISM: Zaire ebolavirus

<400> SEQUENCE: 377

Gly Leu Met His Asn Gln Asp Gly Leu Phe Cys Gly Leu Arg Gln
1               5                   10                  15

<210> SEQ ID NO 378
<211> LENGTH: 15
<212> TYPE: PRT
<213> ORGANISM: Zaire ebolavirus

<400> SEQUENCE: 378

Pro Lys Asp Ser Arg Leu Ala Asn Pro Thr Ala Asp Asp Phe Gln
1               5                   10                  15

<210> SEQ ID NO 379
<211> LENGTH: 15
<212> TYPE: PRT
<213> ORGANISM: Zaire ebolavirus

<400> SEQUENCE: 379

Leu Ala Asn Pro Thr Ala Asp Asp Phe Gln Gln Glu Glu Gly Pro
1               5                   10                  15

<210> SEQ ID NO 380
<211> LENGTH: 15
<212> TYPE: PRT
<213> ORGANISM: Zaire ebolavirus

<400> SEQUENCE: 380

Ala Asp Asp Phe Gln Gln Glu Glu Gly Pro Lys Ile Thr Leu Leu
1               5                   10                  15

<210> SEQ ID NO 381
<211> LENGTH: 15
<212> TYPE: PRT
<213> ORGANISM: Zaire ebolavirus

<400> SEQUENCE: 381

Gln Glu Glu Gly Pro Lys Ile Thr Leu Leu Thr Leu Ile Lys Thr
1               5                   10                  15

<210> SEQ ID NO 382
<211> LENGTH: 15
<212> TYPE: PRT
<213> ORGANISM: Zaire ebolavirus

<400> SEQUENCE: 382

Lys Ile Thr Leu Leu Thr Leu Ile Lys Thr Ala Glu His Trp Ala
1               5                   10                  15

<210> SEQ ID NO 383
<211> LENGTH: 15
<212> TYPE: PRT
<213> ORGANISM: Zaire ebolavirus

<400> SEQUENCE: 383

Thr Leu Ile Lys Thr Ala Glu His Trp Ala Arg Gln Asp Ile Arg
1               5                   10                  15

<210> SEQ ID NO 384
<211> LENGTH: 15
<212> TYPE: PRT
<213> ORGANISM: Zaire ebolavirus

<400> SEQUENCE: 384

```
Ala Glu His Trp Ala Arg Gln Asp Ile Arg Thr Ile Glu Asp Ser
1               5                   10                  15

<210> SEQ ID NO 385
<211> LENGTH: 15
<212> TYPE: PRT
<213> ORGANISM: Zaire ebolavirus

<400> SEQUENCE: 385

Arg Gln Asp Ile Arg Thr Ile Glu Asp Ser Lys Leu Arg Ala Leu
1               5                   10                  15

<210> SEQ ID NO 386
<211> LENGTH: 15
<212> TYPE: PRT
<213> ORGANISM: Zaire ebolavirus

<400> SEQUENCE: 386

Ser Asp Ile Phe Cys Asp Ile Glu Asn Asn Pro Gly Leu Cys Tyr
1               5                   10                  15

<210> SEQ ID NO 387
<211> LENGTH: 15
<212> TYPE: PRT
<213> ORGANISM: Zaire ebolavirus

<400> SEQUENCE: 387

Asp Ile Glu Asn Asn Pro Gly Leu Cys Tyr Ala Ser Gln Met Gln
1               5                   10                  15

<210> SEQ ID NO 388
<211> LENGTH: 15
<212> TYPE: PRT
<213> ORGANISM: Zaire ebolavirus

<400> SEQUENCE: 388

Pro Gly Leu Cys Tyr Ala Ser Gln Met Gln Gln Thr Lys Pro Asn
1               5                   10                  15

<210> SEQ ID NO 389
<211> LENGTH: 15
<212> TYPE: PRT
<213> ORGANISM: Zaire ebolavirus

<400> SEQUENCE: 389

Ala Ser Gln Met Gln Gln Thr Lys Pro Asn Pro Lys Thr Arg Asn
1               5                   10                  15

<210> SEQ ID NO 390
<211> LENGTH: 15
<212> TYPE: PRT
<213> ORGANISM: Zaire ebolavirus

<400> SEQUENCE: 390

Gln Thr Lys Pro Asn Pro Lys Thr Arg Asn Ser Gln Thr Gln Thr
1               5                   10                  15

<210> SEQ ID NO 391
<211> LENGTH: 15
<212> TYPE: PRT
<213> ORGANISM: Zaire ebolavirus

<400> SEQUENCE: 391

Pro Lys Thr Arg Asn Ser Gln Thr Gln Thr Asp Pro Ile Cys Asn
1               5                   10                  15
```

<210> SEQ ID NO 392
<211> LENGTH: 15
<212> TYPE: PRT
<213> ORGANISM: Zaire ebolavirus

<400> SEQUENCE: 392

Ser Gln Thr Gln Thr Asp Pro Ile Cys Asn His Ser Phe Glu Glu
1               5                   10                  15

<210> SEQ ID NO 393
<211> LENGTH: 15
<212> TYPE: PRT
<213> ORGANISM: Zaire ebolavirus

<400> SEQUENCE: 393

Asp Pro Ile Cys Asn His Ser Phe Glu Glu Val Val Gln Thr Leu
1               5                   10                  15

<210> SEQ ID NO 394
<211> LENGTH: 15
<212> TYPE: PRT
<213> ORGANISM: Zaire ebolavirus

<400> SEQUENCE: 394

His Ser Phe Glu Glu Val Val Gln Thr Leu Ala Ser Leu Ala Thr
1               5                   10                  15

<210> SEQ ID NO 395
<211> LENGTH: 15
<212> TYPE: PRT
<213> ORGANISM: Zaire ebolavirus

<400> SEQUENCE: 395

Val Val Gln Thr Leu Ala Ser Leu Ala Thr Val Val Gln Gln Gln
1               5                   10                  15

<210> SEQ ID NO 396
<211> LENGTH: 15
<212> TYPE: PRT
<213> ORGANISM: Zaire ebolavirus

<400> SEQUENCE: 396

Ala Ser Leu Ala Thr Val Val Gln Gln Gln Thr Ile Ala Ser Glu
1               5                   10                  15

<210> SEQ ID NO 397
<211> LENGTH: 15
<212> TYPE: PRT
<213> ORGANISM: Zaire ebolavirus

<400> SEQUENCE: 397

Val Val Gln Gln Gln Thr Ile Ala Ser Glu Ser Leu Glu Gln Arg
1               5                   10                  15

<210> SEQ ID NO 398
<211> LENGTH: 15
<212> TYPE: PRT
<213> ORGANISM: Zaire ebolavirus

<400> SEQUENCE: 398

Thr Ile Ala Ser Glu Ser Leu Glu Gln Arg Ile Thr Ser Leu Glu
1               5                   10                  15

```
<210> SEQ ID NO 399
<211> LENGTH: 15
<212> TYPE: PRT
<213> ORGANISM: Zaire ebolavirus

<400> SEQUENCE: 399

Ser Leu Glu Gln Arg Ile Thr Ser Leu Glu Asn Gly Leu Lys Pro
1               5                   10                  15

<210> SEQ ID NO 400
<211> LENGTH: 15
<212> TYPE: PRT
<213> ORGANISM: Zaire ebolavirus

<400> SEQUENCE: 400

Ile Thr Ser Leu Glu Asn Gly Leu Lys Pro Val Tyr Asp Met Ala
1               5                   10                  15

<210> SEQ ID NO 401
<211> LENGTH: 15
<212> TYPE: PRT
<213> ORGANISM: Zaire ebolavirus

<400> SEQUENCE: 401

Asn Gly Leu Lys Pro Val Tyr Asp Met Ala Lys Thr Ile Ser Ser
1               5                   10                  15

<210> SEQ ID NO 402
<211> LENGTH: 15
<212> TYPE: PRT
<213> ORGANISM: Zaire ebolavirus

<400> SEQUENCE: 402

Asn Asn Leu Asn Ser Thr Thr Ser Leu Thr Glu Glu Asn Phe Gly
1               5                   10                  15

<210> SEQ ID NO 403
<211> LENGTH: 15
<212> TYPE: PRT
<213> ORGANISM: Zaire ebolavirus

<400> SEQUENCE: 403

Thr Thr Ser Leu Thr Glu Glu Asn Phe Gly Lys Pro Asp Ile Ser
1               5                   10                  15

<210> SEQ ID NO 404
<211> LENGTH: 15
<212> TYPE: PRT
<213> ORGANISM: Zaire ebolavirus

<400> SEQUENCE: 404

Glu Glu Asn Phe Gly Lys Pro Asp Ile Ser Ala Lys Asp Leu Arg
1               5                   10                  15

<210> SEQ ID NO 405
<211> LENGTH: 15
<212> TYPE: PRT
<213> ORGANISM: Zaire ebolavirus

<400> SEQUENCE: 405

Lys Pro Asp Ile Ser Ala Lys Asp Leu Arg Asn Ile Met Tyr Asp
1               5                   10                  15

<210> SEQ ID NO 406
<211> LENGTH: 15
```

```
<212> TYPE: PRT
<213> ORGANISM: Zaire ebolavirus

<400> SEQUENCE: 406

Ala Lys Asp Leu Arg Asn Ile Met Tyr Asp His Leu Pro Gly Phe
1               5                   10                  15

<210> SEQ ID NO 407
<211> LENGTH: 15
<212> TYPE: PRT
<213> ORGANISM: Zaire ebolavirus

<400> SEQUENCE: 407

Asn Ile Met Tyr Asp His Leu Pro Gly Phe Gly Thr Ala Phe His
1               5                   10                  15

<210> SEQ ID NO 408
<211> LENGTH: 15
<212> TYPE: PRT
<213> ORGANISM: Zaire ebolavirus

<400> SEQUENCE: 408

His Leu Pro Gly Phe Gly Thr Ala Phe His Gln Leu Val Gln Val
1               5                   10                  15

<210> SEQ ID NO 409
<211> LENGTH: 15
<212> TYPE: PRT
<213> ORGANISM: Zaire ebolavirus

<400> SEQUENCE: 409

Gly Thr Ala Phe His Gln Leu Val Gln Val Ile Cys Lys Leu Gly
1               5                   10                  15

<210> SEQ ID NO 410
<211> LENGTH: 15
<212> TYPE: PRT
<213> ORGANISM: Zaire ebolavirus

<400> SEQUENCE: 410

Thr Ala Ala Thr Thr Gln Asn Asp Arg Met Pro Gly Pro Glu Leu
1               5                   10                  15

<210> SEQ ID NO 411
<211> LENGTH: 15
<212> TYPE: PRT
<213> ORGANISM: Zaire ebolavirus

<400> SEQUENCE: 411

Pro Gly Leu Cys Tyr Ala Ser Gln Met Gln Gln Thr Lys Pro Asn
1               5                   10                  15

<210> SEQ ID NO 412
<211> LENGTH: 15
<212> TYPE: PRT
<213> ORGANISM: Zaire ebolavirus

<400> SEQUENCE: 412

Ala Ser Leu Ala Thr Val Val Gln Gln Gln Thr Ile Ala Ser Glu
1               5                   10                  15

<210> SEQ ID NO 413
<211> LENGTH: 15
<212> TYPE: PRT
<213> ORGANISM: Zaire ebolavirus
```

```
<400> SEQUENCE: 413

Leu Asn Arg Val Cys Ala Glu Met Val Ala Lys Tyr Asp Leu Leu
1               5                   10                  15

<210> SEQ ID NO 414
<211> LENGTH: 15
<212> TYPE: PRT
<213> ORGANISM: Zaire ebolavirus

<400> SEQUENCE: 414

Pro Gly Pro Ser Leu Tyr Glu Glu Ser Ala Ile Arg Gly Lys Ile
1               5                   10                  15

<210> SEQ ID NO 415
<211> LENGTH: 15
<212> TYPE: PRT
<213> ORGANISM: Zaire ebolavirus

<400> SEQUENCE: 415

Glu Glu Asn Phe Gly Lys Pro Asp Ile Ser Ala Lys Asp Leu Arg
1               5                   10                  15

<210> SEQ ID NO 416
<211> LENGTH: 15
<212> TYPE: PRT
<213> ORGANISM: Zaire ebolavirus

<400> SEQUENCE: 416

Lys Asp Ser Asn Ser Leu Asp Ile Ile His Ala Glu Phe Gln Ala
1               5                   10                  15

<210> SEQ ID NO 417
<211> LENGTH: 15
<212> TYPE: PRT
<213> ORGANISM: Zaire ebolavirus

<400> SEQUENCE: 417

Ala Pro Pro Val Ile His Ile Arg Ser Arg Gly Asp Ile Pro Arg
1               5                   10                  15

<210> SEQ ID NO 418
<211> LENGTH: 15
<212> TYPE: PRT
<213> ORGANISM: Zaire ebolavirus

<400> SEQUENCE: 418

Ser Asp Val Asp Lys Leu Val Cys Arg Asp Lys Leu Ser Ser Thr
1               5                   10                  15

<210> SEQ ID NO 419
<211> LENGTH: 15
<212> TYPE: PRT
<213> ORGANISM: Zaire ebolavirus

<400> SEQUENCE: 419

Leu Glu Ile Lys Lys Pro Asp Gly Ser Glu Cys Leu Pro Ala Ala
1               5                   10                  15

<210> SEQ ID NO 420
<211> LENGTH: 15
<212> TYPE: PRT
<213> ORGANISM: Zaire ebolavirus

<400> SEQUENCE: 420
```

```
Phe Ala Glu Gly Val Val Ala Phe Leu Ile Leu Pro Gln Ala Lys
1               5                   10                  15

<210> SEQ ID NO 421
<211> LENGTH: 15
<212> TYPE: PRT
<213> ORGANISM: Zaire ebolavirus

<400> SEQUENCE: 421

Tyr Val Gln Leu Glu Ser Arg Phe Thr Pro Gln Phe Leu Leu Gln
1               5                   10                  15

<210> SEQ ID NO 422
<211> LENGTH: 15
<212> TYPE: PRT
<213> ORGANISM: Zaire ebolavirus

<400> SEQUENCE: 422

Leu Ser Phe Thr Val Val Ser Asn Gly Ala Lys Asn Ile Ser Gly
1               5                   10                  15

<210> SEQ ID NO 423
<211> LENGTH: 15
<212> TYPE: PRT
<213> ORGANISM: Zaire ebolavirus

<400> SEQUENCE: 423

Ile Ser Thr Ser Pro Gln Ser Leu Thr Thr Lys Pro Gly Pro Asp
1               5                   10                  15

<210> SEQ ID NO 424
<211> LENGTH: 15
<212> TYPE: PRT
<213> ORGANISM: Zaire ebolavirus

<400> SEQUENCE: 424

Asn Thr Ser Lys Ser Thr Asp Phe Leu Asp Pro Ala Thr Thr Thr
1               5                   10                  15

<210> SEQ ID NO 425
<211> LENGTH: 15
<212> TYPE: PRT
<213> ORGANISM: Zaire ebolavirus

<400> SEQUENCE: 425

Arg Glu Ala Ile Val Asn Ala Gln Pro Lys Cys Asn Pro Asn Leu
1               5                   10                  15

<210> SEQ ID NO 426
<211> LENGTH: 15
<212> TYPE: PRT
<213> ORGANISM: Zaire ebolavirus

<400> SEQUENCE: 426

Thr Gln Ala Leu Gln Leu Phe Leu Arg Ala Thr Thr Glu Leu Arg
1               5                   10                  15

<210> SEQ ID NO 427
<211> LENGTH: 15
<212> TYPE: PRT
<213> ORGANISM: Zaire ebolavirus

<400> SEQUENCE: 427

Val Asp Lys Thr Leu Pro Asp Gln Gly Asp Asn Asp Asn Trp Trp
```

-continued

```
1               5                   10                  15

<210> SEQ ID NO 428
<211> LENGTH: 15
<212> TYPE: PRT
<213> ORGANISM: Zaire ebolavirus

<400> SEQUENCE: 428

Ala Val Ser His Leu Thr Thr Leu Gly Thr Ile Ser Thr Ser Pro
1               5                   10                  15

<210> SEQ ID NO 429
<211> LENGTH: 15
<212> TYPE: PRT
<213> ORGANISM: Zaire ebolavirus

<400> SEQUENCE: 429

Gly Arg Arg Ala Arg Arg Glu Ala Ile Val Asn Ala Gln Pro Lys
1               5                   10                  15

<210> SEQ ID NO 430
<211> LENGTH: 15
<212> TYPE: PRT
<213> ORGANISM: Zaire ebolavirus

<400> SEQUENCE: 430

Glu Gln Leu Met Thr Gly Arg Ile Pro Val Ser Asp Ile Phe Cys
1               5                   10                  15

<210> SEQ ID NO 431
<211> LENGTH: 15
<212> TYPE: PRT
<213> ORGANISM: Zaire ebolavirus

<400> SEQUENCE: 431

Ser Gln Thr Gln Thr Asp Pro Ile Cys Asn His Ser Phe Glu Glu
1               5                   10                  15

<210> SEQ ID NO 432
<211> LENGTH: 15
<212> TYPE: PRT
<213> ORGANISM: Zaire ebolavirus

<400> SEQUENCE: 432

Ile Thr Ser Leu Glu Asn Gly Leu Lys Pro Val Tyr Asp Met Ala
1               5                   10                  15

<210> SEQ ID NO 433
<211> LENGTH: 15
<212> TYPE: PRT
<213> ORGANISM: Zaire ebolavirus

<400> SEQUENCE: 433

Arg Ala Thr Ala Thr Ala Ala Thr Glu Ala Tyr Trp Ala Glu
1               5                   10                  15

<210> SEQ ID NO 434
<211> LENGTH: 15
<212> TYPE: PRT
<213> ORGANISM: Zaire ebolavirus

<400> SEQUENCE: 434

Thr Val Pro Gln Ser Val Arg Glu Ala Phe Asn Asn Leu Asn Ser
1               5                   10                  15
```

```
<210> SEQ ID NO 435
<211> LENGTH: 15
<212> TYPE: PRT
<213> ORGANISM: Zaire ebolavirus

<400> SEQUENCE: 435

His Leu Pro Gly Phe Gly Thr Ala Phe His Gln Leu Val Gln Val
1               5                   10                  15

<210> SEQ ID NO 436
<211> LENGTH: 15
<212> TYPE: PRT
<213> ORGANISM: Zaire ebolavirus

<400> SEQUENCE: 436

Asp Ser Pro Gln Cys Ala Leu Ile Gln Ile Thr Lys Arg Val Pro
1               5                   10                  15

<210> SEQ ID NO 437
<211> LENGTH: 15
<212> TYPE: PRT
<213> ORGANISM: Zaire ebolavirus

<400> SEQUENCE: 437

Leu Arg Pro Val Pro Pro Ser Pro Lys Ile Asp Arg Gly Trp Val
1               5                   10                  15

<210> SEQ ID NO 438
<211> LENGTH: 15
<212> TYPE: PRT
<213> ORGANISM: Zaire ebolavirus

<400> SEQUENCE: 438

Phe Leu Thr Pro Glu Ser Val Asn Gly Asp Thr Pro Ser Asn Pro
1               5                   10                  15

<210> SEQ ID NO 439
<211> LENGTH: 15
<212> TYPE: PRT
<213> ORGANISM: Zaire ebolavirus

<400> SEQUENCE: 439

Glu Ala Met Val Asn Val Ile Ser Gly Pro Lys Val Leu Met Lys
1               5                   10                  15

<210> SEQ ID NO 440
<211> LENGTH: 15
<212> TYPE: PRT
<213> ORGANISM: Zaire ebolavirus

<400> SEQUENCE: 440

Met Leu Ala Ser Tyr Thr Ile Thr His Phe Gly Lys Ala Thr Asn
1               5                   10                  15

<210> SEQ ID NO 441
<211> LENGTH: 15
<212> TYPE: PRT
<213> ORGANISM: Zaire ebolavirus

<400> SEQUENCE: 441

Ala Phe Leu Gln Glu Phe Val Leu Pro Pro Val Gln Leu Pro Gln
1               5                   10                  15

<210> SEQ ID NO 442
```

```
<211> LENGTH: 15
<212> TYPE: PRT
<213> ORGANISM: Zaire ebolavirus

<400> SEQUENCE: 442

Pro Thr Gly Ser Asn Gly Ala Leu Arg Pro Gly Ile Ser Phe His
1               5                   10                  15

<210> SEQ ID NO 443
<211> LENGTH: 15
<212> TYPE: PRT
<213> ORGANISM: Zaire ebolavirus

<400> SEQUENCE: 443

Lys Ile Gln Ala Ile Met Thr Ser Leu Gln Asp Phe Lys Ile Val
1               5                   10                  15

<210> SEQ ID NO 444
<211> LENGTH: 15
<212> TYPE: PRT
<213> ORGANISM: Zaire ebolavirus

<400> SEQUENCE: 444

Val Thr Ser Lys Asn Gly Gln Pro Ile Ile Pro Val Leu Leu Pro
1               5                   10                  15

<210> SEQ ID NO 445
<211> LENGTH: 15
<212> TYPE: PRT
<213> ORGANISM: Zaire ebolavirus

<400> SEQUENCE: 445

Asp Thr Cys His Ser Pro Ala Ser Leu Pro Ala Val Ile Glu Lys
1               5                   10                  15

<210> SEQ ID NO 446
<211> LENGTH: 15
<212> TYPE: PRT
<213> ORGANISM: Zaire ebolavirus

<400> SEQUENCE: 446

Glu Ile Cys Gln Leu Ile Ile Gln Ala Phe Glu Ala Gly Val Asp
1               5                   10                  15

<210> SEQ ID NO 447
<211> LENGTH: 15
<212> TYPE: PRT
<213> ORGANISM: Zaire ebolavirus

<400> SEQUENCE: 447

Arg Leu Glu Glu Leu Leu Pro Ala Val Ser Ser Gly Lys Asn Ile
1               5                   10                  15

<210> SEQ ID NO 448
<211> LENGTH: 15
<212> TYPE: PRT
<213> ORGANISM: Zaire ebolavirus

<400> SEQUENCE: 448

Glu Gln Gly Leu Ile Gln Tyr Pro Thr Ala Trp Gln Ser Val Gly
1               5                   10                  15

<210> SEQ ID NO 449
<211> LENGTH: 15
<212> TYPE: PRT
```

<213> ORGANISM: Zaire ebolavirus

<400> SEQUENCE: 449

Ile Val Lys Thr Val Leu Asp His Ile Leu Gln Lys Thr Glu Arg
1               5                   10                  15

<210> SEQ ID NO 450
<211> LENGTH: 15
<212> TYPE: PRT
<213> ORGANISM: Zaire ebolavirus

<400> SEQUENCE: 450

Gly Leu Phe Pro Gln Leu Ser Ala Ile Ala Leu Gly Val Ala Thr
1               5                   10                  15

<210> SEQ ID NO 451
<211> LENGTH: 15
<212> TYPE: PRT
<213> ORGANISM: Zaire ebolavirus

<400> SEQUENCE: 451

Leu Met Asn Phe His Gln Lys Lys Asn Glu Ile Ser Phe Gln Gln
1               5                   10                  15

<210> SEQ ID NO 452
<211> LENGTH: 15
<212> TYPE: PRT
<213> ORGANISM: Zaire ebolavirus

<400> SEQUENCE: 452

His Gln Asp Asp Pro Thr Asp Ser Gln Asp Thr Thr Ile Pro
1               5                   10                  15

<210> SEQ ID NO 453
<211> LENGTH: 15
<212> TYPE: PRT
<213> ORGANISM: Zaire ebolavirus

<400> SEQUENCE: 453

Gly Gln Gln Lys Asn Ser Gln Lys Gly His Ile Glu Gly Arg
1               5                   10                  15

<210> SEQ ID NO 454
<211> LENGTH: 15
<212> TYPE: PRT
<213> ORGANISM: Zaire ebolavirus

<400> SEQUENCE: 454

Pro Leu Asp Asp Ala Asp Asp Glu Thr Ser Ser Leu Pro Pro Leu
1               5                   10                  15

<210> SEQ ID NO 455
<211> LENGTH: 15
<212> TYPE: PRT
<213> ORGANISM: Zaire ebolavirus

<400> SEQUENCE: 455

Asn Gln Asp Ser Asp Asn Thr Gln Ser Glu His Ser Phe Glu Glu
1               5                   10                  15

<210> SEQ ID NO 456
<211> LENGTH: 15
<212> TYPE: PRT
<213> ORGANISM: Zaire ebolavirus

```
<400> SEQUENCE: 456

Thr Glu Lys Glu Ala Met Asn Glu Glu Asn Arg Phe Val Thr Leu
1               5                   10                  15

<210> SEQ ID NO 457
<211> LENGTH: 15
<212> TYPE: PRT
<213> ORGANISM: Zaire ebolavirus

<400> SEQUENCE: 457

Ala Lys Val Lys Asn Glu Val Asn Ser Phe Leu Ala Ala Leu Ser
1               5                   10                  15

<210> SEQ ID NO 458
<211> LENGTH: 15
<212> TYPE: PRT
<213> ORGANISM: Zaire ebolavirus

<400> SEQUENCE: 458

Asp Arg Gly Trp Val Cys Val Phe Gln Leu Gln Asp Gly Lys Thr
1               5                   10                  15

<210> SEQ ID NO 459
<211> LENGTH: 15
<212> TYPE: PRT
<213> ORGANISM: Zaire ebolavirus

<400> SEQUENCE: 459

Cys Val Phe Gln Leu Gln Asp Gly Lys Thr Leu Gly Leu Lys Ile
1               5                   10                  15

<210> SEQ ID NO 460
<211> LENGTH: 20
<212> TYPE: PRT
<213> ORGANISM: Zaire ebolavirus

<400> SEQUENCE: 460

Asn Gly Leu Lys Pro Val Tyr Asp Met Ala Lys Thr Ile Ser Ser Leu
1               5                   10                  15

Asn Arg Val Cys
            20

<210> SEQ ID NO 461
<211> LENGTH: 15
<212> TYPE: PRT
<213> ORGANISM: Zaire ebolavirus

<400> SEQUENCE: 461

Asn Ile Leu Lys Phe Ile Asn Lys Leu Asp Ala Leu His Val Val
1               5                   10                  15
```

What is claimed is:

1. An Ebola virus vaccine comprising virus replicon particles expressing GP Ebola protein comprising the sequence specified in SEQ ID NO: 29.

2. An immunogenic composition comprising virus replicon particles expressing the GP Ebola peptide comprising the sequence specified in SEQ ID NO:29.

3. The immunogenic composition of claim 2, wherein the peptide consists of the CTL sequence of YFGPAAEGI (SEQ ID NO:42).

* * * * *